United States Patent
Park et al.

(10) Patent No.: US 11,271,175 B2
(45) Date of Patent: Mar. 8, 2022

(54) ORGANIC ELECTRONIC ELEMENT COMPRISING COMPOUND FOR ORGANIC ELECTRONIC ELEMENT, AND ELECTRONIC DEVICE THEREOF

(71) Applicant: DUK SAN NEOLUX CO., LTD., Cheonan-si (KR)

(72) Inventors: Junghwan Park, Hwaseong-si (KR); Sunhee Lee, Cheonan-si (KR); Wonsam Kim, Cheonan-si (KR); Jaewan Jang, Cheonan-si (KR); Hyeryeong Kim, Cheonan-si (KR); Yuri Kim, Wonju-si (KR); Gyumin Lee, Cheonan-si (KR); Yongwook Park, Anseong-si (KR)

(73) Assignee: DUK SAN NEOLUX CO., LTD., Cheonan-si (KR)

( * ) Notice: Subject to any disclaimer, the term of this patent is extended or adjusted under 35 U.S.C. 154(b) by 58 days.

(21) Appl. No.: 16/845,047

(22) Filed: Apr. 9, 2020

(65) Prior Publication Data

US 2020/0235314 A1 Jul. 23, 2020

Related U.S. Application Data

(62) Division of application No. 14/908,798, filed as application No. PCT/KR2014/006985 on Jul. 30, 2014, now Pat. No. 10,658,597.

(30) Foreign Application Priority Data

Aug. 5, 2013 (KR) .................. 10-2013-0092419
Jul. 25, 2014 (KR) .................. 10-2014-0094452

(51) Int. Cl.
*H01L 51/00* (2006.01)
*C09K 11/06* (2006.01)
*H01L 51/50* (2006.01)

(52) U.S. Cl.
CPC .......... *H01L 51/0073* (2013.01); *C09K 11/06* (2013.01); *H01L 51/006* (2013.01); *H01L 51/0052* (2013.01); *H01L 51/0059* (2013.01); *H01L 51/0074* (2013.01); *C09K 2211/1007* (2013.01); *C09K 2211/1011* (2013.01); *C09K 2211/1014* (2013.01); *C09K 2211/1029* (2013.01); *C09K 2211/1044* (2013.01);
(Continued)

(58) Field of Classification Search
CPC ... H01L 1/0074; H01L 1/0073; H01L 1/0052; H01L 1/0059; H01L 1/006; H01L 1/5012; H01L 1/5056; C09K 11/06; C09K 2211/1007; C09K 2211/1011; C09K 2211/1014; C09K 2211/1088; C09K 2211/1092
USPC ......... 428/690, 917; 548/440; 549/460, 345; 564/426, 427, 429, 430; 257/40
See application file for complete search history.

(56) References Cited

FOREIGN PATENT DOCUMENTS

KR 10-2014-0087882 A 7/2014
KR 20140087882 * 7/2014

* cited by examiner

*Primary Examiner* — Ruiyun Zhang
(74) *Attorney, Agent, or Firm* — Vorys, Sater, Seymour & Pease LLP; Mih Suhn Koh

(57) ABSTRACT

An organic electric element includes a first electrode, a second electrode, and an organic material layer between the first electrode and the second electrode. The organic material layer includes the compound represented by Formula 1. When the organic electric element includes the compound in the organic material layer, luminous efficiency, stability, and life span can be improved.

10 Claims, 1 Drawing Sheet

(52) U.S. Cl.
CPC ............... *C09K 2211/1088* (2013.01); *C09K 2211/1092* (2013.01); *H01L 51/5012* (2013.01); *H01L 51/5056* (2013.01); *H01L 51/5096* (2013.01); *Y02E 10/549* (2013.01)

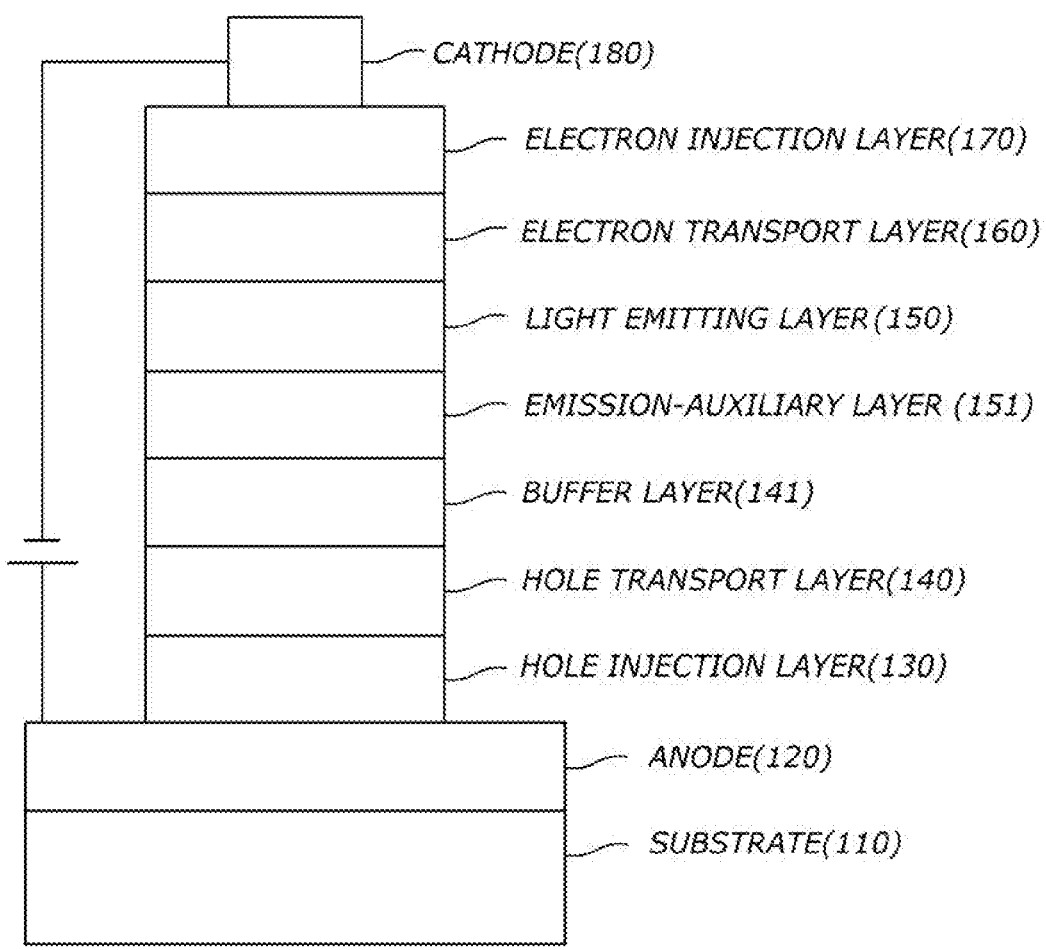

ORGANIC ELECTRONIC ELEMENT COMPRISING COMPOUND FOR ORGANIC ELECTRONIC ELEMENT, AND ELECTRONIC DEVICE THEREOF

CROSS-REFERENCE TO RELATED APPLICATION

This application is a Divisional Application of U.S. patent application Ser. No. 14/908,798 filed on Jan. 29, 2016, which was a 371 of PCT/KR2014/006985 filed on Jul. 30, 2014, and claims priority from and the benefit under 35 U.S.C. § 119(a) of Korean Patent Application No. 10-2013-0092419 filed on Aug. 5, 2013, and Korean Patent Application No. 10-2014-0094452 filed on Jul. 25, 2014, the contents of which are hereby incorporated by reference for all purposes as if fully set forth herein.

BACKGROUND

Technical Field

The present invention relates to compounds for organic electric elements, organic electric elements using the same, and electronic devices thereof.

Background Art

In general, an organic light emitting phenomenon refers to a phenomenon in which electric energy is converted into light energy of an organic material. An organic electric element utilizing the organic light emitting phenomenon usually has a structure including an anode, a cathode, and an organic material layer interposed therebetween. In many cases, the organic material layer may have a multilayered structure including multiple layers made of different materials in order to improve the efficiency and stability of an organic electric element, and for example, may include a hole injection layer, a hole transport layer, a light emitting layer, an electron transport layer, an electron injection layer, or the like.

A material used as an organic material layer in an organic electric element may be classified into a light emitting material and a charge transport material, for example, a hole injection material, a hole transport material, an electron transport material, an electron injection material, and the like according to its function.

Currently, the power consumption is required more than more as size of display becomes larger and larger in the portable display market. Therefore, the power consumption is a very important factor in the portable display with a limited power source of the battery, and efficiency and life span issue also is solved.

Efficiency, life span, driving voltage, and the like are correlated with each other. For example, if efficiency is increased, then driving voltage is relatively lowered, and the crystallization of an organic material due to Joule heating generated during operation is reduced as driving voltage is lowered, as a result of which life span shows a tendency to increase. However, efficiency cannot be maximized only by simply improving the organic material layer. This is because long life span and high efficiency can be simultaneously achieved when an optimal combination of energy levels and T1 values, inherent material properties (mobility, interfacial properties, etc.), and the like among the respective layers included in the organic material layer is given.

Further, in order to solve the emission problem with a hole transport layer in a recent organic electric element, an emission-auxiliary layer is present between the hole transport layer and a light emitting layer, and it is time to develop different emission-auxiliary layers according to respective light emitting layers (R, G, B).

In general, an electron transferred from an electron transport layer to a light emitting layer and a hole transferred from a hole transport layer to the light emitting layer are recombined to form an exciton. However, since a material used in a hole transporting layer should have a low HOMO value, it mainly has a low T1 value. Due to this, excitons generated from a light emitting layer are transported to the hole transporting layer, resulting in a charge unbalance in the light emitting layer. Thus, light emission occurs in the hole transporting layer or at an interface of the hole transporting layer so that the organic electroluminescent device is reduced in color purity, efficiency, and lifespan.

Also, when using a material having rapid hole mobility for reducing a driving voltage, this is tend to decrease the efficiency. In an OLEDs, a charge unbalance in the light emitting layer is caused because of that hole mobility is faster than electron mobility, and reduced efficiency and lifespan is happened.

Therefore, an emitting auxiliary layer must be formed by a material what can solve the problems of an hole transport layer, having hole mobility to give the suitable driving voltage, high T1 energy value and wide band gap. These requirements are not satisfied only by structural characteristics about a core of the emitting auxiliary layer's material. Therefore, it is necessary to develop of the material for the emitting auxiliary layer having high T1 energy value and wide band gap, to improve efficiency and lifespan of the organic electric element as combined core of material and characteristics of sub substituents appropriately.

In order to allow an organic electric element to fully exhibit the above-mentioned excellent features, it should be prerequisite to support a material constituting an organic material layer in the element, for example, a hole injection material, a hole transport material, a light emitting material, an electron transport material, an electron injection material, an emitting auxiliary layer, or the like, by a stable and efficient material. However, such a stable and efficient organic material layer material for an organic electric element has not yet been fully developed. Accordingly, there is a continuous need to develop new material of the emission-auxiliary layer, and material of the hole transport layer.

SUMMARY

In order to solve one or more of the above-mentioned problems occurring in the prior art, an aspect of the present invention is to provide an organic electric element using a compound which allows an organic electric element to have high luminous efficiency, low driving voltage, high heat-resistant, and to be improved in color purity and life span, and an electronic device including the organic electric element.

In accordance with an aspect of the present invention, there are provided organic electric elements comprising a first electrode, a second electrode, and a light emitting layer disposed between the first electrode and the second electrode, the organic electric element comprises an organic material layer disposed between the first electrode and the light emitting layer, the organic material layer comprising a compound represented by the following Formula.

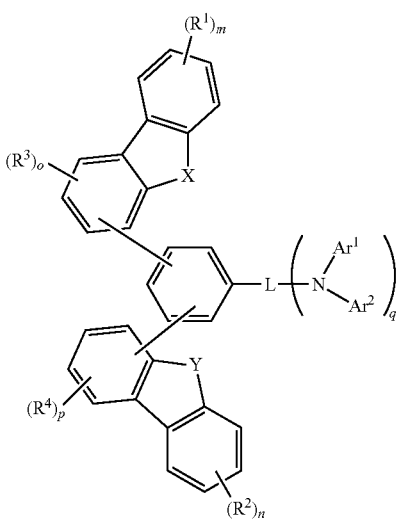

In another aspect of the present invention, there are provided electronic devices including the organic electric elements.

By using the compound according to embodiments of the present invention, an organic electric element according to one or more embodiments of the present invention not only has high luminous efficiency, low driving voltage and high heat-resistant and, but can also be significantly improved in color purity, and life span.

BRIEF DESCRIPTION OF THE DRAWINGS

The FIGURE illustrates an example of an organic light emitting diode according to an embodiment of the present invention.

DETAILED DESCRIPTION

Hereinafter, some embodiments of the present invention will be described in detail with reference to the accompanying illustrative drawings.

In designation of reference numerals to components in respective drawings, it should be noted that the same elements will be designated by the same reference numerals although they are shown in different drawings. Further, in the following description of the present invention, a detailed description of known functions and configurations incorporated herein will be omitted when it may make the subject matter of the present invention rather unclear.

In addition, terms, such as first, second, A, B, (a), (b) or the like may be used herein when describing components of the present invention. Each of these terminologies is not used to define an essence, order or sequence of a corresponding component but used merely to distinguish the corresponding component from other component(s). It should be noted that if it is described in the specification that one component is "connected," "coupled" or "joined" to another component, a third component may be "connected," "coupled," and "joined" between the first and second components, although the first component may be directly connected, coupled or joined to the second component. In addition, it will be understood that when an element such as a layer, film, region or substrate is referred to as being "on" or "over" another element, it can be directly on the other element or intervening elements may also be present. In contrast, when an element is referred to as being "directly on" another element, there are no intervening elements present.

As used in the specification and the accompanying claims, unless otherwise stated, the following is the meaning of the term as follows.

Unless otherwise stated, the term "halo" or "halogen" as used herein includes fluorine, chlorine, bromine, or iodine.

Unless otherwise stated, the term "alkyl" or "alkyl group" as used herein has a single bond of 1 to 60 carbon atoms, and means aliphatic functional radicals including a linear alkyl group, a branched chain alkyl group, a cycloalkyl group (alicyclic), or an alkyl group substituted with a cycloalkyl.

Unless otherwise stated, the term "haloalkyl" or "halogen alkyl" as used herein includes an alkyl group substituted with a halogen.

Unless otherwise stated, the term "alkenyl" or "alkynyl" as used herein has, but not limited to, double or triple bonds of 2 to 60 carbon atoms, and includes a linear alkyl group, or a branched chain alkyl group.

Unless otherwise stated, the term "cycloalkyl" as used herein means, but not limited to, alkyl forming a ring having 3 to 60 carbon atoms.

The term "alkoxyl group", or "alkyloxy group" as used herein means an oxygen radical attached to an alkyl group, but not limited to, and has 1 to 60 carbon atoms.

The term "aryloxyl group" or "aryloxy group" as used herein means an oxygen radical attached to an aryl group, but not limited to, and has 6 to 60 carbon atoms.

Unless otherwise stated, the term "fluorenyl group" or "fluorenylene group" as used herein means, univalent or bivalent functional group which R, R' and R" are all hydrogen in the structural formula below. Also, "substituted fluorenyl group" or "substituted fluorenylene group" means, functional group which at least any one of R, R' and R" is a functional group other than hydrogen and spiro compound which R and R' can be linked together with the carbone to which they are attached to form spiro compound.

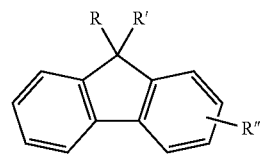

Unless otherwise stated, the term "aryl group" or "arylene group" as used herein has, but not limited to, 6 to 60 carbon atoms. The aryl group or arylene group means a monocyclic, ring assemblies, fused polycyclic system or spiro compound.

Unless otherwise stated, the term "heterocyclic group" as used herein means, but not limited to, a non-aromatic ring as well as an aromatic ring like "heteroaryl group" or "heteroarylene group". The heterocyclic group as used herein means, but not limited to, a ring containing one or more heteroatoms, and having 2 to 60 carbon atoms. Unless otherwise stated, the term "heteroatom" as used herein represents at least one of N, O, S, P, and Si. The heterocyclic group means a monocyclic, ring assemblies, fused polycyclic system or spiro compound containing one or more heteroatoms.

Also, the term "heterocyclic group" may include $SO_2$ instead of carbon consisting of cycle. For example, "heterocyclic group" includes the compound below.

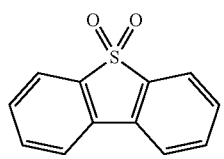 [SMILES: O=S1(=O)c2ccccc2-c2ccccc21]

Unless otherwise stated, the term "ring" as used herein means, a monocyclic and polycyclic, an aliphatic ring and heterocyclic group containing at least one heteroatom, and an aromatic ring and a non-aromatic ring.

Unless otherwise stated, the term "polycyclic" as used herein means, ring assemblies like biphenyl and terphenyl, fused polycyclic system and spiro compound, an aromatic ring and a non-aromatic ring, and an aliphatic ring and heterocyclic group containing at least one heteroatom.

Unless otherwise stated, the term "ring assemblies" as used herein means, two or more cyclic systems (single rings or fused systems) which are directly joined to each other by double or single bonds are named ring assemblies when the number of such direct ring junctions is one less than the number of cyclic systems involved. The ring assemblies also mean, same or different ring systems are directly joined to each other by double or single bonds.

Unless otherwise stated, the term "fused polycyclic system" as used herein means, fused ring type which has at least two atoms as the common members, fused two or more aliphatic ring systems and a fused hetero ring system containing at least one heteroatom. fused polycyclic system is an aromatic ring, a hetero aromatic ring, an aliphatic ring, or the combination of these.

Unless otherwise stated, the term "spiro compound" as used herein has, a spiro union which means union having one atom as the only common member of two rings. The common atom is designated as 'spiro atom'. The compounds are defined as 'monospiro-', 'dispiro-' or 'trispiro-' depending on the number of spiro atoms in one compound.

Also, when prefixes are named subsequently, it means that substituents are listed in the order described first. For example, an arylalkoxy means an alkoxy substituted with an aryl, an alkoxylcarbonyl means a carbonyl substituted with an alkoxyl, and an arylcarbonylalkenyl also means an alkenyl substitutes with an arylcarbonyl, wherein the arylcarbonyl may be a carbonyl substituted with an aryl.

Unless otherwise stated, the term "substituted or unsubstituted" as used herein means that substitution is carried out by at least one substituent selected from the group consisting of, but not limited to, deuterium, halogen, an amino group, a nitrile group, a nitro group, a $C_1$-$C_{20}$ alkyl group, a $C_1$-$C_{20}$ alkoxy group, a $C_1$alkylamine group, a $C_1$-$C_{20}$ alkylthio group, a $C_6$-$C_{20}$ arylthio group, a $C_2$-$C_{20}$ alkenyl group, a $C_2$-$C_{20}$ alkynyl group, a $C_3C_{20}$ cycloalkyl group, a $C_6$-$C_{60}$ aryl group, a fluorenyl group, a $C_6$-$C_{20}$ aryl group substituted by deuterium, a $C_8$-$C_{20}$ arylalkenyl group, a silane group, a boron group, a germanium group, and a $C_2C_{20}$ heterocyclic group containing at least one heteroatom selected from O, N, S, Si, and P.

Otherwise specified, the Formulas used in the present invention are as defined in the index definition of the substituent of the following Formula.

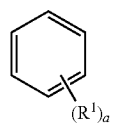

Wherein, when a is an integer of zero, the substituent $R^1$ is absent, when a is an integer of 1, the sole $R^1$ is linked to any one of the carbon atoms constituting the benzene ring, when a is an integer of 2 or 3, the substituent $R^1$s may be the same and different, and are linked to the benzene ring as follows. when a is an integer of 4 to 6, the substituents $R^1$s may be the same and different, and are linked to the benzene ring in a similar manner to that when a is an integer of 2 or 3, hydrogen atoms linked to carbon constituents of the benzene ring being not represented as usual.

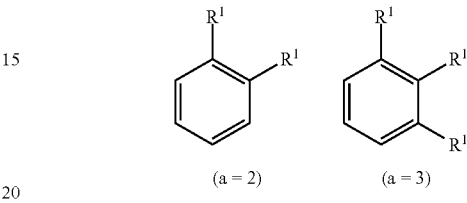

The FIGURE illustrates an organic electric element according to an embodiment of the present invention.

Referring to the FIGURE, an organic electric element 100 according to an embodiment of the present invention includes a first electrode 120 formed on a substrate 110, a second electrode 180, and an organic material layer between the first electrode 120 and the second electrode 180, which contains the inventive compound. Here, the first electrode 120 may be an anode (positive electrode), and the second electrode 180 may be a cathode (negative electrode). In the case of an inverted organic electric element, the first electrode may be a cathode, and the second electrode may be an anode.

The organic material layer includes a hole injection layer 130, a hole transport layer 140, a light emitting layer 150, an electron transport layer 160, and an electron injection layer 170 formed in sequence on the first electrode 120. Here, the layers included in the organic material layer, except the light emitting layer 150, may not be formed. The organic material layer may further include a hole blocking layer, an electron blocking layer, an emission-auxiliary layer 151, a buffer layer 141, etc., and the electron transport layer 160 and the like may serve as the hole blocking layer.

Although not shown, the organic electric element according to an embodiment of the present invention may further include at least one protective layer or one capping layer formed on at least one of the sides the first and second electrodes, which is a side opposite to the organic material layer.

The inventive compound employed in the organic material layer may be used as a host material, a dopant material, or a capping layer material in the hole injection layer 130, the hole transport layer 140, the electron transport layer 160, the electron injection layer 170, or the light emitting layer 150. For example, the inventive compound may be used as the hole transport layer 140, and/or the emission-auxiliary layer 151.

Since depending on the type and position of a substituent to be attached, a band gap, electrical properties, interfacial properties, and the like may vary even in the same core, it is very important what the types of core and a combination of substituent attached to the core are. Specially, long life span and high efficiency can be simultaneously achieved when an optimal combination of energy levels and T1 values, inherent material properties (mobility, interfacial properties, etc.), and the like among the respective layers included in the organic material layer is given.

As already described above, in order to solve the emission problem with a hole transport layer in a conventional organic electric element, an emission-auxiliary layer is preferably formed between the hole transport layer and a light emitting layer, and it is time to develop different emission-auxiliary layers according to respective light emitting layers (R, G, B). However, even when a similar core is used, it is very difficult to infer the characteristics of an emission-auxiliary layer if a used organic material layer varies because the correlation between the emission-auxiliary layer and a hole transport layer and the correlation between the emission-auxiliary layer and a light emitting layer (host) mused be discovered.

Accordingly, in the present invention, a combination of energy levels and T1 values, inherent material properties (mobility, interfacial properties, etc.), and the like among the respective layers included in the organic material layer is optimized by forming a hole transport layer, and/or an emission-auxiliary layer by using the compound represented by Formula 1, and thus the life span and efficiency of the organic electric element can be improved at the same time.

The organic electric element according to an embodiment of the present invention may be manufactured using various deposition methods. The organic electric element according to an embodiment of the present invention may be manufactured using a PVD(physical vapor deposition) method or CVD(chemical vapor deposition) method. For example, the organic electric element may be manufactured by depositing a metal, a conductive metal oxide, or a mixture thereof on the substrate to form the anode 120, forming the organic material layer including the hole injection layer 130, the hole transport layer 140, the light emitting layer 150, the electron transport layer 160, and the electron injection layer 170 thereon, and then depositing a material, which can be used as the cathode 180, thereon. Also, an emitting auxillary layer 151 may be comprised between the hole transport layer 140 and the light emitting layer 150.

And also, the organic material layer may be manufactured in such a manner that a smaller number of layers are formed using various polymer materials by a soluble process or solvent process, for example, spin coating, dip coating, doctor blading, screen printing, inkjet printing, or thermal transfer, instead of deposition. Since the organic material layer according to the present invention may be formed in various ways, the scope of protection of the present invention is not limited by a method of forming the organic material layer.

According to used materials, the organic electric element according to an embodiment of the present invention may be of a top emission type, a bottom emission type, or a dual emission type.

A WOLED (White Organic Light Emitting Device) readily allows for the formation of ultra-high definition images, and is of excellent processability as well as enjoying the advantage of being produced using conventional color filter technologies for LCDs. In this regard, various structures for WOLEDs, used as back light units, have been, in the most part, suggested and patented. Representative among the structures are a parallel side-by-side arrangement of R(Red), G(Green), B(Blue) light-emitting units, a vertical stack arrangement of RGB light-emitting units, and a CCM (color conversion material) structure in which electroluminescence from a blue (B) organic light emitting layer, and photoluminescence from an inorganic luminescent using the electroluminescence are combined. The present invention is applicable to these WOLEDs.

Further, the organic electric element according to an embodiment of the present invention may be any one of an organic light emitting diode (OLED), an organic solar cell, an organic photo conductor (OPC), an organic transistor (organic TFT), and an element for monochromatic or white illumination.

Another embodiment of the present invention provides an electronic device including a display device, which includes the above described organic electric element, and a control unit for controlling the display device. Here, the electronic device may be a wired/wireless communication terminal which is currently used or will be used in the future, and covers all kinds of electronic devices including a mobile communication terminal such as a cellular phone, a personal digital assistant (PDA), an electronic dictionary, a point-to-multipoint (PMP), a remote controller, a navigation unit, a game player, various kinds of TVs, and various kinds of computers.

Hereinafter, an organic electric element according to an aspect of the present invention will be described.

In accordance with an aspect of the present invention, there is provided an organic electric elements comprising a first electrode, a second electrode, and a light emitting layer disposed between the first electrode and the second electrode, the organic electric element comprises an organic material layer disposed between the first electrode and the light emitting layer, the organic material layer comprising a compound represented by Formula 1.

[Formula 1]

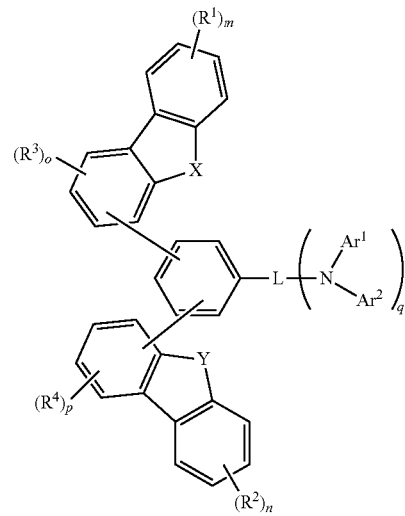

In formula 1 above, each symbol may be defined as follows.

In formula 1 above, X and Y may be each independently O or S. For example, X and Y can be all O or S, X is O and Y is S, or X is S and Y is O.

In formula 1 above, $Ar^1$ and $Ar^2$ may be each independently selected from the group consisting of a $C_6$-$C_{60}$ aryl group, a fluorenyl group and combinations thereof. q is an integer of 1 or 2, and each of $Ar^1$ and $Ar^2$ may be the same or different when q is 2.

Preferably, $Ar^1$ and $Ar^2$ may be each independently a $C_6$-$C_{25}$ aryl group or a fluorenylene group, also preferably, $C_6$, $C_{10}$, $C_{12}$ aryl group, and more preferably, substituted or unsubstituted with naphthyl phenyl group, naphthyl group, biphenyl group, substituted or unsubstituted with methyl or phenyl fluorenyl group, or spirobifluorenyl group.

Also, $Ar^1$ and $Ar^2$ may be optionally substituted with one or more substituents selected from the group consisting of deuterium, halogen, a silane group, a siloxane group, a boron group, a germanium group, a cyano group, a nitro group, a $C_1$-$C_{20}$ alkylthio group, a $C_1$-$C_{20}$ alkoxy group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_3$-$C_{20}$ cycloalkyl group, a $C_7$-$C_{20}$ arylalkyl group, and a $C_8$-$C_{20}$ arylalkenyl group.

In formula 1 above, L may be selected from the group consisting of a $C_6$-$C_{60}$ arylene group, a fluorenylene group, a fused ring group of a $C_3$-$C_{60}$ aliphatic ring and a $C_6$-$C_{60}$ aromatic ring, a $C_2$-$C_{60}$ heterocyclic group containing at least one heteroatom selected from the group consisting of O, N, S, Si, and P, and combinations thereof.

Preferably, L may be selected from the group consisting of a $C_6$-$C_{13}$ arylene group, a fluorenylene group, and a $C_3$-$C_{12}$ heterocyclic group, also preferably be a $C_6$ arylene group, or $C_4$, $C_5$ heterocyclic group, specifically phenylene group, substituted or unsubstituted with methyl fluorenylene group, pyridylene group or pyrimidinylene group.

Also preferably, L may be optionally substituted with one or more substituents selected from the group consisting of deuterium, halogen, a silane group, a siloxane group, a boron group, a germanium group, a cyano group, a nitro group, a $C_1$-$C_{20}$ alkylthio group, a $C_1$-$C_{20}$ alkoxy group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted by deuterium, a fluorenyl group, a $C_2$-$C_{20}$ heterocyclic group containing at least one heteroatom selected from the group consisting of O, N, S, Si, and P, a $C_3$-$C_{20}$ cycloalkyl group, a $C_7$-$C_{20}$ arylalkyl group, and a $C_8$-$C_{20}$ arylalkenyl group.

In formula 1 above, $R^1$ to $R^4$ may be each independently selected from the group consisting of hydrogen, deuterium, halogen, a $C_6$-$C_{60}$ aryl group, a fluorenyl group, a $C_2$-$C_{60}$ heterocyclic group containing at least one heteroatom selected from the group consisting of O, N, S, Si, and P, a fused ring group of a $C_3$-$C_{20}$ aliphatic ring and a $C_6$-$C_{60}$ aromatic ring, $C_1$-$C_{50}$ alkyl group, $C_2$-$C_{20}$ alkenyl group, $C_2$-$C_{20}$ alkynyl group, $C_1$-$C_{30}$ alkoxy group, $C_6$-$C_{30}$ aryloxy group, —L'—$N(R^a)(R^b)$ and combinations thereof. Each of m and n may be an integer of 0 to 4, each of o and p may be an integer of 0 to 3. When m, n, o and p are each an integer of 2 or more, each of plural $R^1$, $R^2$, $R^3$ and $R^4$ may be the same or different.

Preferably, $R^1$ to $R^4$ may be optionally substituted with one or more substituents selected from the group consisting of deuterium, halogen, a silane group, a siloxane group, a boron group, a germanium group, a cyano group, a nitro group, a $C_1$-$C_{20}$ alkylthio group, a $C_1$-$C_{20}$ alkoxy group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_2$-$C_{20}$ heterocyclic group containing at least one heteroatom selected from the group consisting of O, N, S, Si, and P, a $C_3$-$C_{20}$ cycloalkyl group, a $C_7$-$C_{20}$ arylalkyl group, and a $C_8$-$C_{20}$ arylalkenyl group.

Also, any two adjacent groups of $R^1$'s to $R^4$'s may be optionally formed ring, and $R^1$ to $R^4$ don't form ring may be the same as defined above. And the formed ring may be mono- or poly-cyclic ring.

L' may be selected from the group consisting of a single bond, a $C_6$-$C_{60}$ arylene group, a fluorenylene group, a fused ring group of a $C_3$-$C_{60}$ aliphatic ring and a $C_6$-$C_{60}$ aromatic ring, and a $C_2$-$C_{60}$ heterocyclic group containing at least one heteroatom selected from the group consisting of O, N, S, Si, and P.

$R^a$ and $R^b$ may be each independently selected from the group consisting of a $C_6$-$C_{60}$ aryl group, a fluorenyl group, a fused ring group of a $C_3$-$C_{60}$ aliphatic ring and a $C_6$-$C_{60}$ aromatic ring, and a $C_2$-$C_{60}$ heterocyclic group containing at least one heteroatom selected from the group consisting of O, N, S, Si, and P.

Specifically, the compound of Formula 1 in the organic material layer above may be represented by the following Formula 2 to Formula 5.

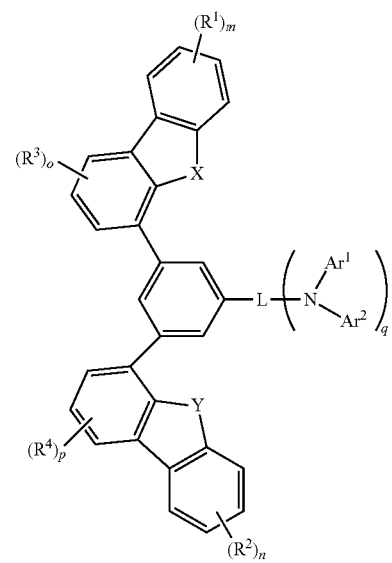

[Formula 2]

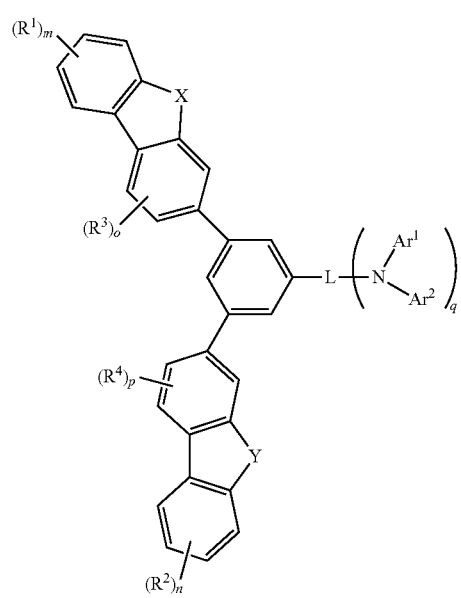

[Formula 3]

[Formula 4]

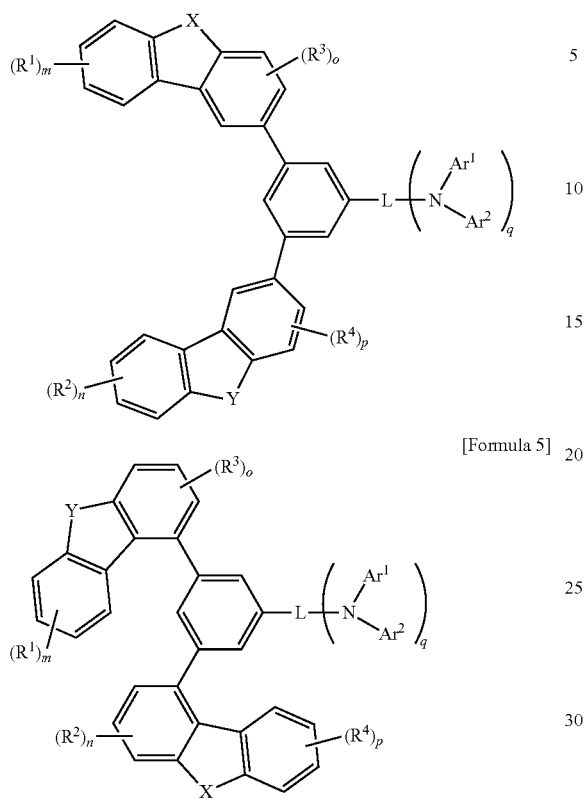

[Formula 5]

In Formula 2 to Formula 5, X, Y, Ar¹, Ar², L, R¹ to R⁴, m, n, o, p and q may be the same as defined in Formula 1 above.

Specifically, the compound of Formula 1 in the organic material layer above may be represented by the following Formula 6 and Formula 7. Formula 6 is represented when q is 1, Formula 7 is represented when q is 2. In the formula 7, Ar¹s may be the same or different, and Ar²s may be the same or different.

[Formula 6]

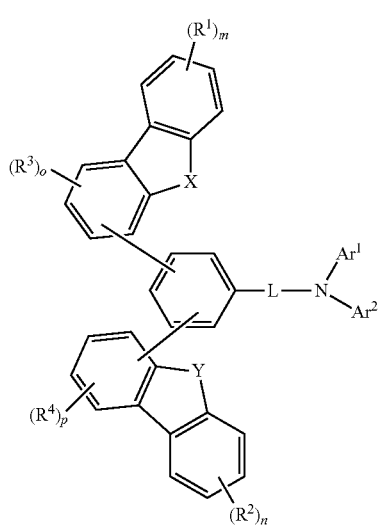

[Formula 7]

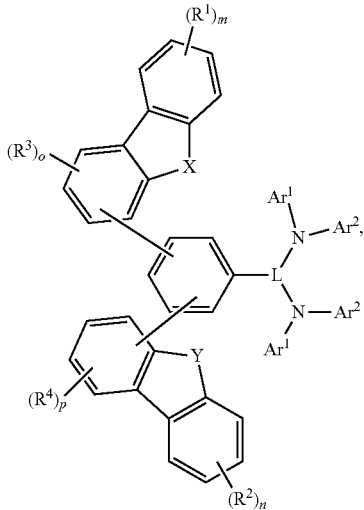

wherein, X, Y, Ar¹, Ar², L, R¹ to R⁴, m, n, o and p may be the same as defined in Formula 1.

More specifically, the compound of Formula 1 in the organic material layer above may be represented by one of the following compounds.

1-1

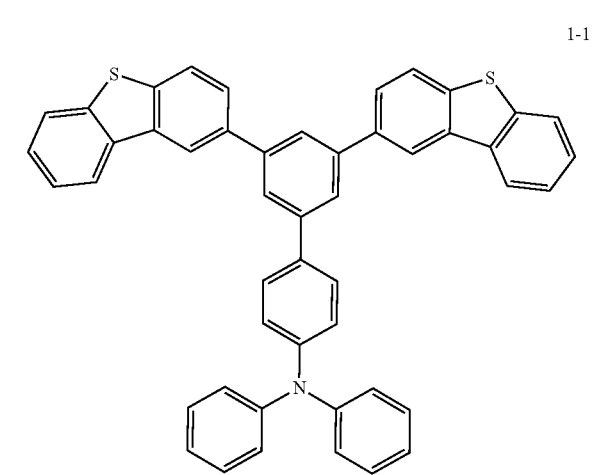

1-2
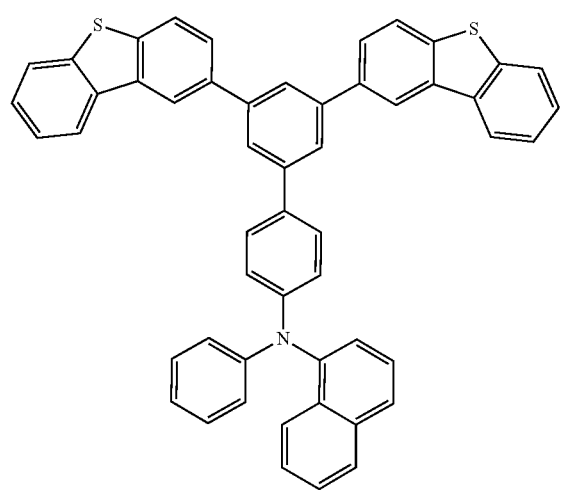
1-3
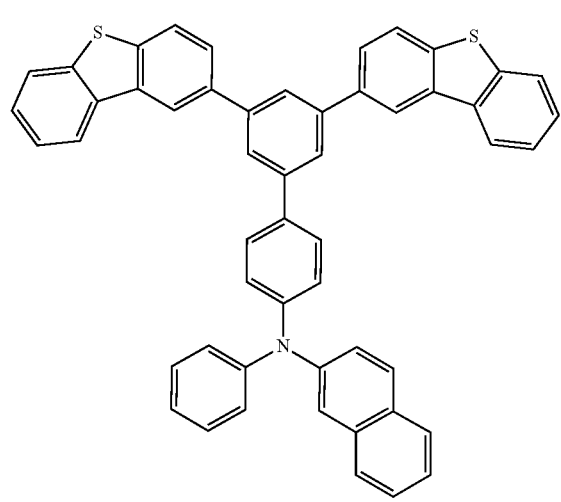
1-4
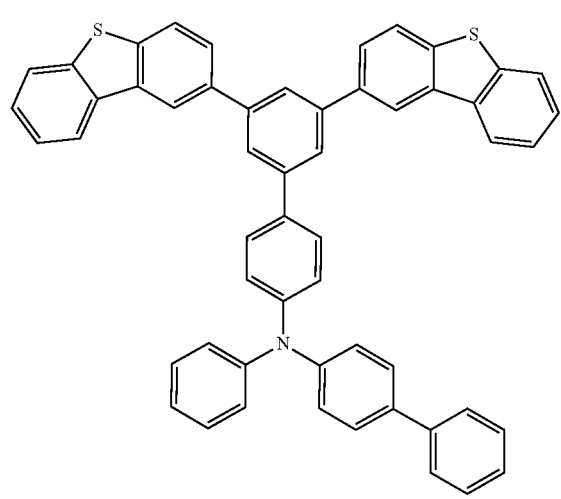
1-5
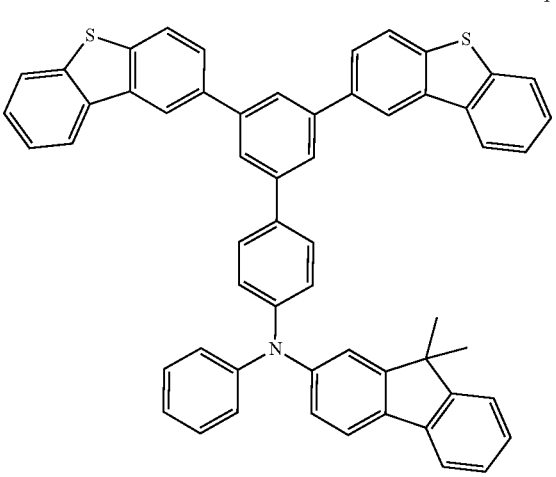
1-6
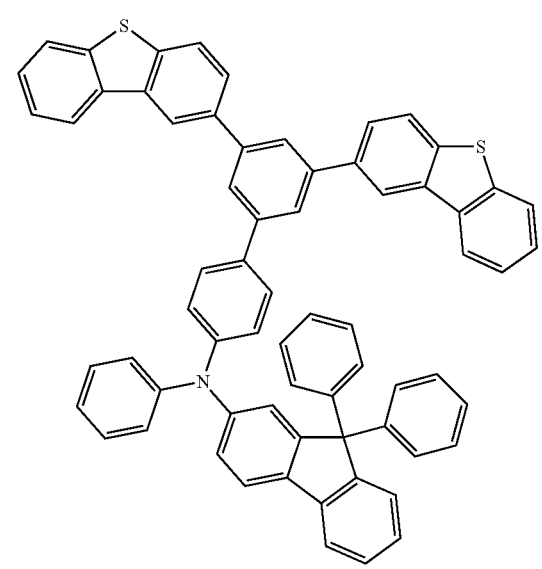
1-7
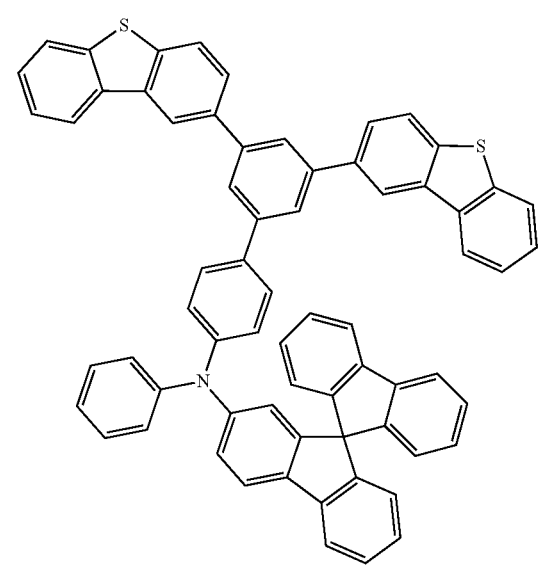

1-8
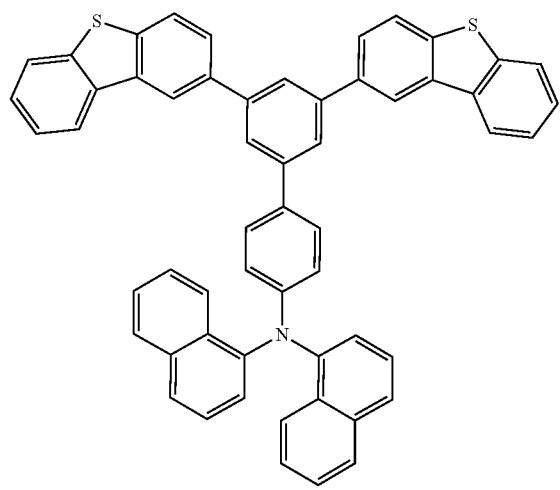
1-9
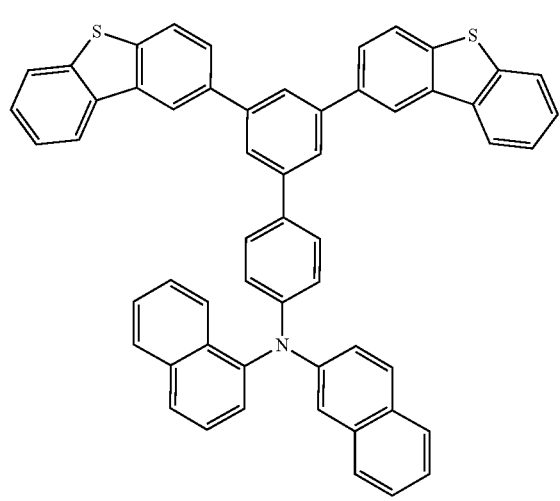
1-10
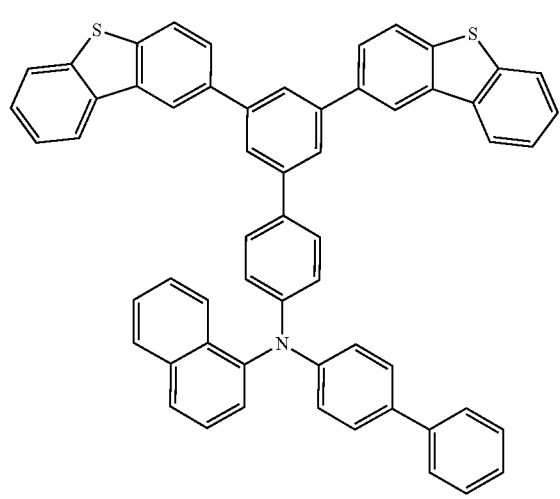
1-11
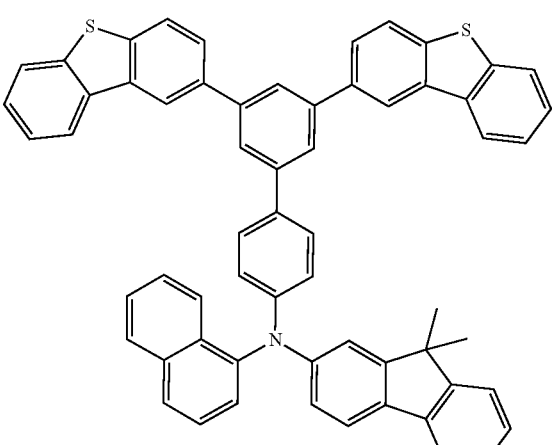
1-12
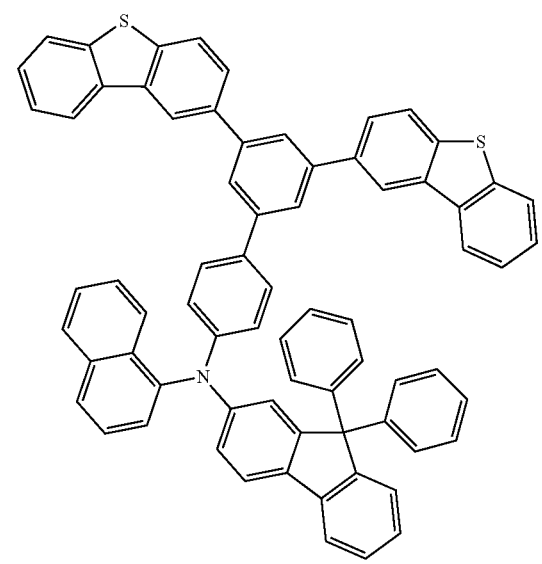
1-13
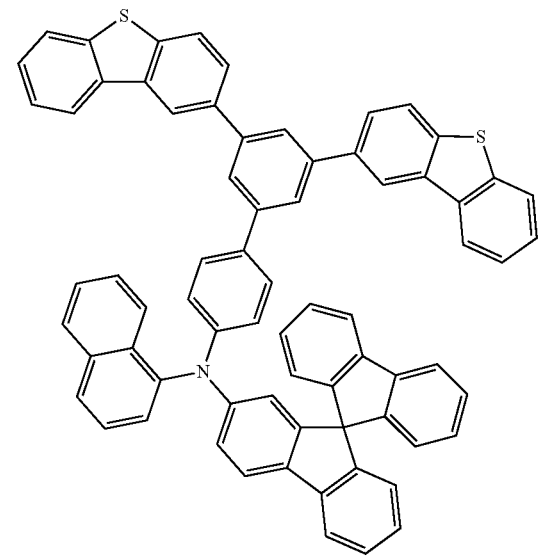

1-14
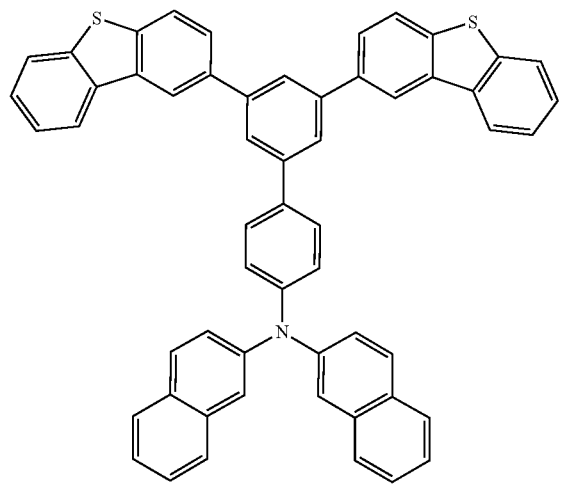
1-15
1-16
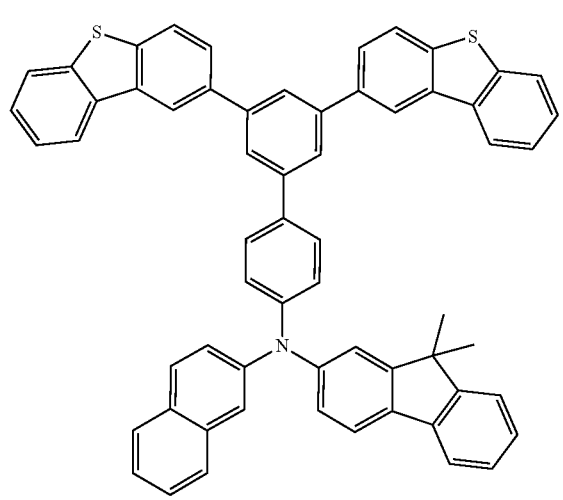
1-17
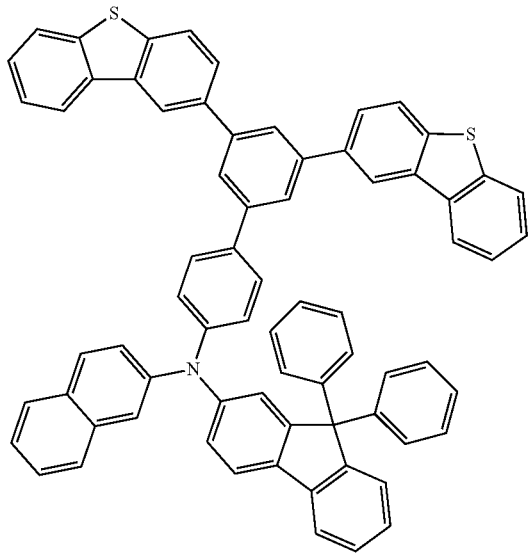
1-18
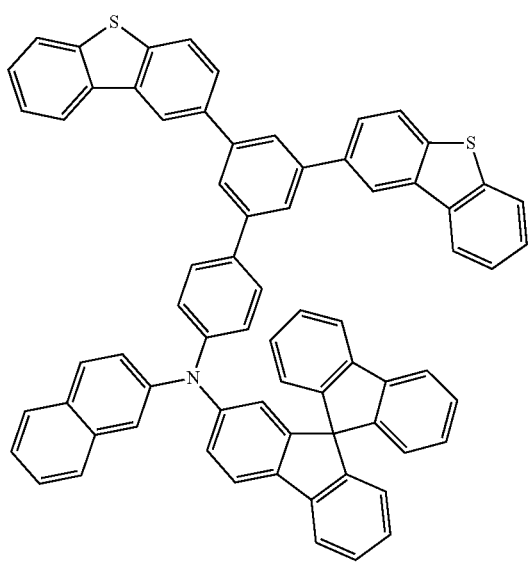
1-19

1-20
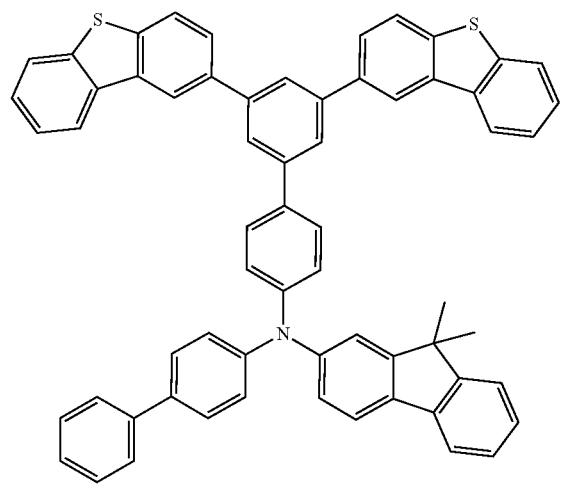
1-21
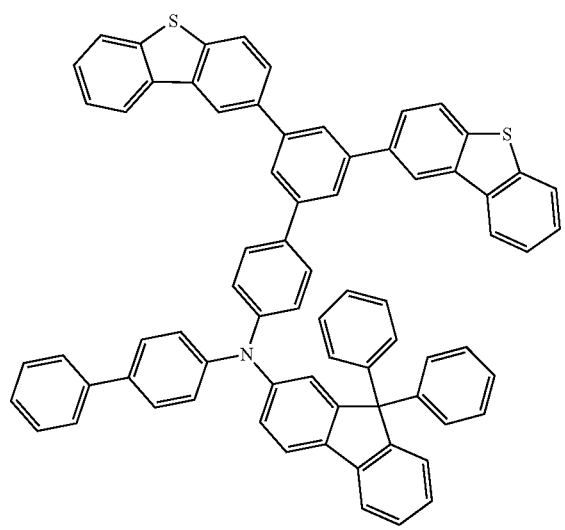
1-22
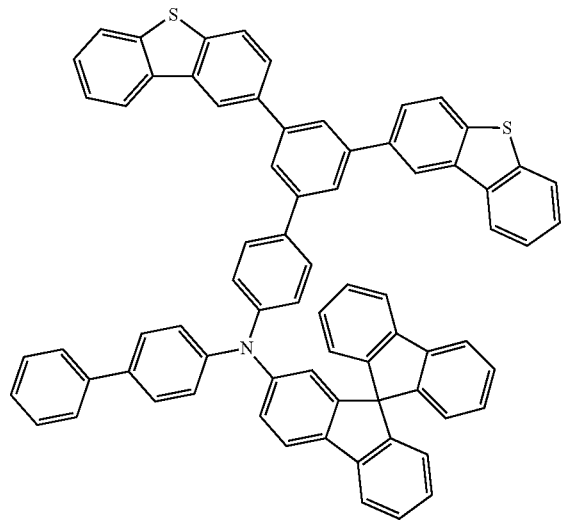
1-23
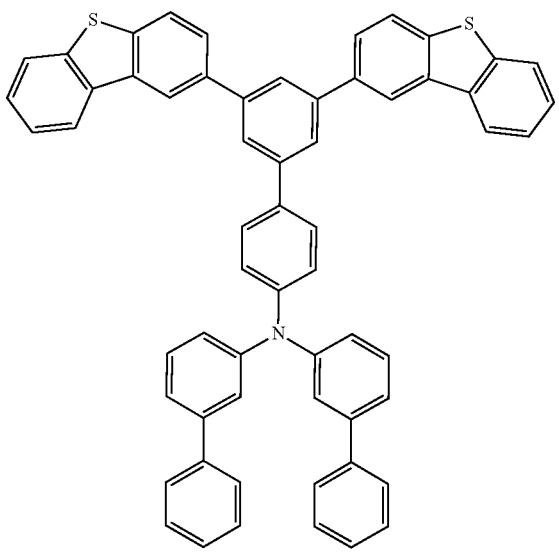
1-24
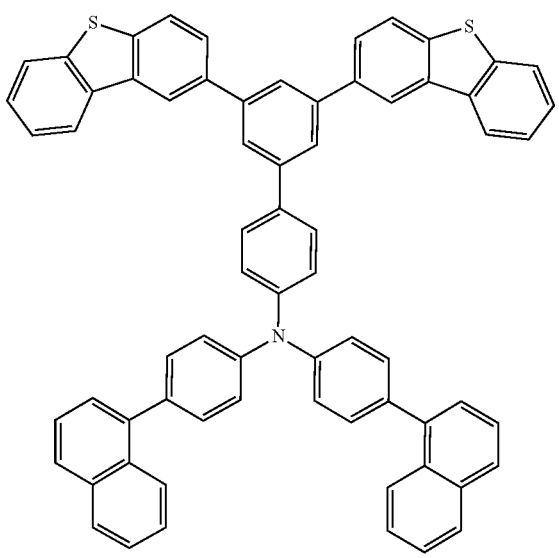
1-25

-continued
1-26
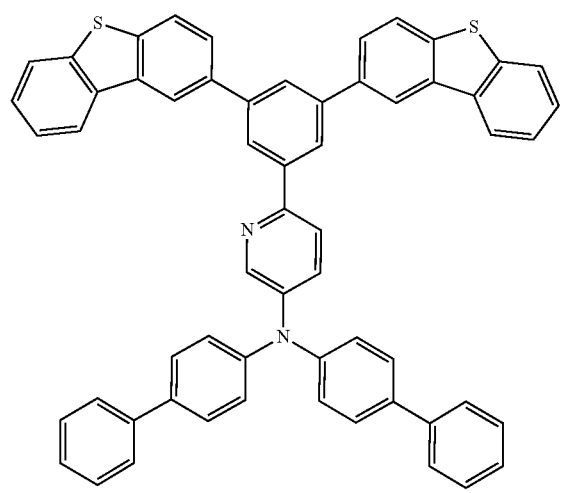
1-27
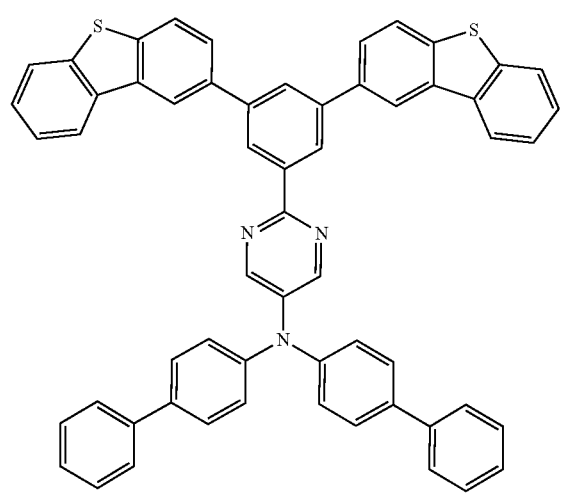
1-28
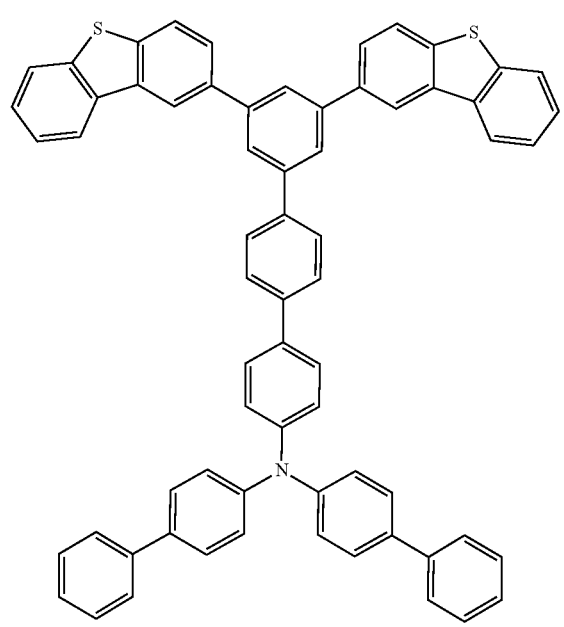
-continued
2-1
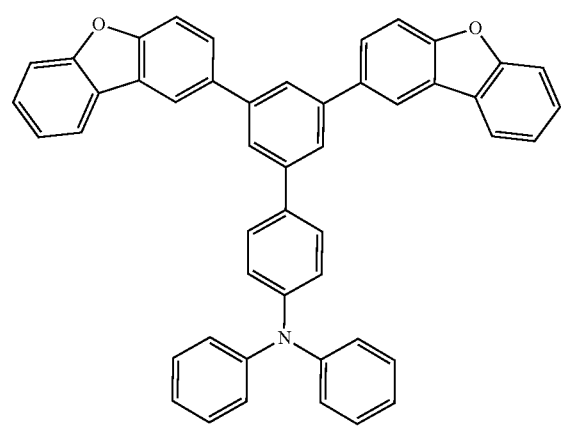
2-2
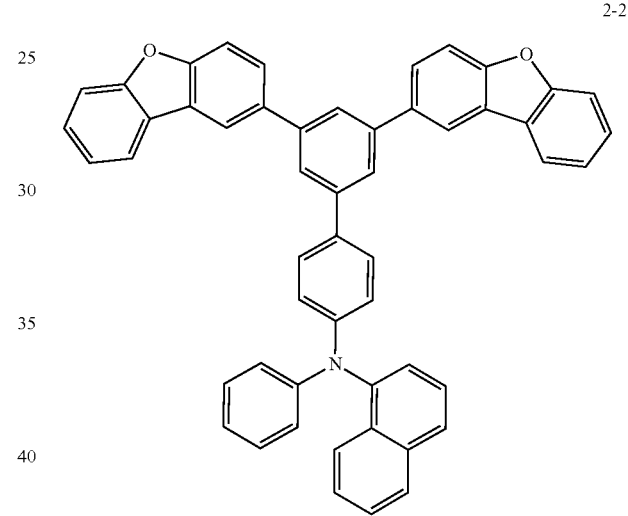
2-3
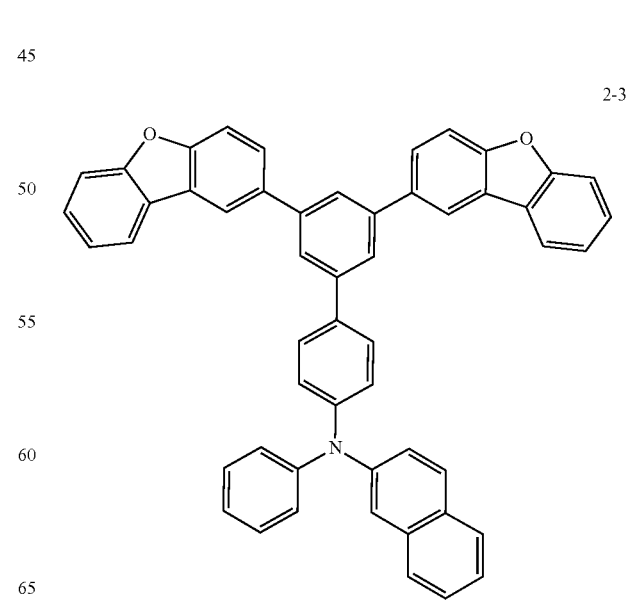

2-4
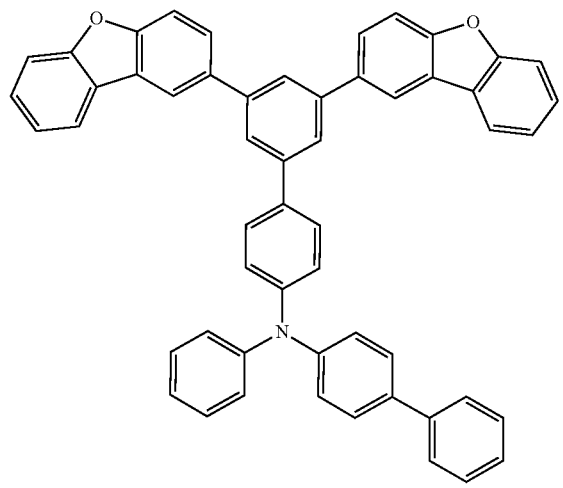
2-5
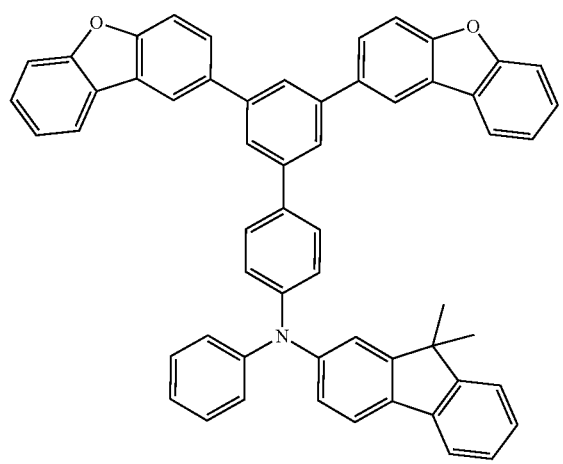
2-6
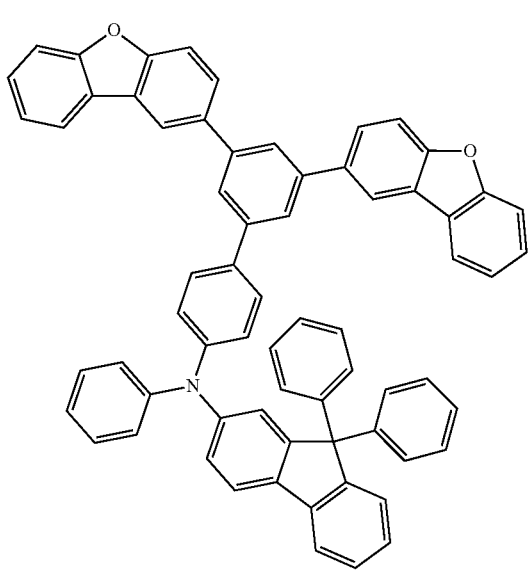
2-7
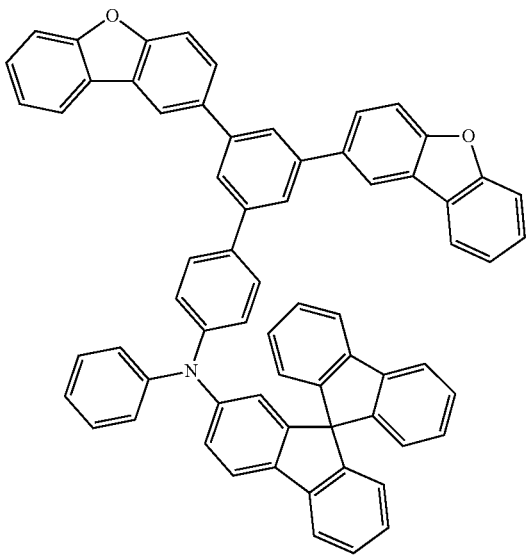
2-8
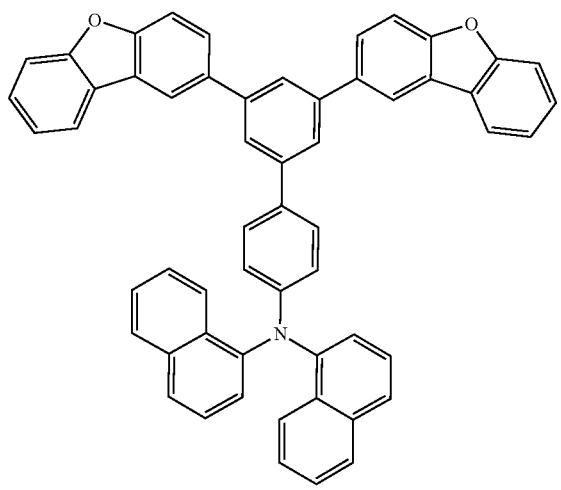
2-9
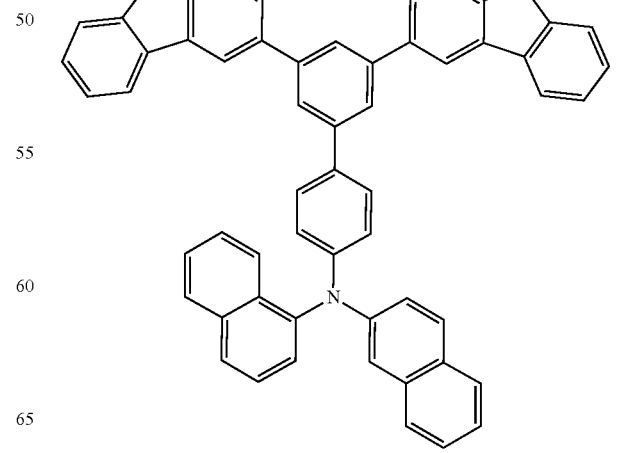

-continued
2-10
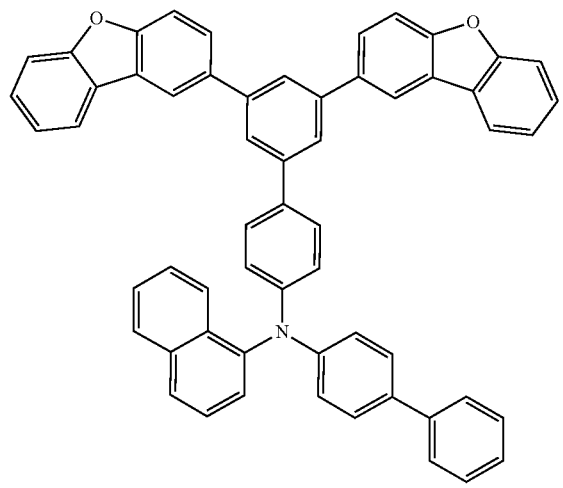
2-11
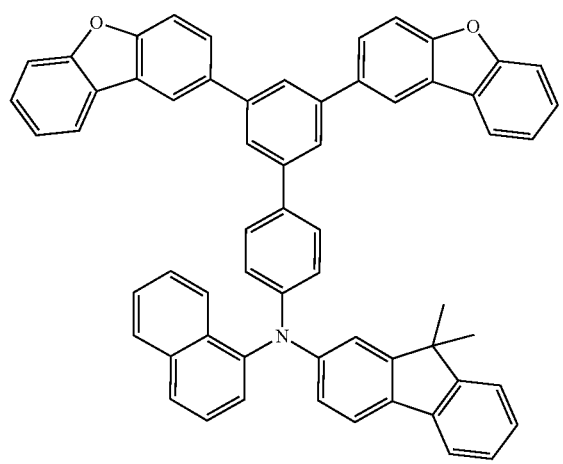
2-12
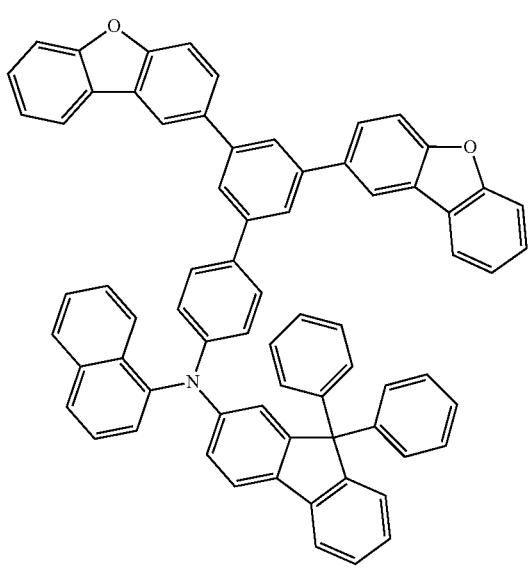
-continued
2-13
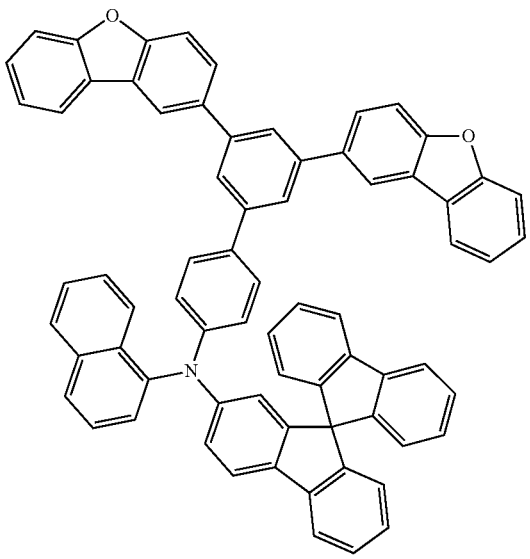
2-14
2-15
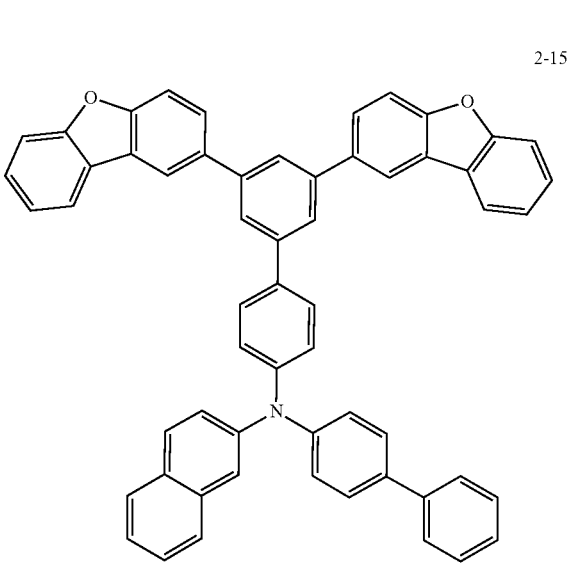

2-16
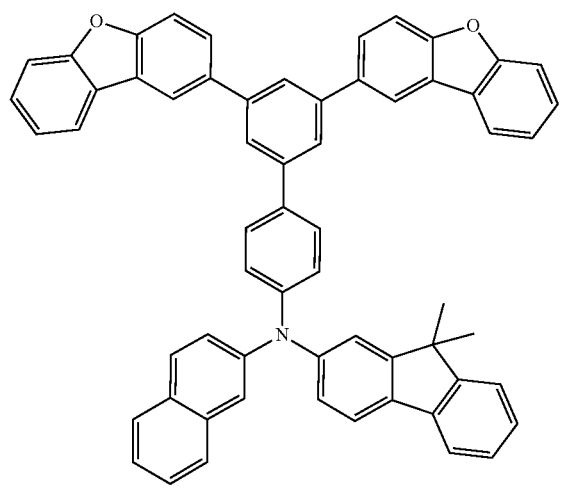
2-17
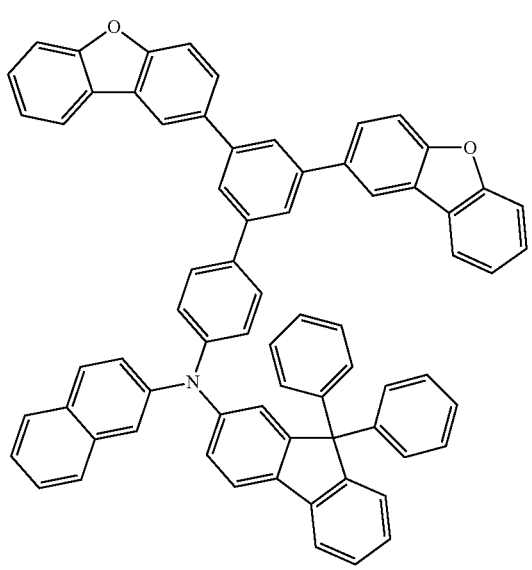
2-18
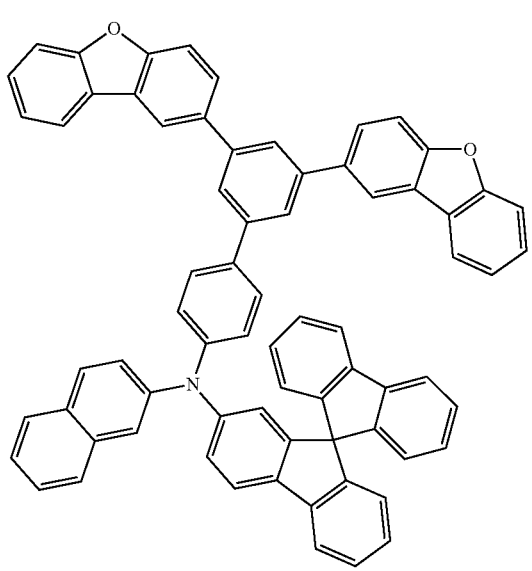
2-19
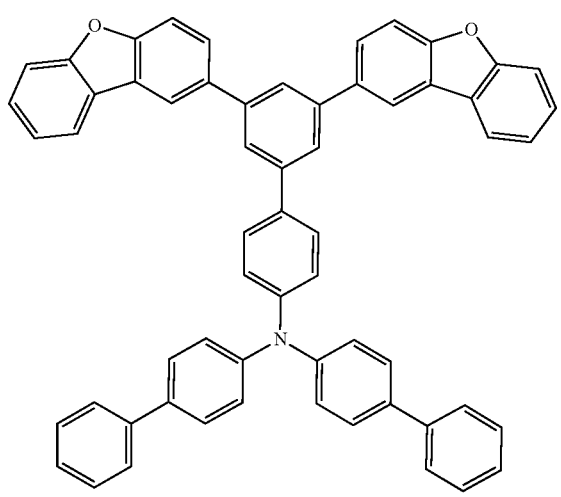
2-20
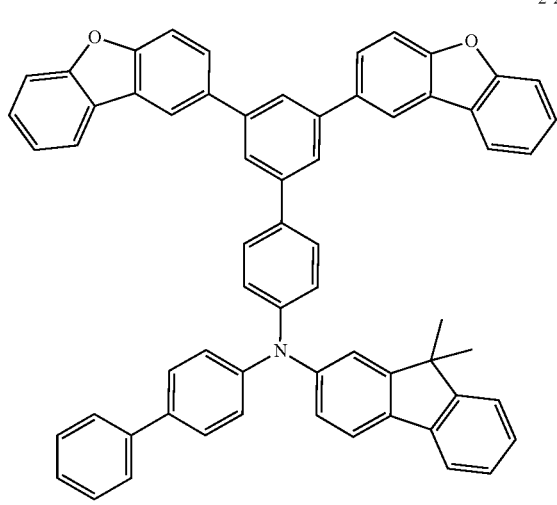
2-21
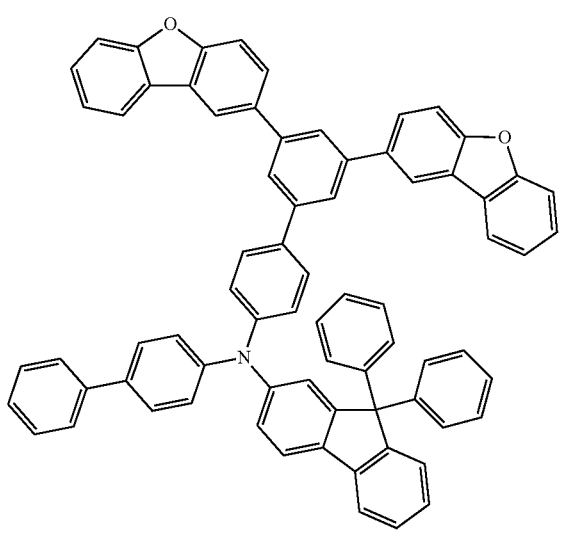

2-22
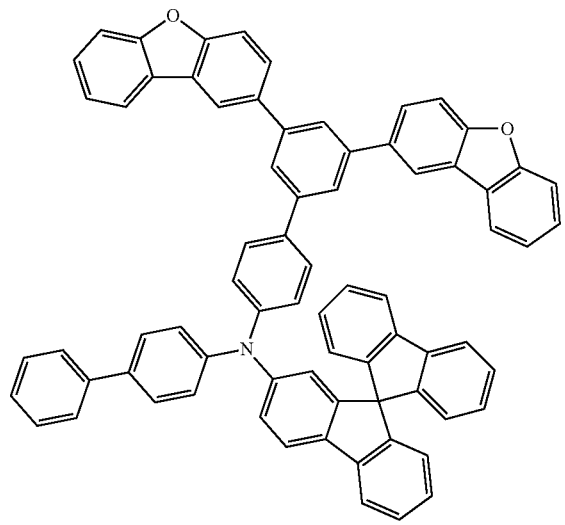
2-24
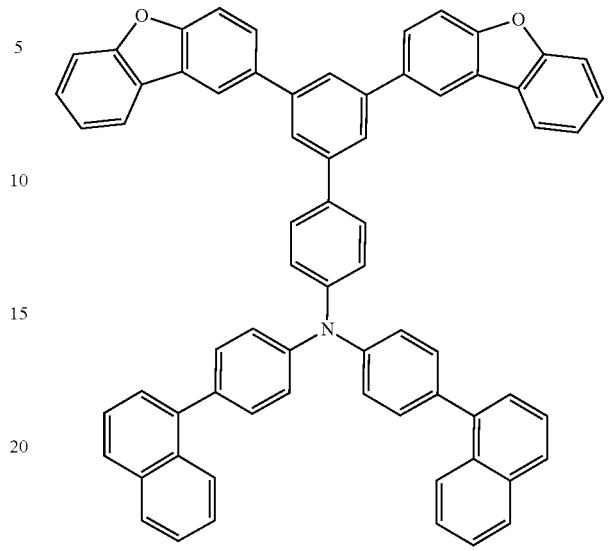
2-25
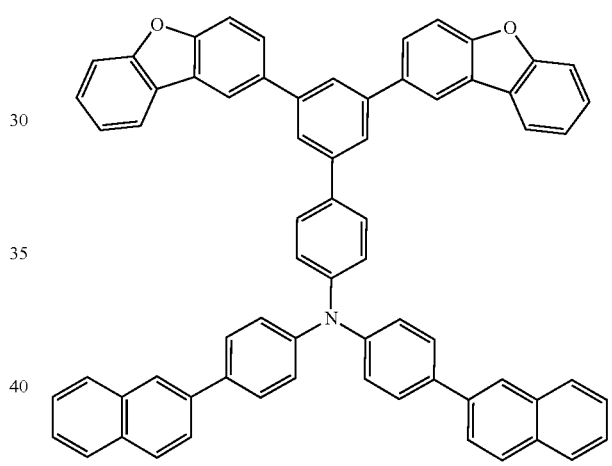
2-23
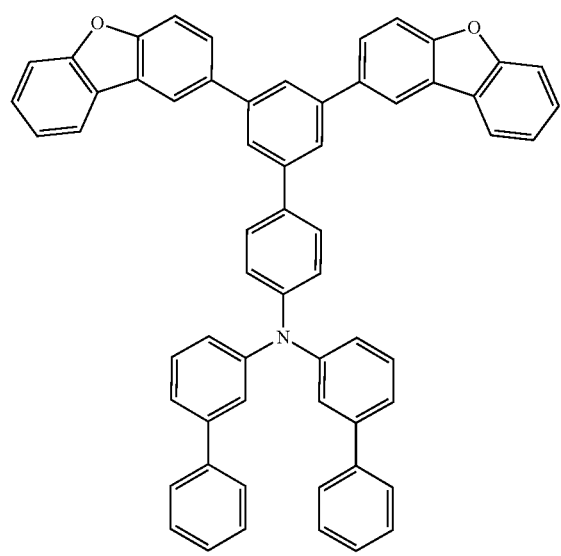
2-26
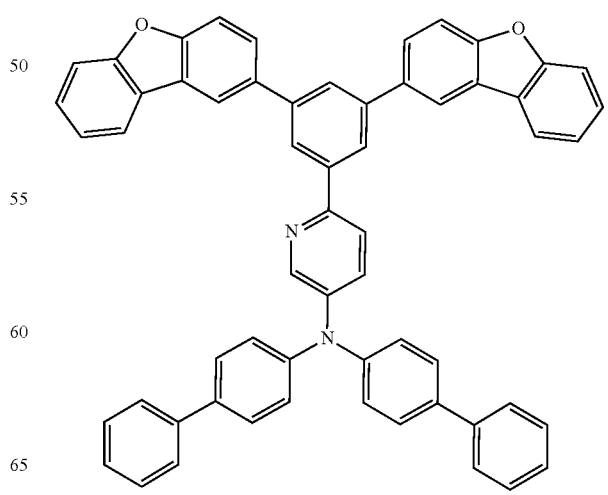

2-27
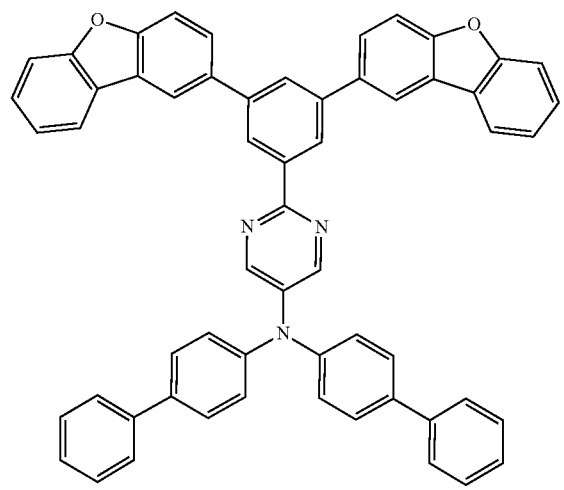
2-28
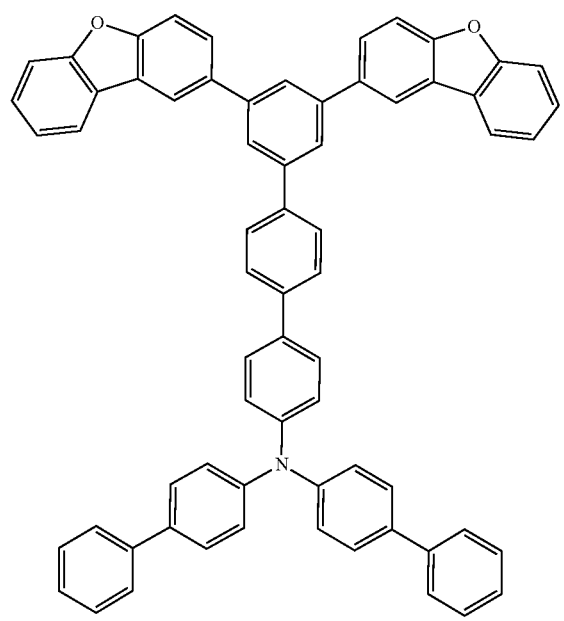
3-1
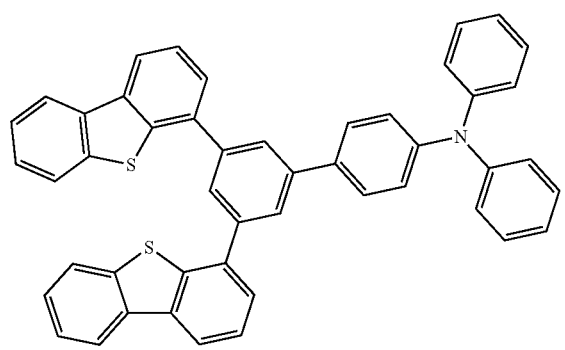
3-2
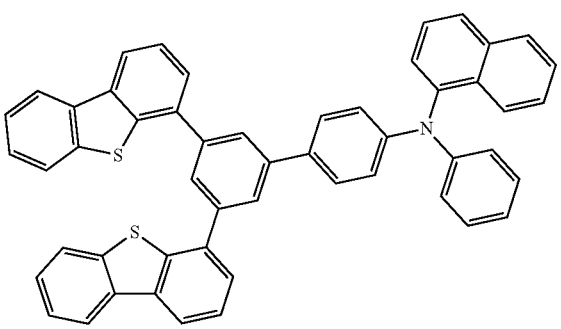
3-3
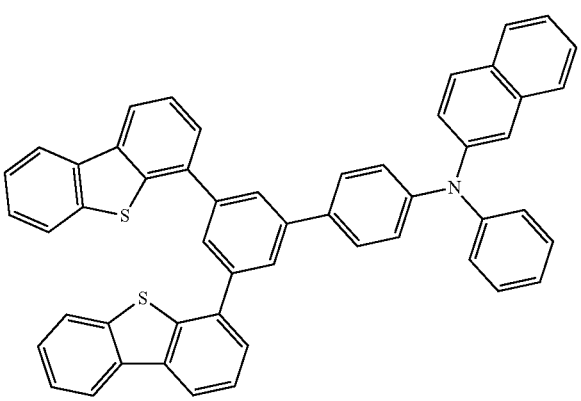
3-4
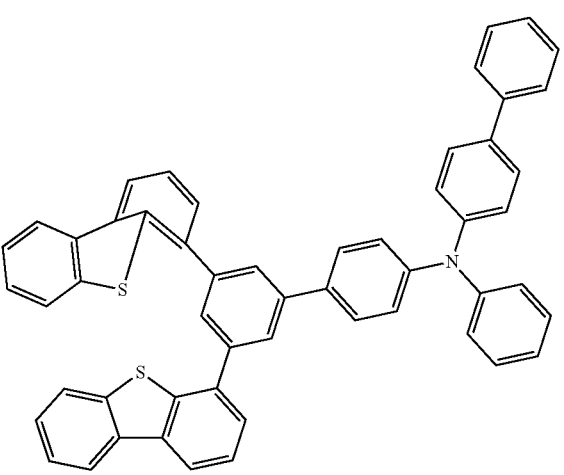

3-5
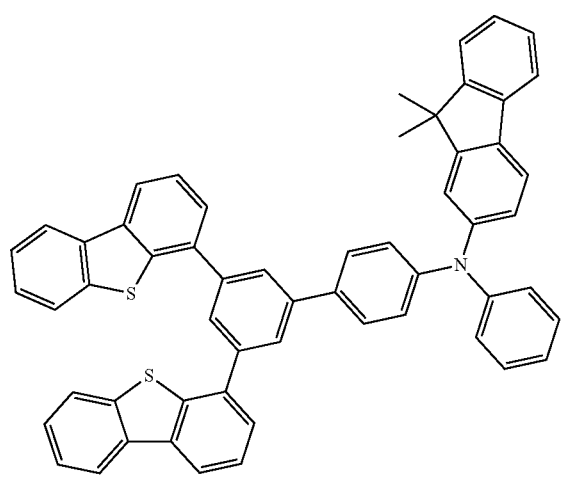
3-8
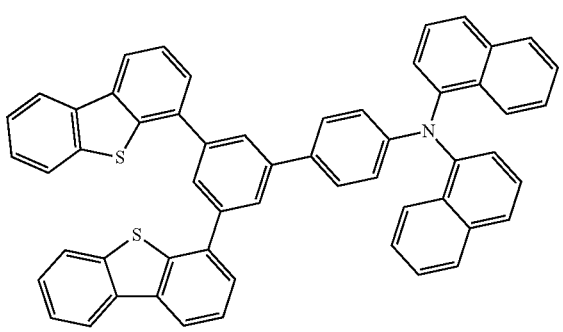
3-6
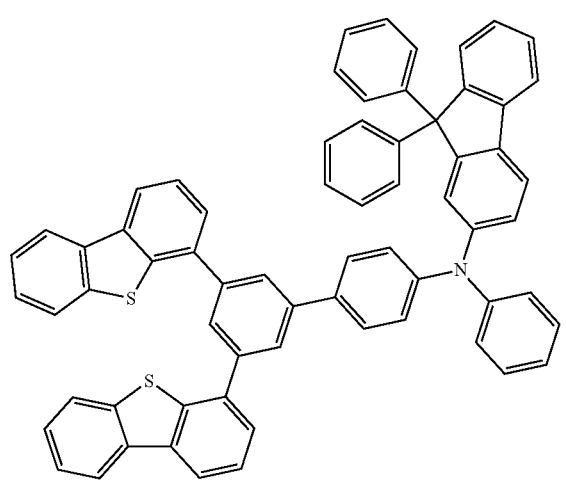
3-9
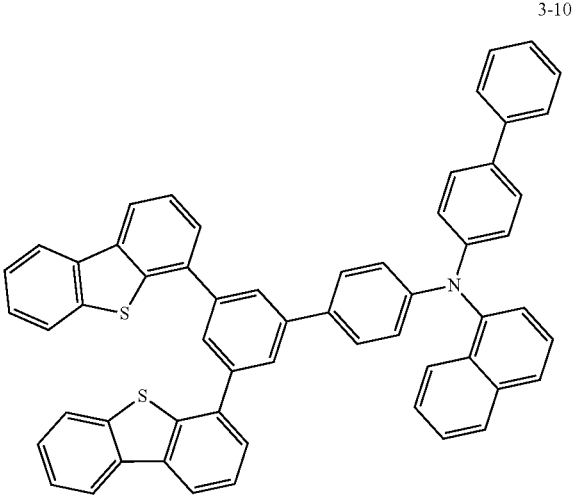
3-7
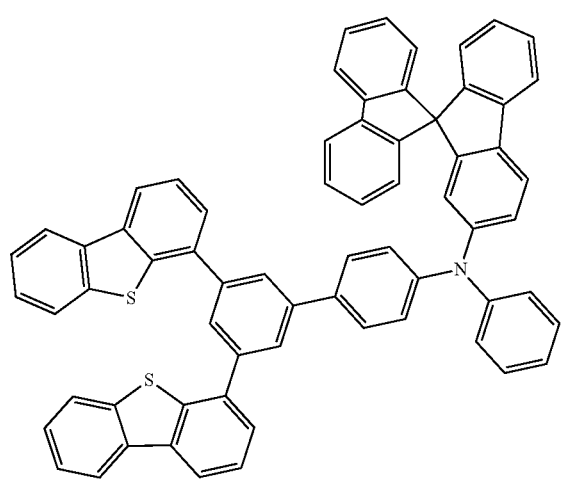
3-10

-continued
3-11
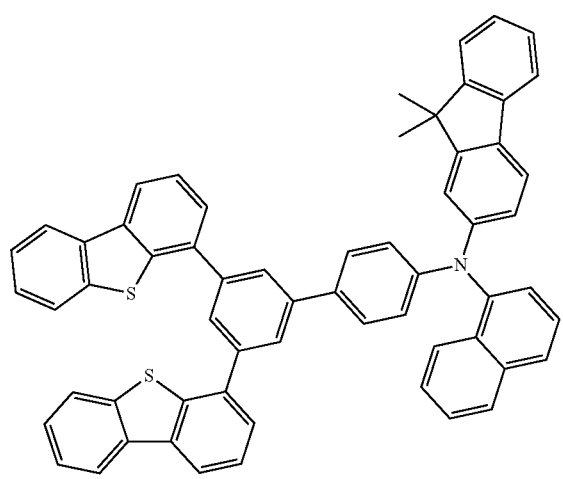
3-12
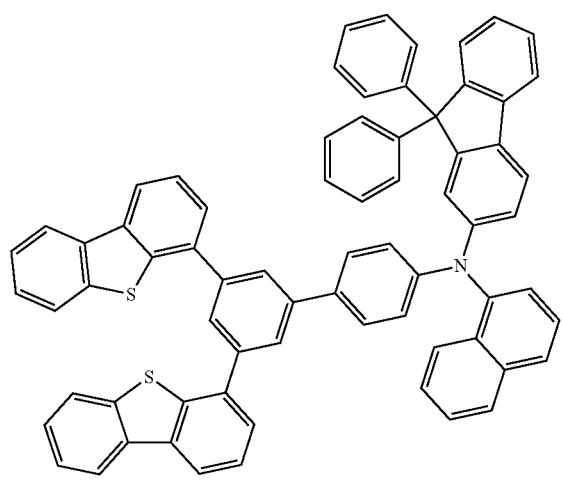
3-13
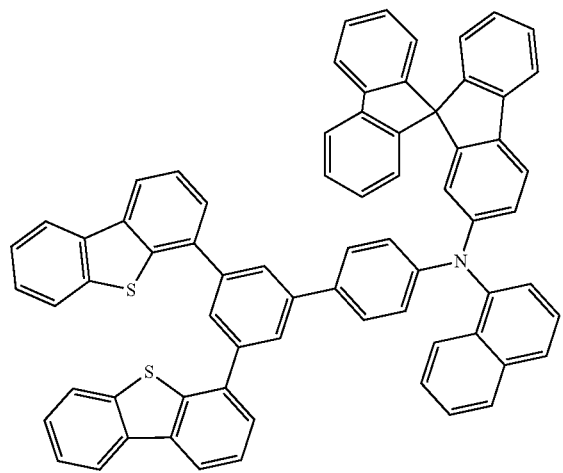
-continued
3-14
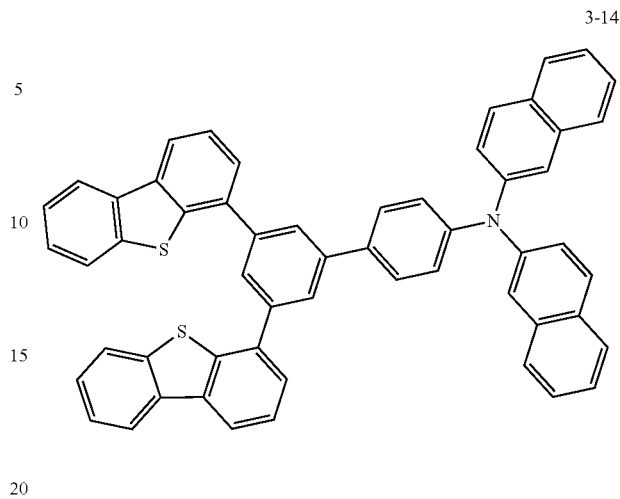
3-15
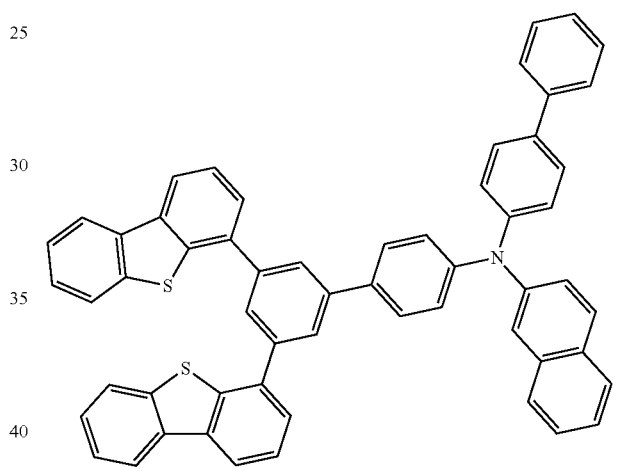
3-16
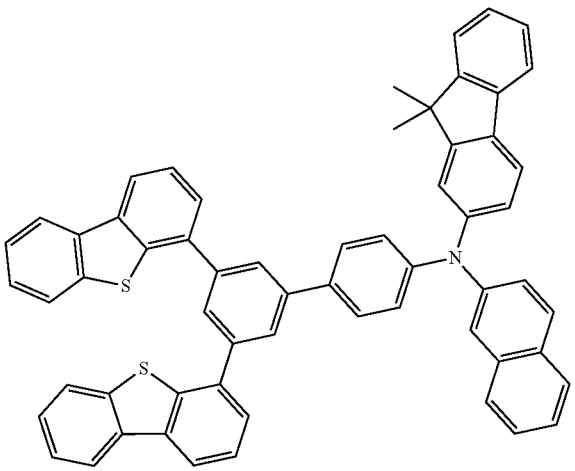

3-17
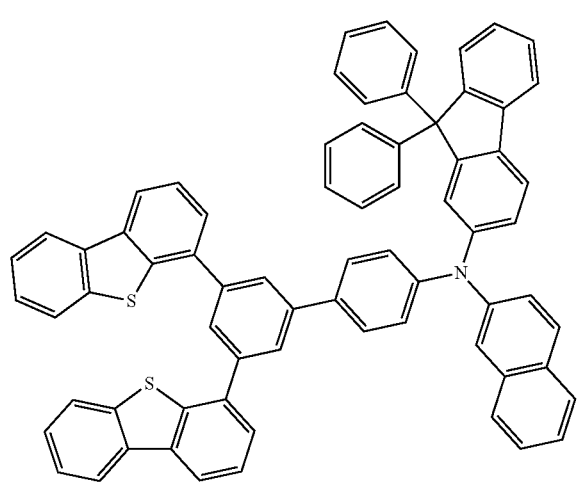
3-20
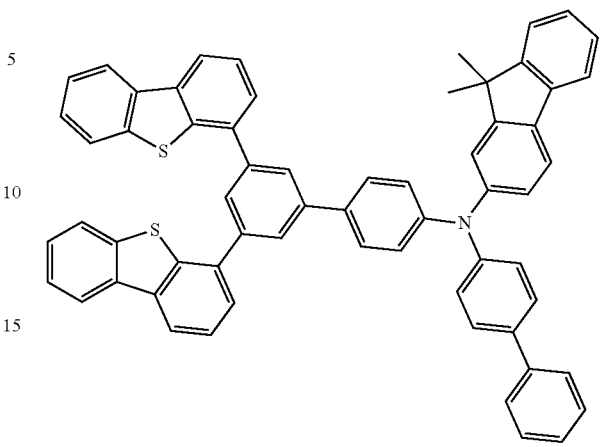
3-18
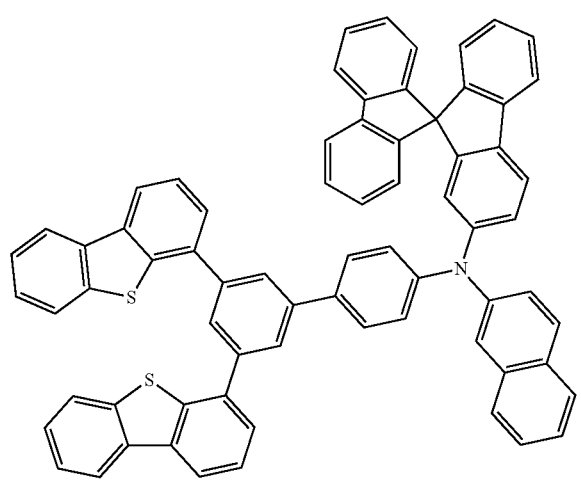
3-21
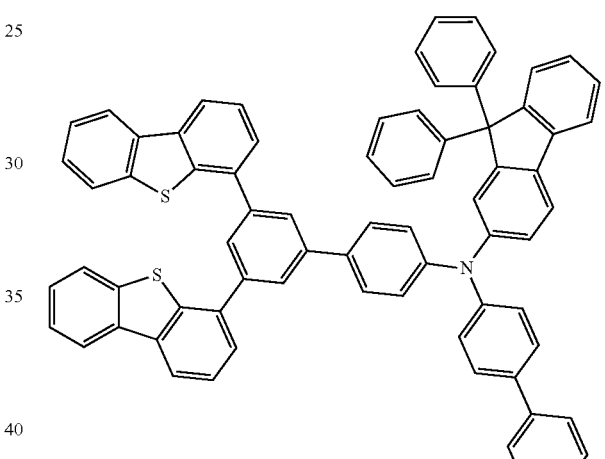
3-19
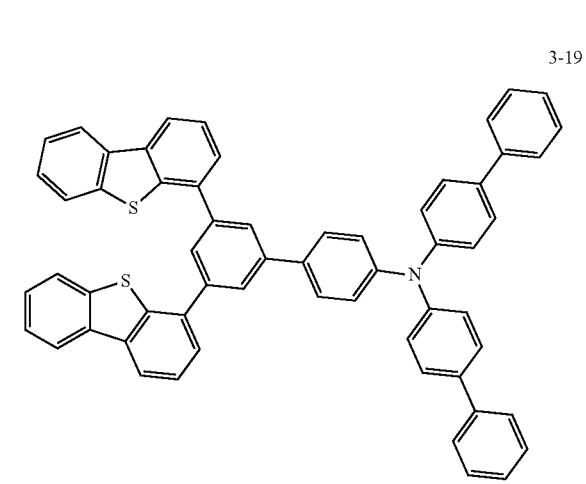
3-22
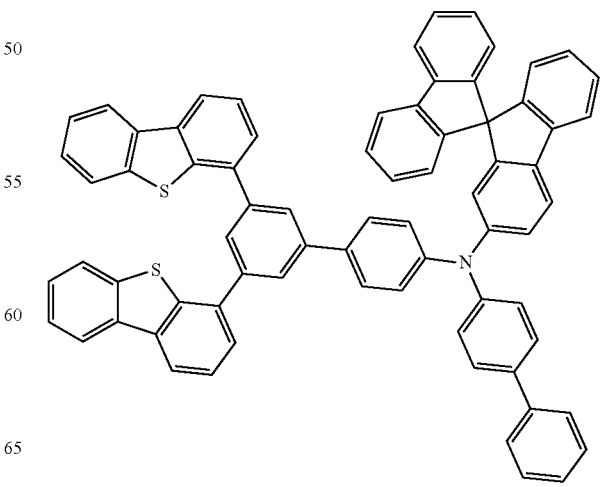

3-23
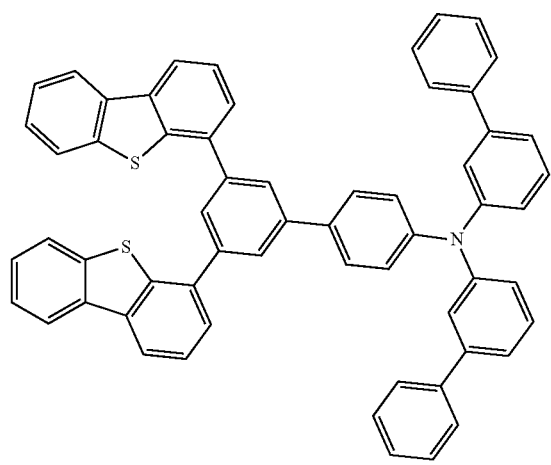
3-24
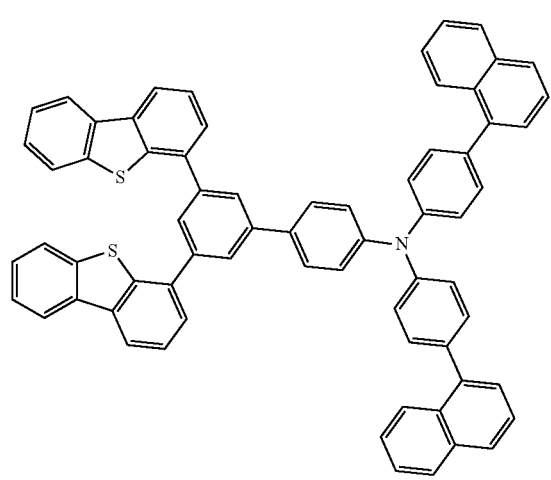
3-25
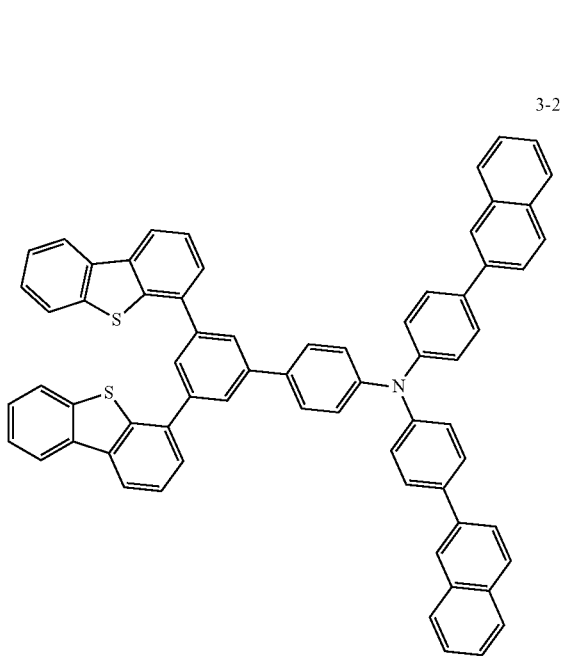
3-26
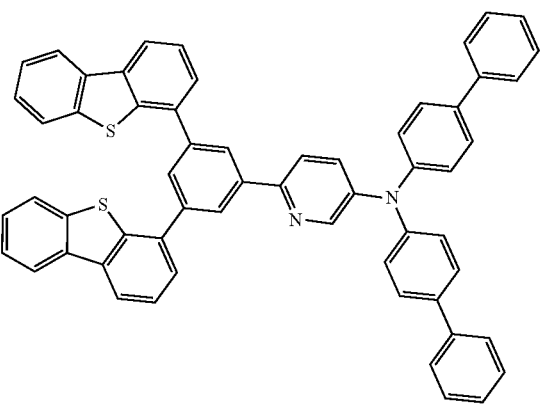
3-27
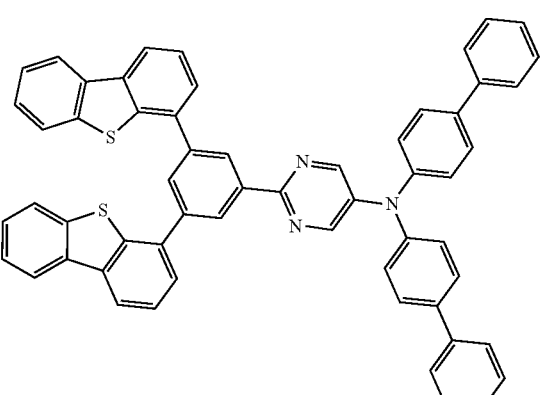
3-28
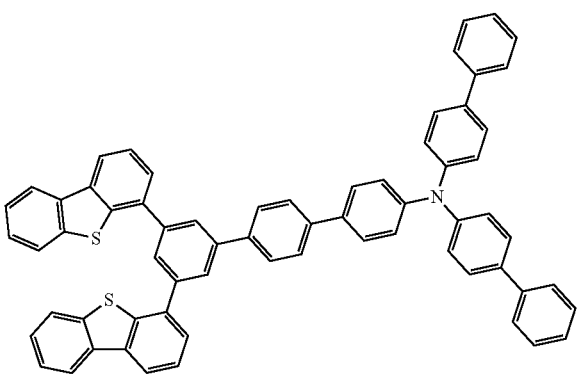
4-1
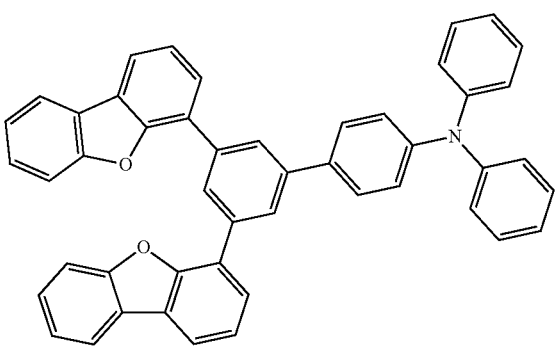

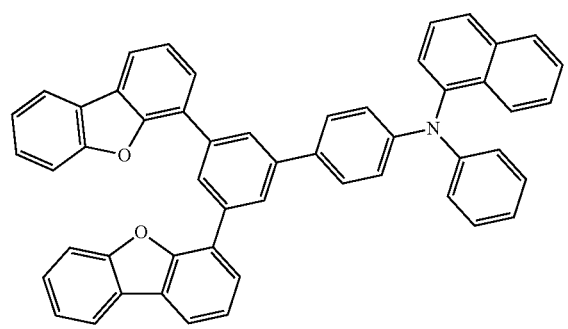
4-2
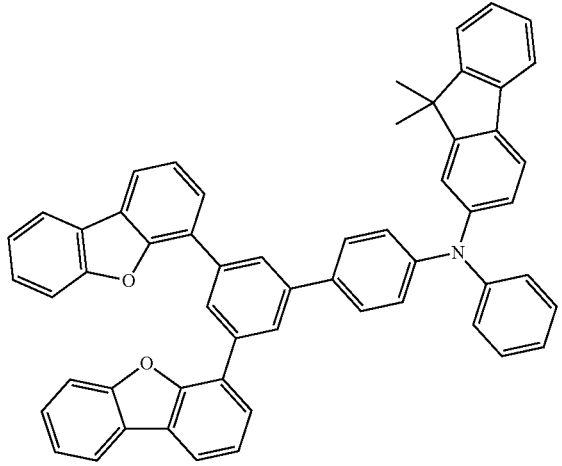
4-5
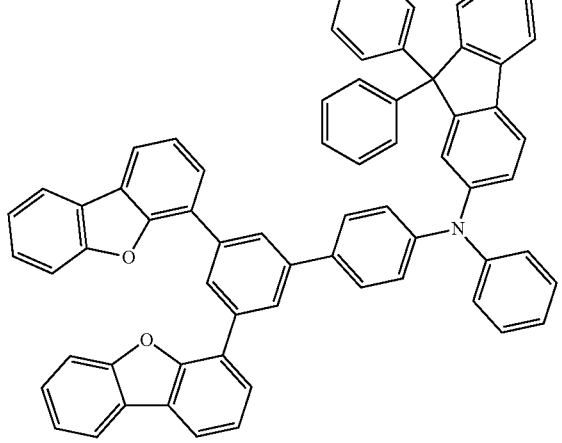
4-3
4-6
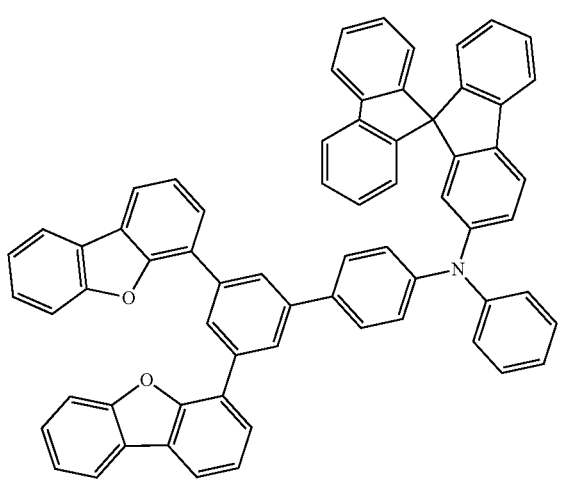
4-4
4-7

4-8
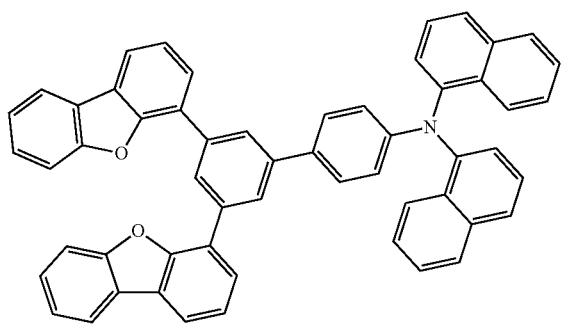
4-11
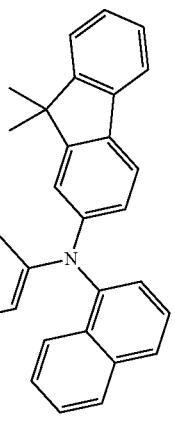
4-9
4-12
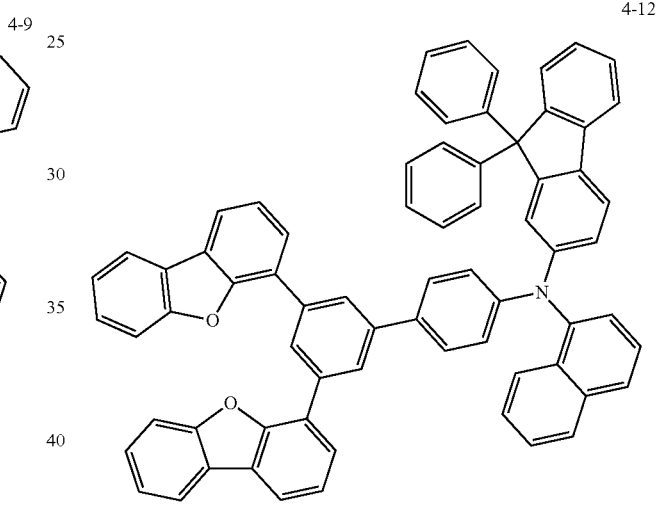
4-10
4-13
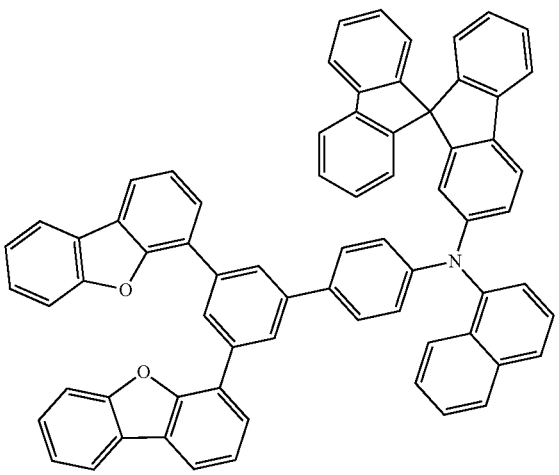

4-14
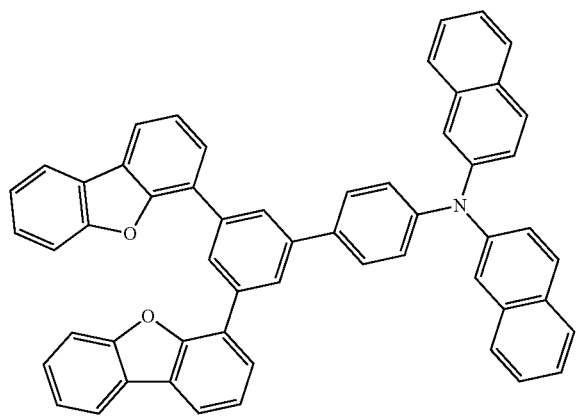
4-15
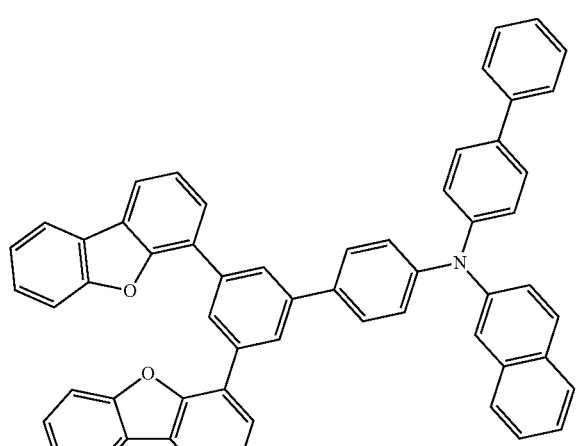
4-16
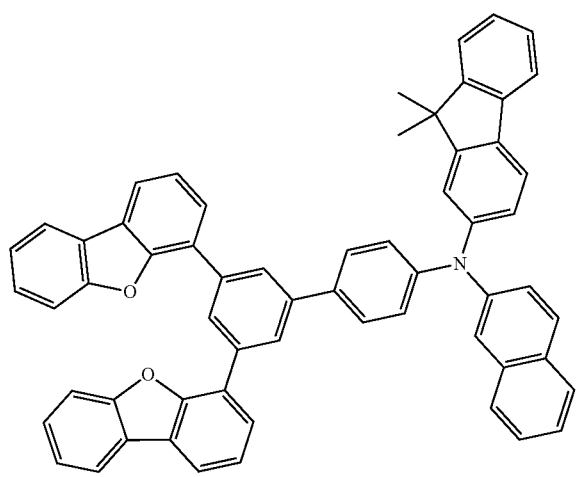
4-17
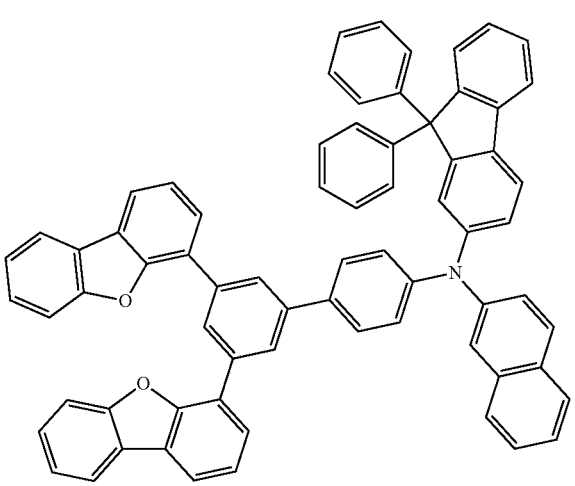
4-18
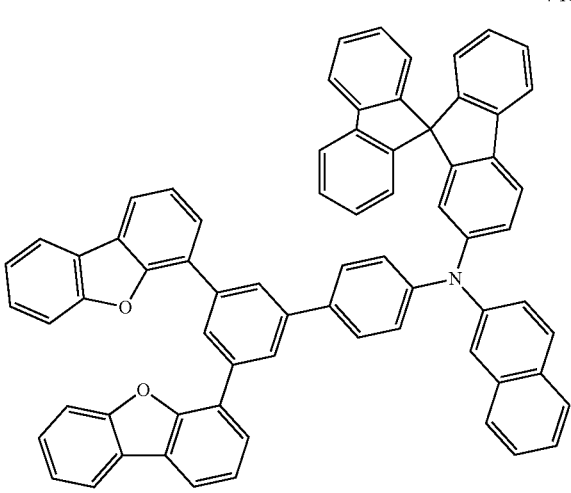
4-19
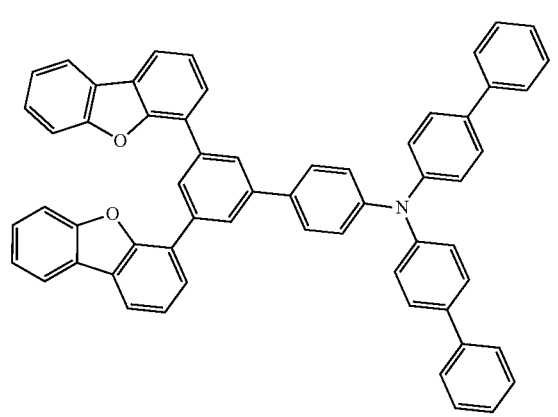

-continued
4-20
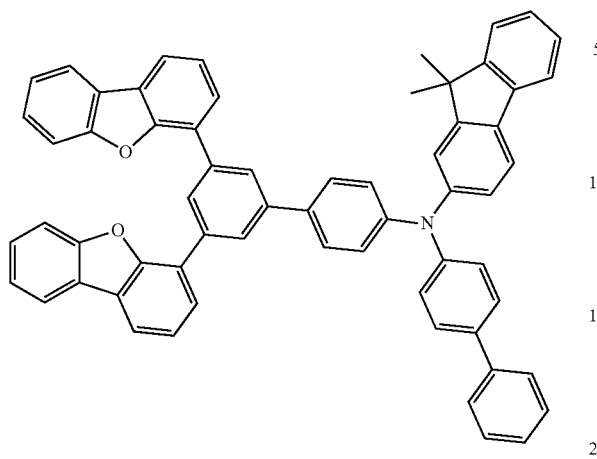
4-21
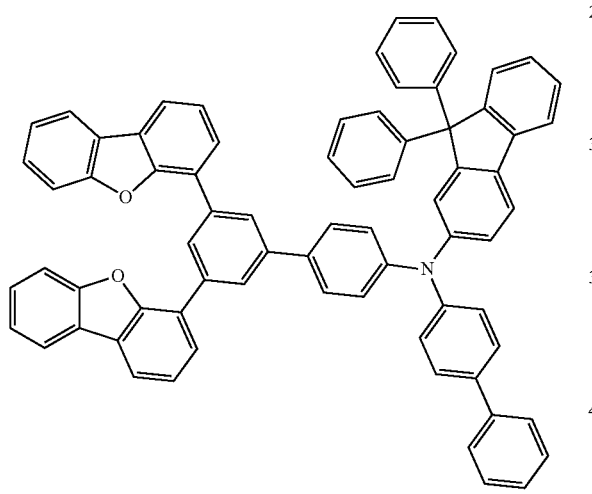
4-22
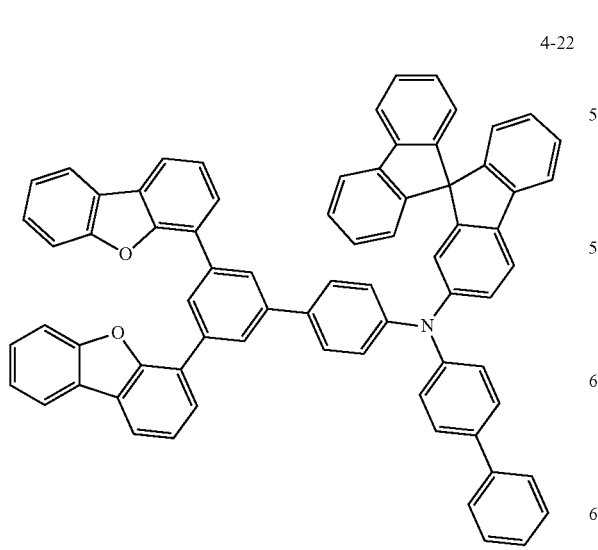
-continued
4-23
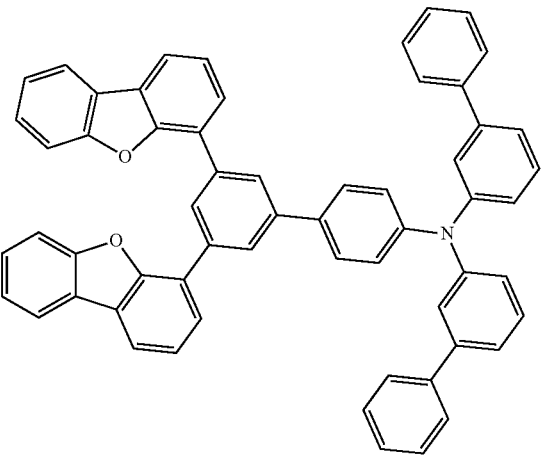
4-24
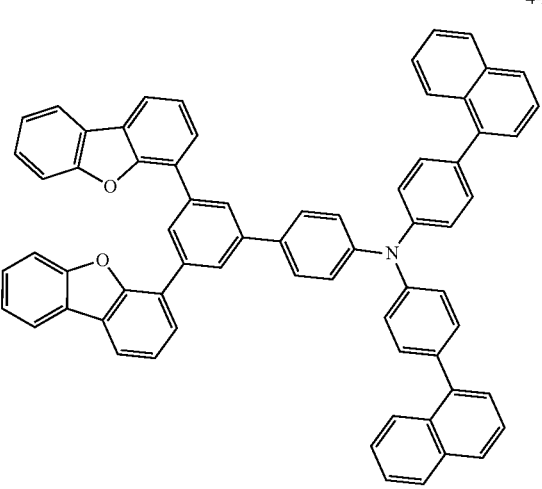
4-25
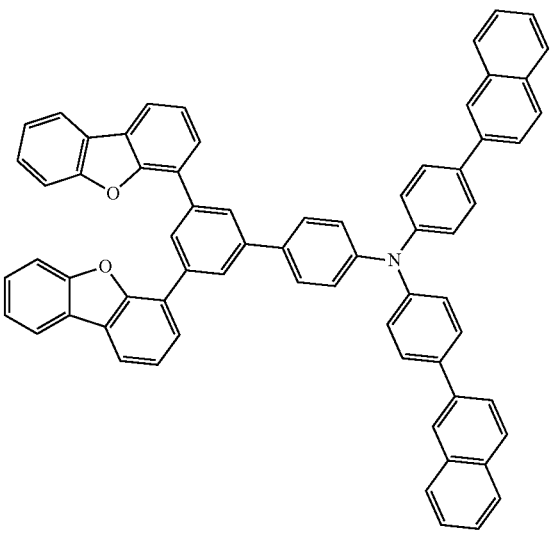

4-26
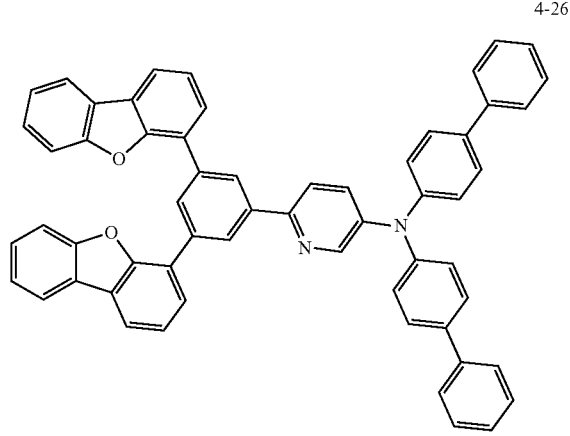
4-27
4-28
5-1
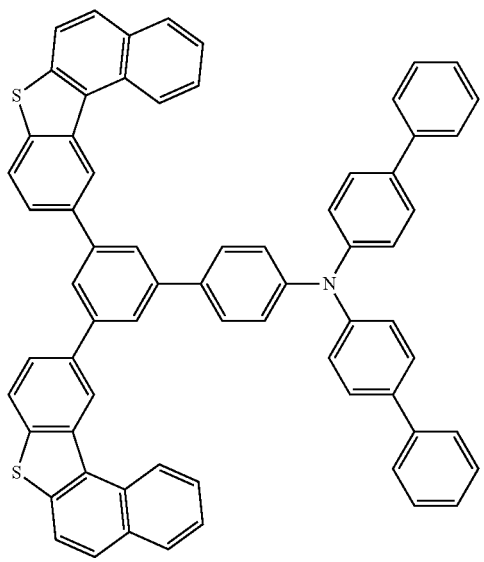
5-2
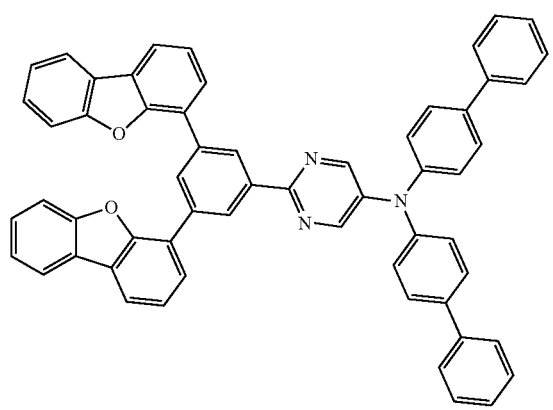
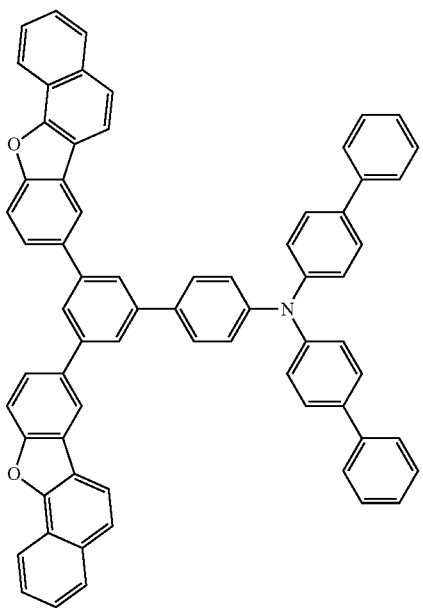

5-3
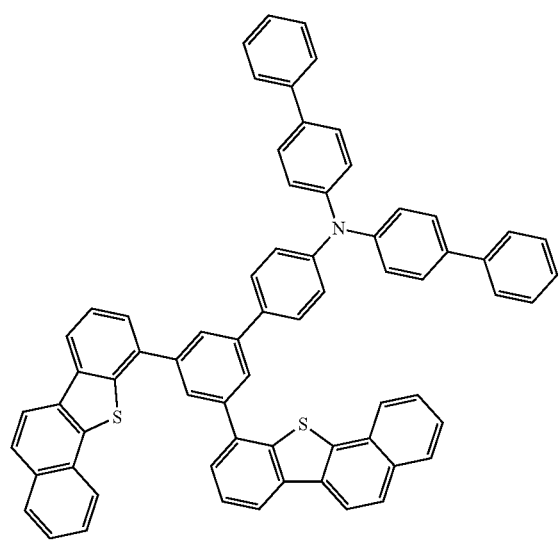
5-4
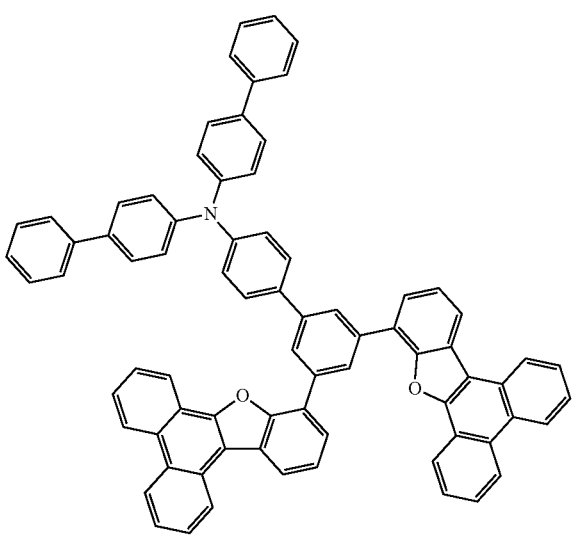
6-1
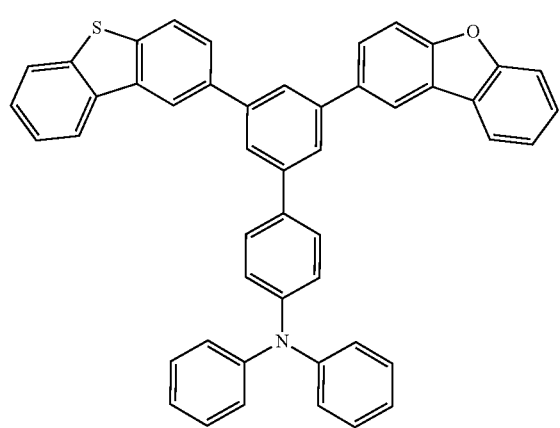
6-2
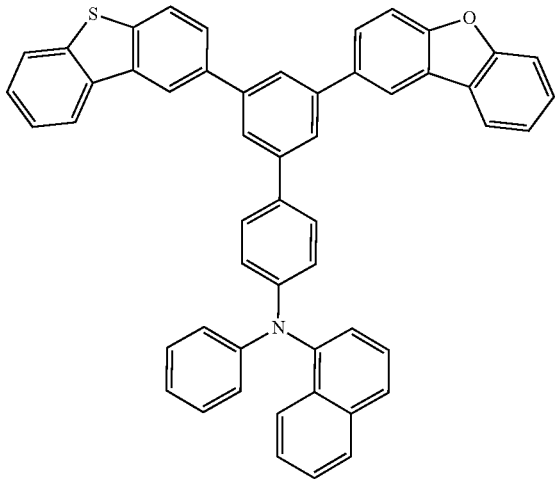
6-3
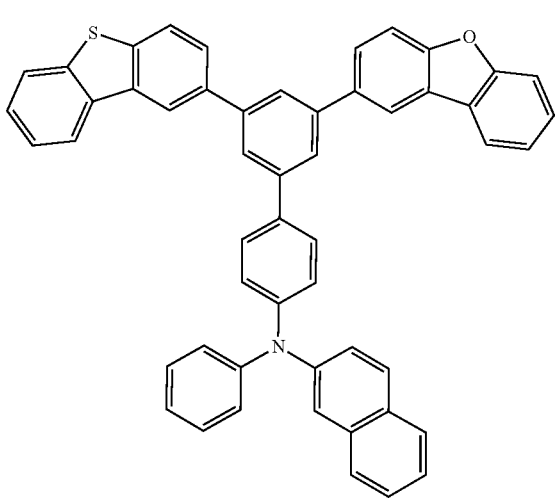
6-4
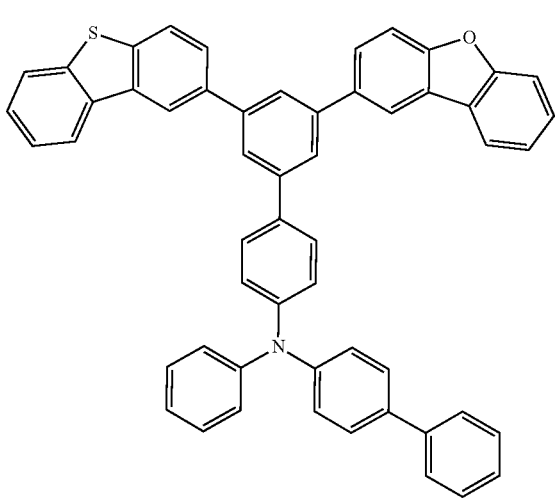

6-5
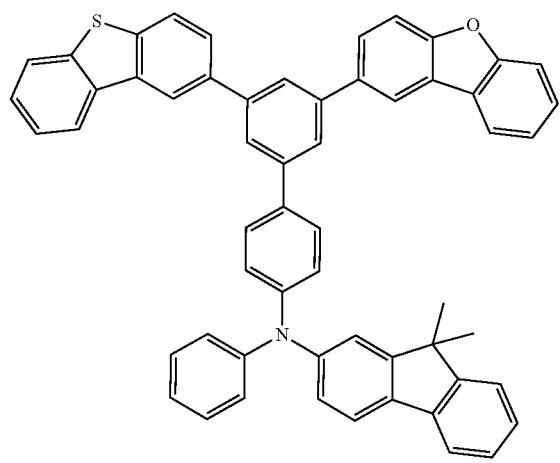
6-6
6-8
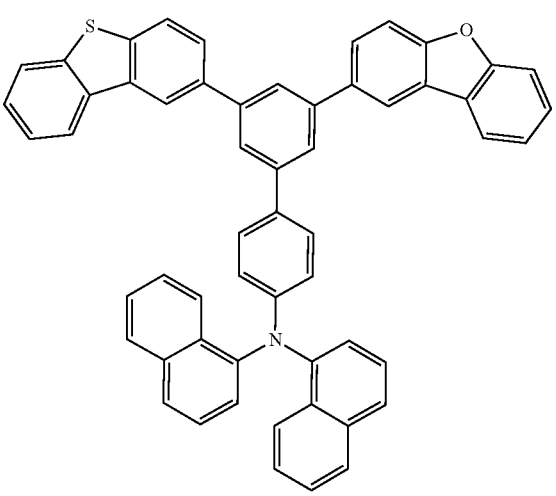
6-9
6-7
6-10
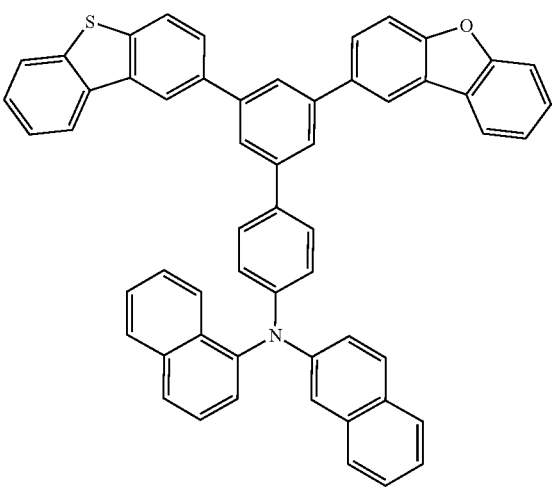
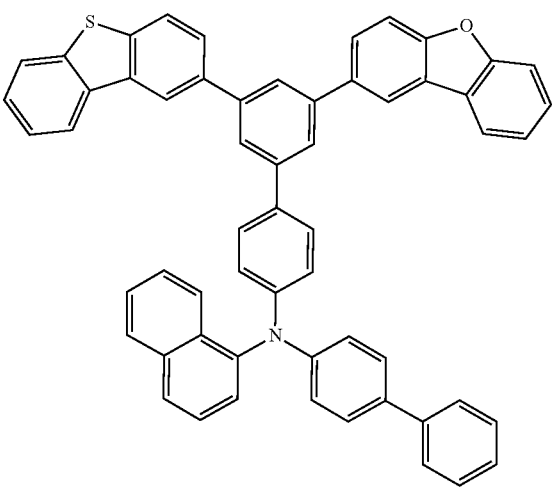

55
-continued
6-11
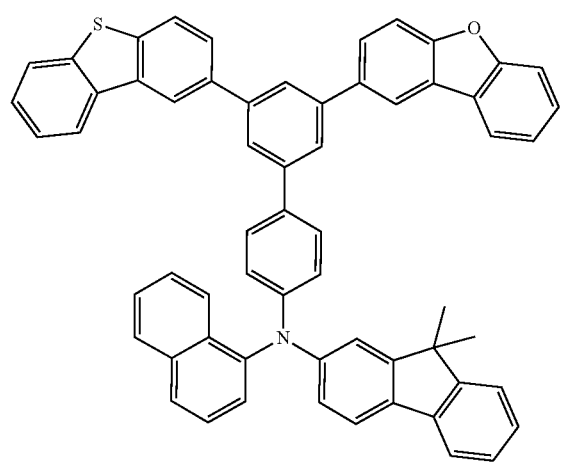
6-12
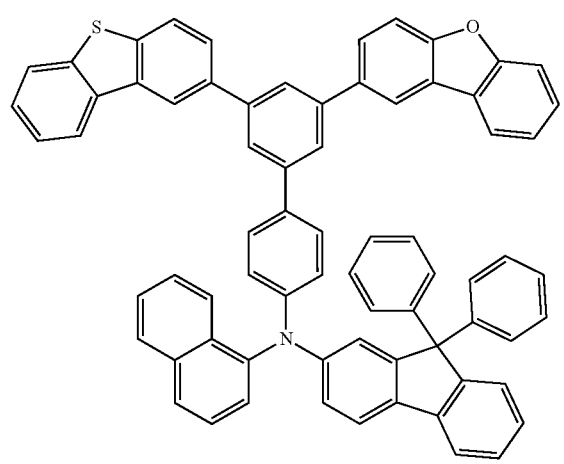
6-13
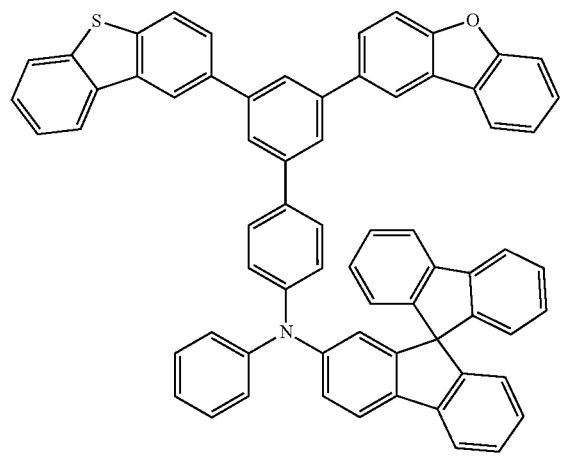
56
-continued
6-14
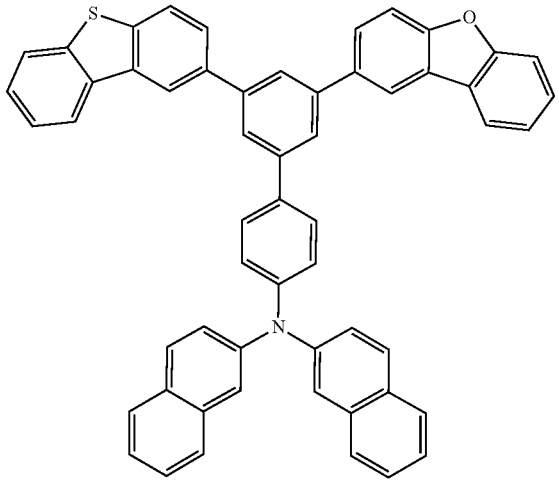
6-15
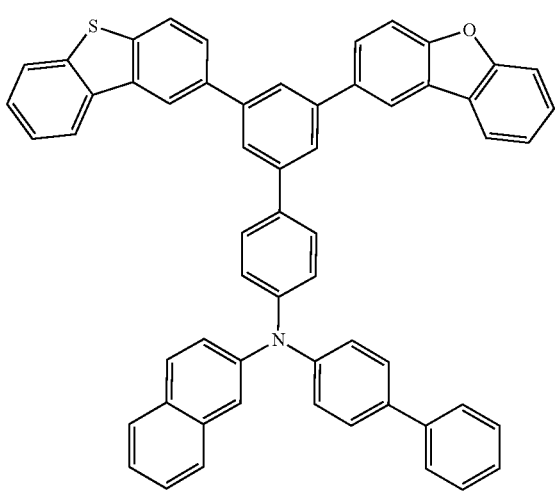
6-16
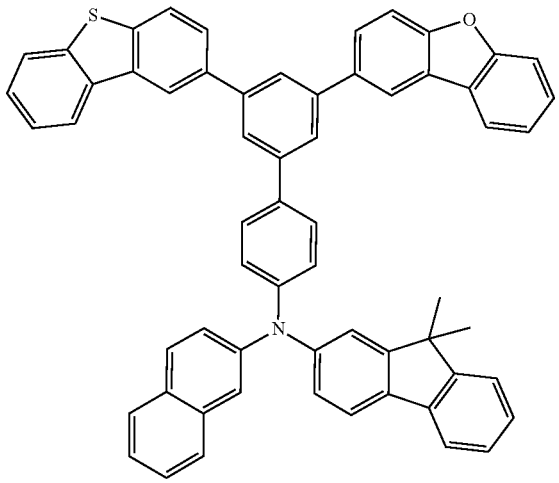

-continued
6-17
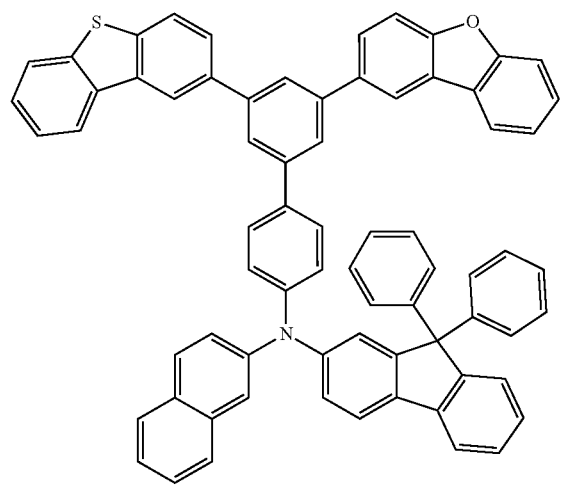
6-18
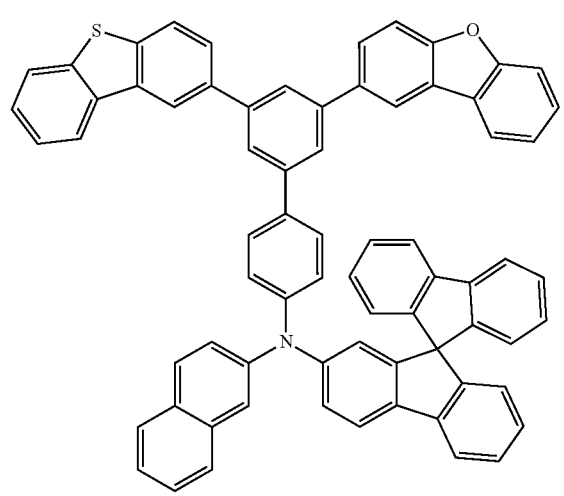
6-19
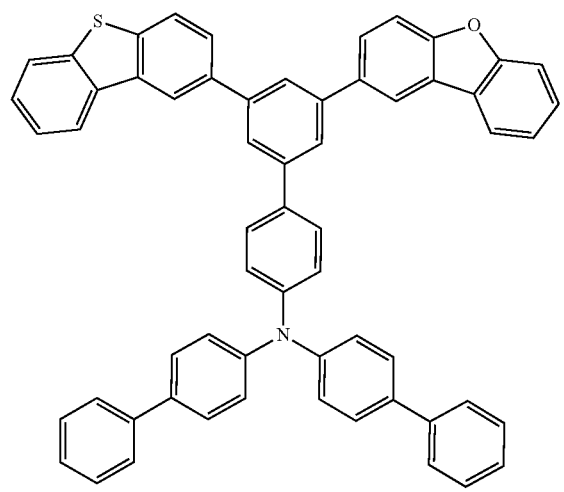
-continued
6-20
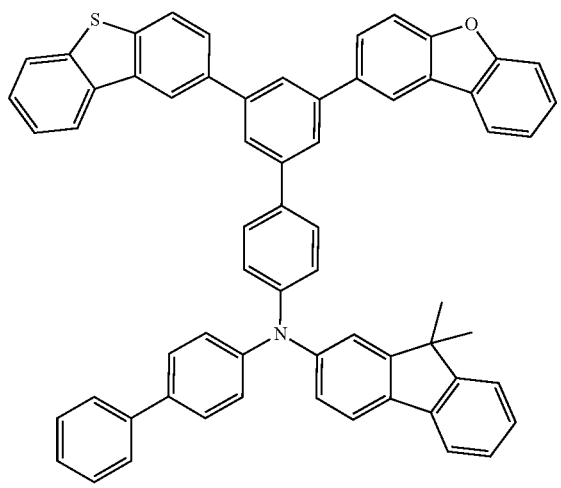
6-21
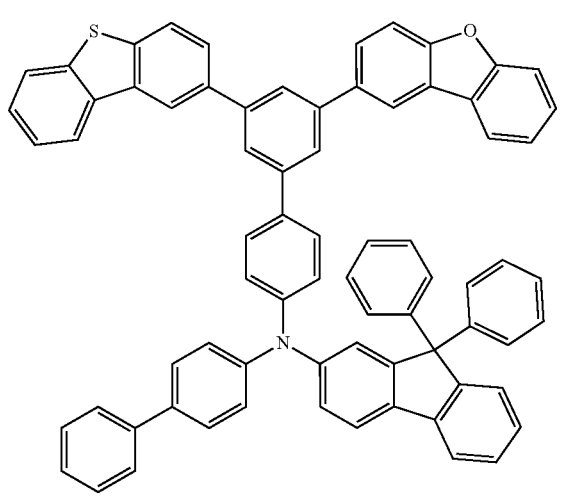
6-22
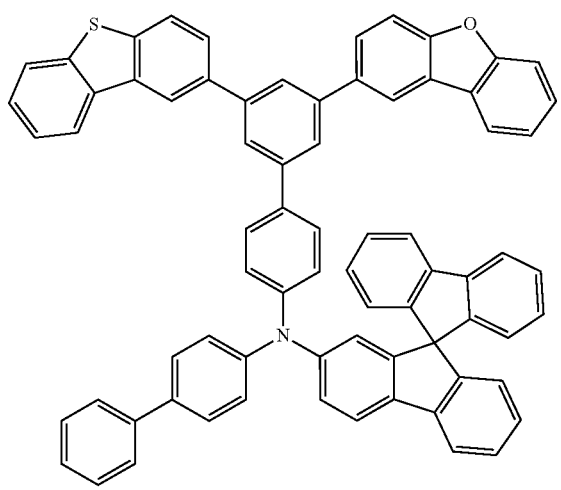

6-23
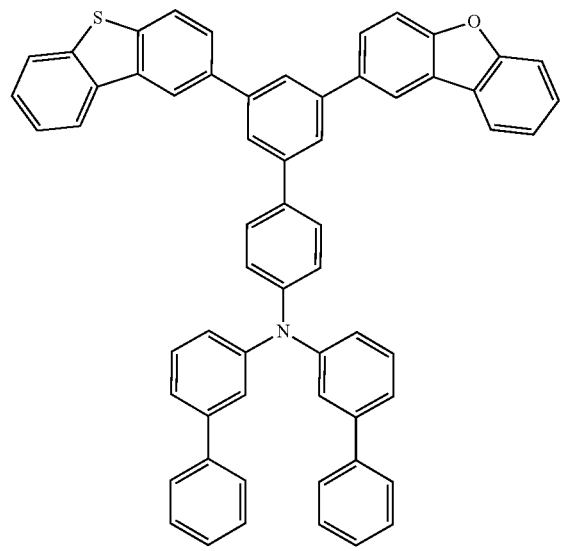
6-24
6-25
6-26
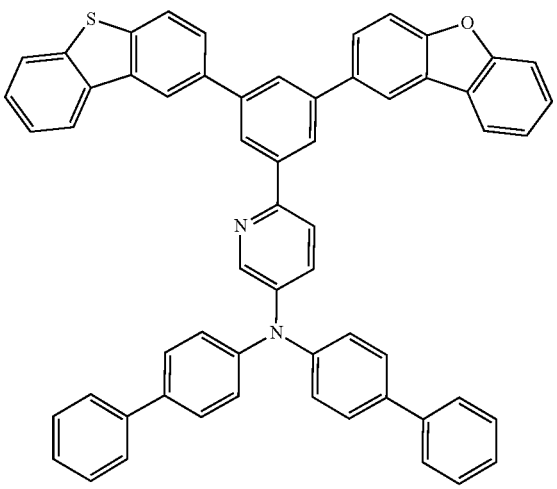
6-27
6-28
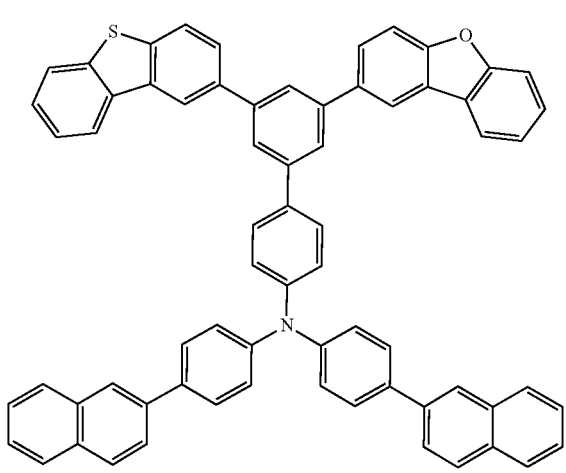
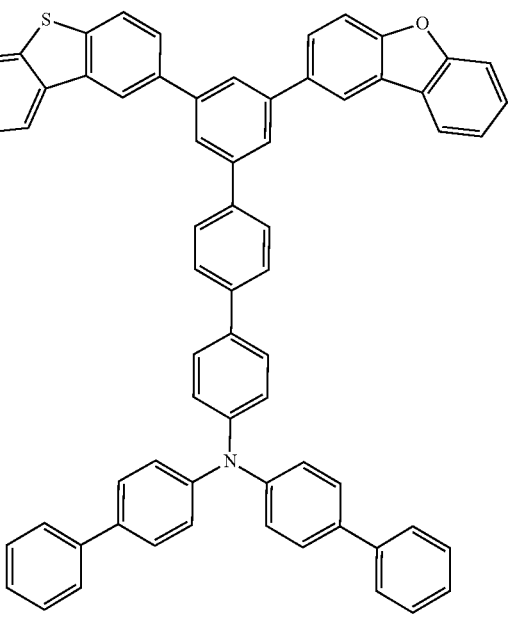

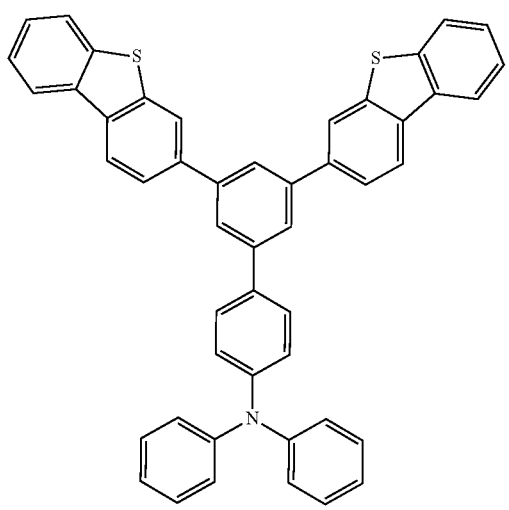
7-1
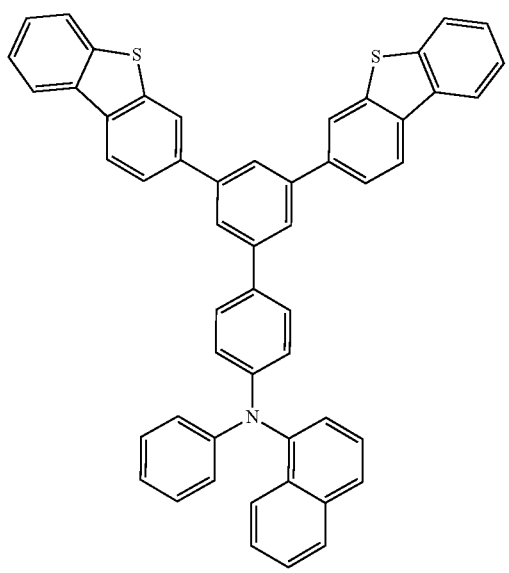
7-2
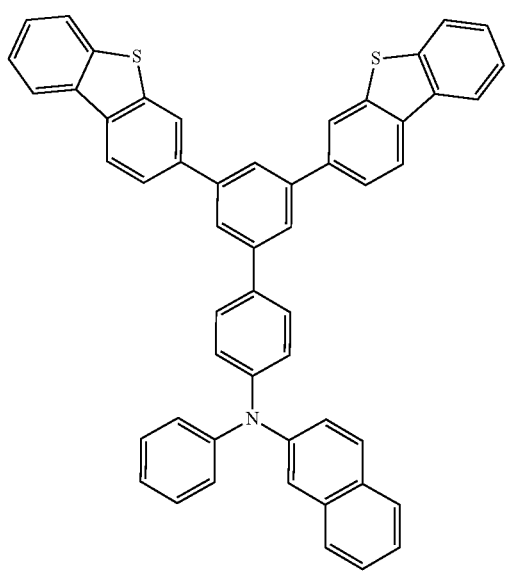
7-3
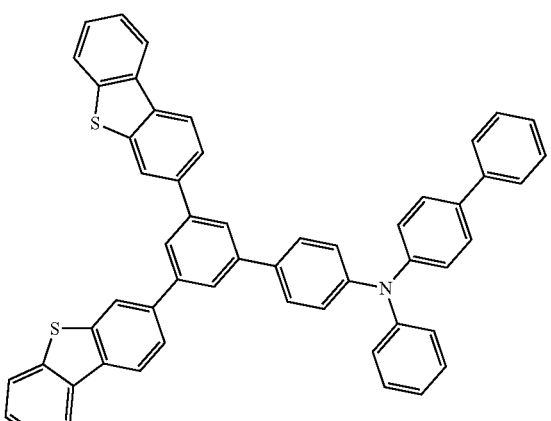
7-4
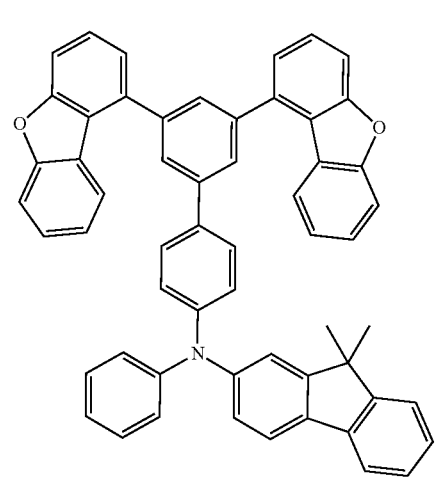
7-5
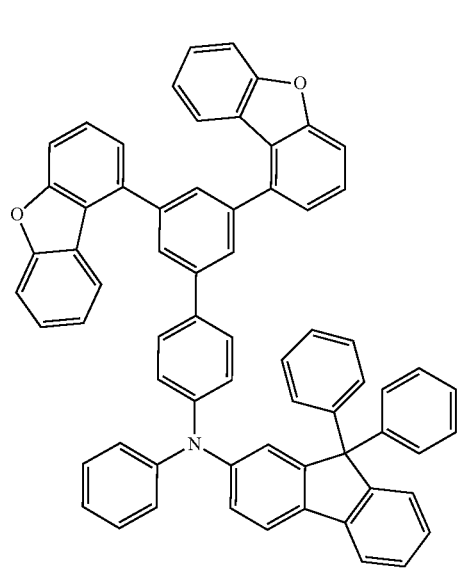
7-6

7-7
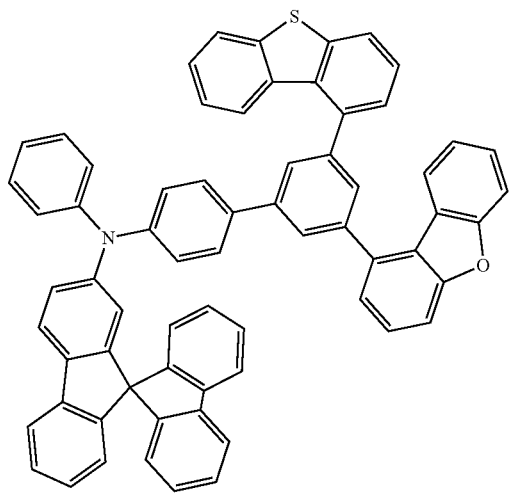
7-10
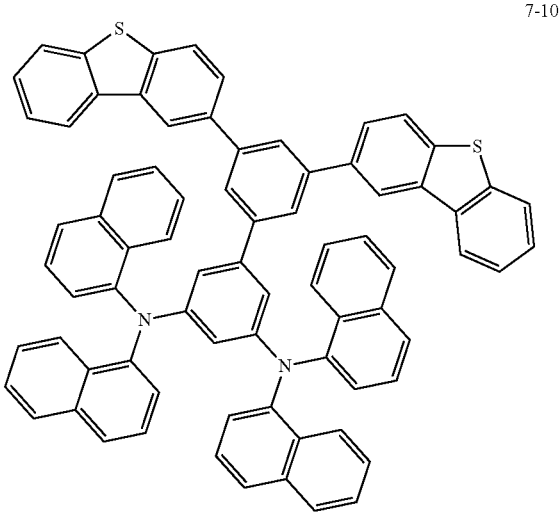
7-8
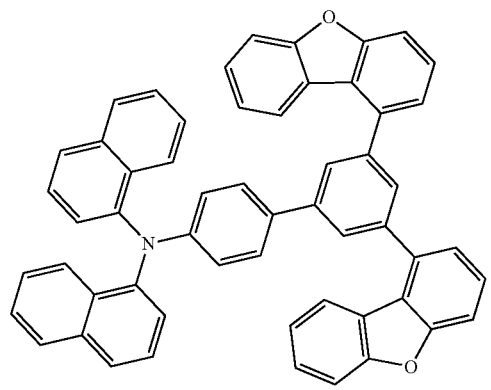
7-11
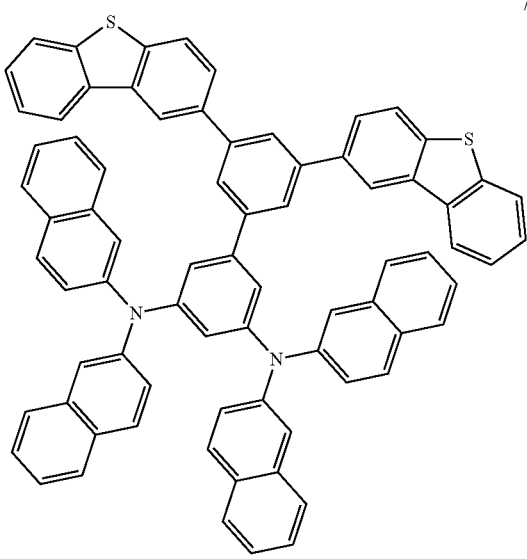
7-9
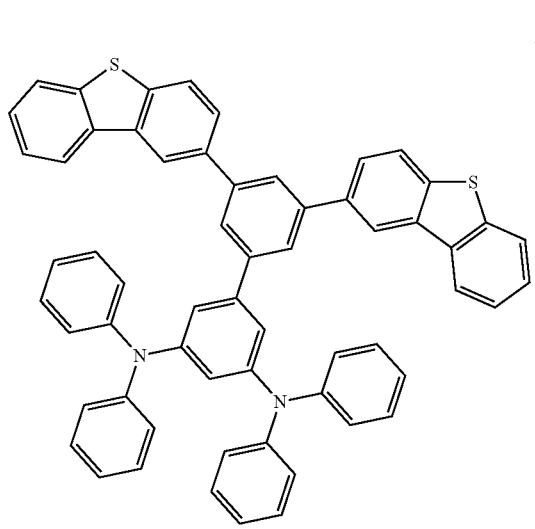
7-12
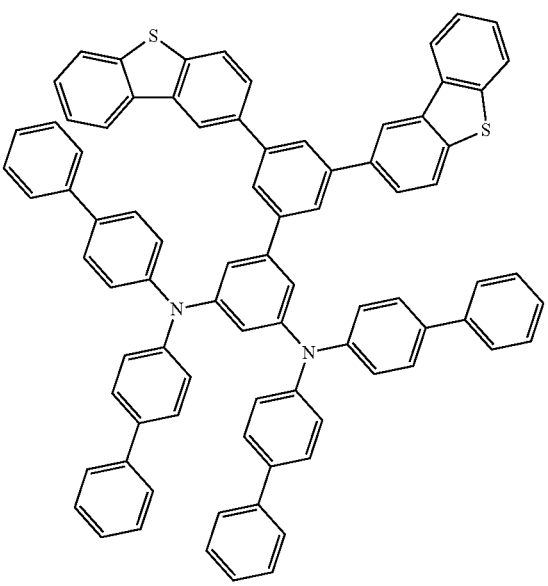

-continued
7-13
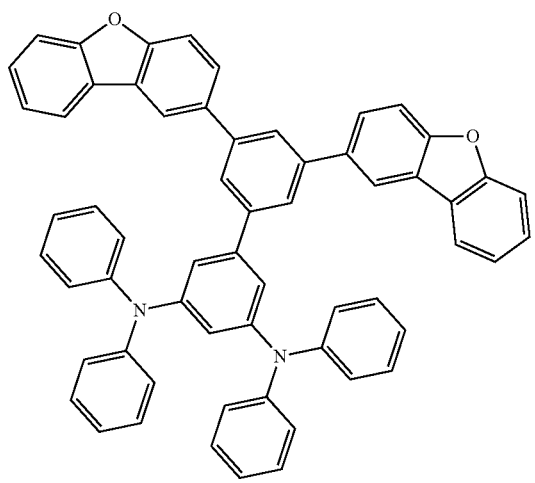
7-14
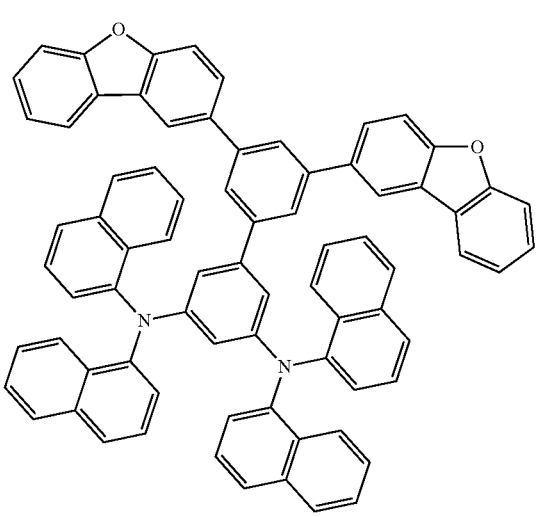
7-15
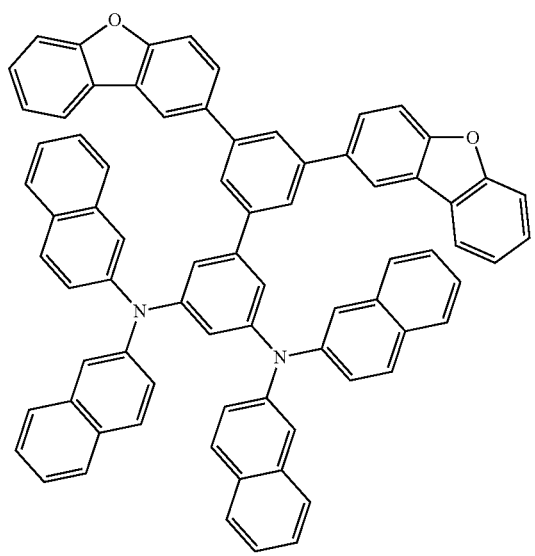
7-16
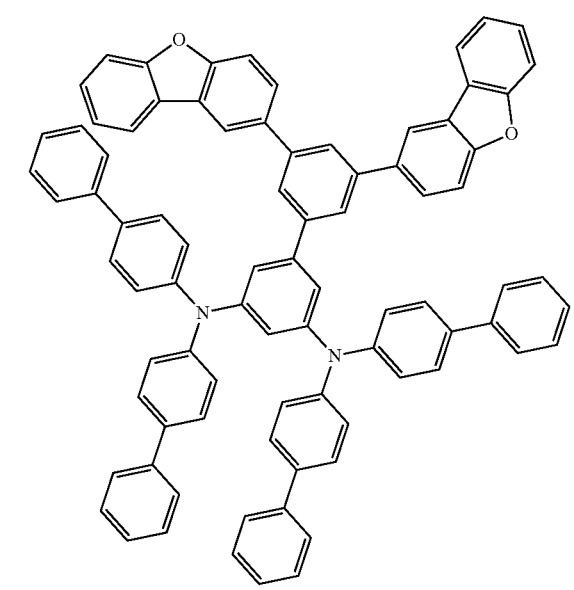
7-17
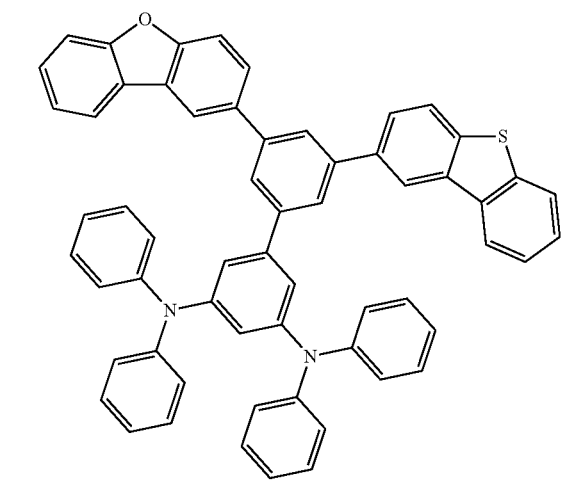
7-18
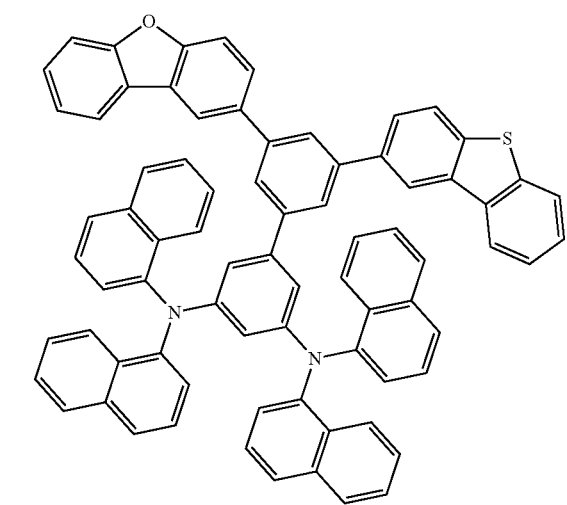

7-19
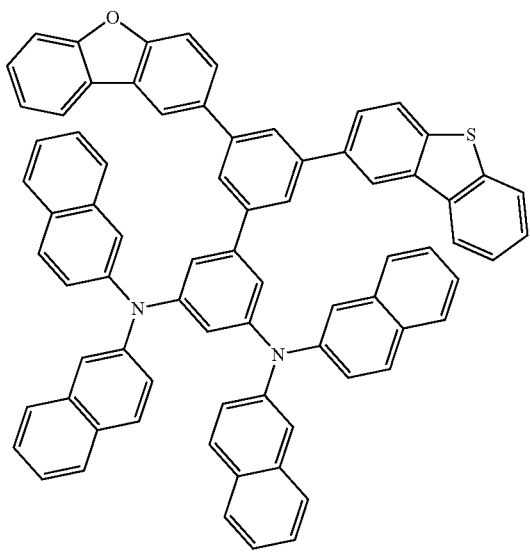
7-21
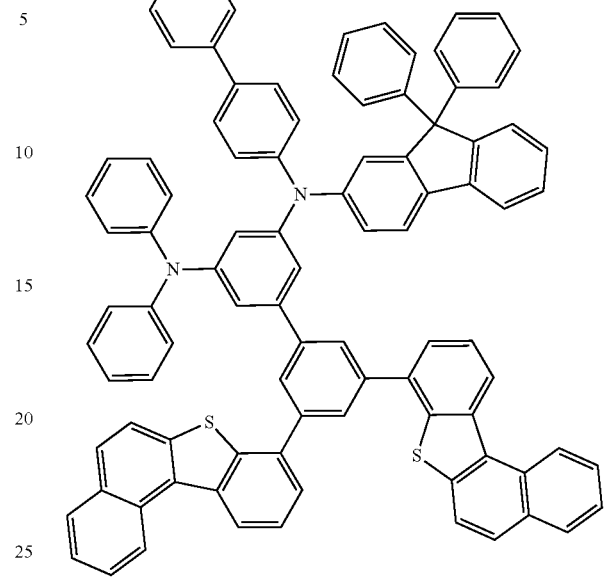
7-20
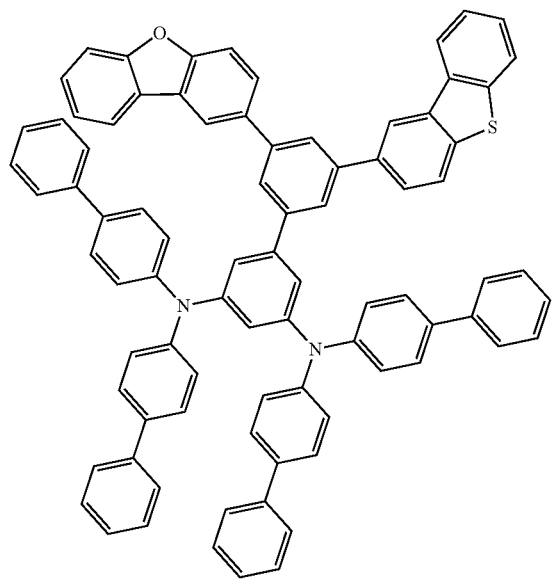
7-22
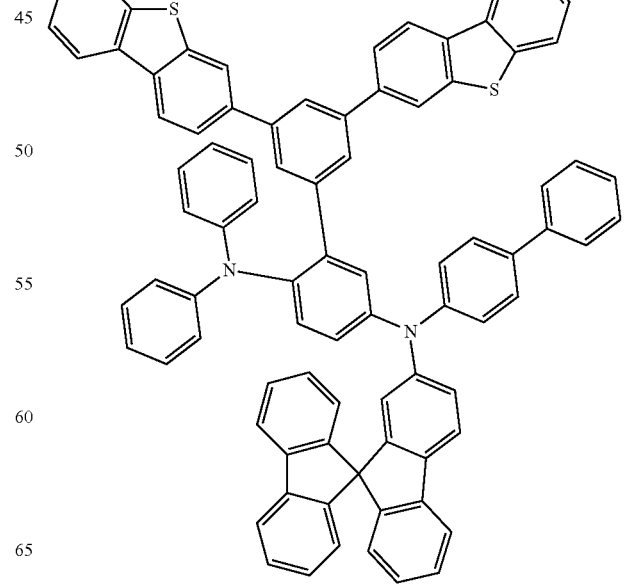

7-23

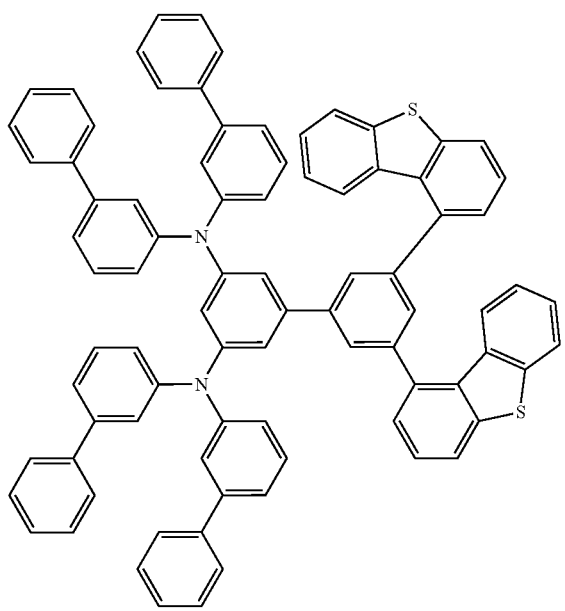

7-24

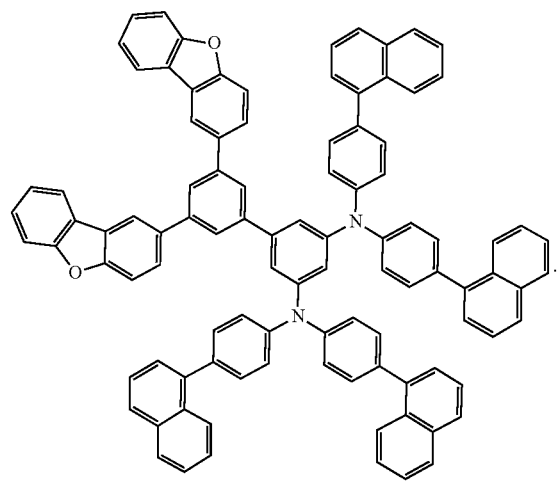

In another aspect of the present invention, there is provided an organic electric element comprising an organic material layer comprising at least one layer of a hole injection layer, a hole transport layer, or a light emitting layer comprising the compound represented by Formula 1.

Specifically, there is provided an organic electric element comprising the organic material layer comprising the compound represented by Formula 2 to Formula 7.

Specifically, there is provided an organic electric element comprising the organic material layer comprising one of the individual compounds.

Specifically, the compounds contained in the organic material layer may be the same kind or two or more different kind of compounds represented by Formula 1. For example, the hole transport layer above may be comprised by single compound 1-1, or comprised by a mixture of the compounds 1-1 and 1-2. Also, the emission auxiliary layer above may be comprised by single compound 1-1, or by a mixture of the compounds 1-1 and 1-2.

Meanwhile, the organic material layer above may be formed by any one of the process of spin coating, nozzle printing, inkjet printing, slot coating, dip coating and roll-to-roll.

In another aspect of the present invention, there is provided the organic electric element further including at least one layer to improve luminous efficiency which is formed on at least one of the sides the first and second electrodes, which is opposite to the organic material layer. Specifically, the layer to improve luminous efficiency above may comprise the compound represented by the Formula 1.

In another aspect of the present invention, there is provided an electronic device comprising a display device which comprises the organic electric element including the organic material layer containing the compound according to the invention, and a control unit for driving the display device. Here, the organic electric element may be one of an organic light emitting diode, an organic solar cell, an organic photo conductor, an organic transistor, and an element for monochromatic or white illumination.

Hereinafter, Synthesis Examples of the compounds represented by Formula 1 according to the present invention and Preparation Examples of an organic electric element will be described in detail by way of example. However, the following examples are only for illustrative purposes and are not intended to limit the scope of the invention.

SYNTHESIS EXAMPLE

I. Synthesis Example of Formula 1

The final product of the present invention represented by Formula 1 can be synthesized by reaction of Sub 1 and Sub 2 as illustrated in, but not limited to, the following Reaction Scheme 1.

<Reaction Scheme 1>

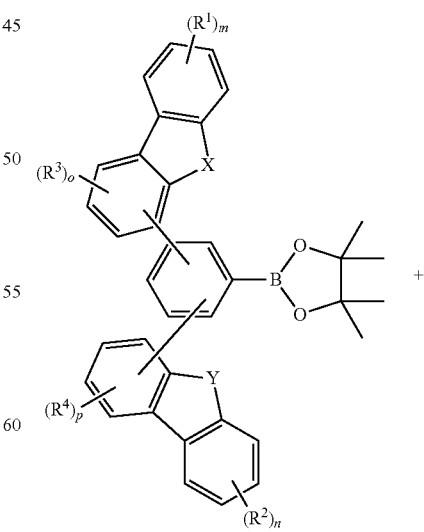

Sub 1

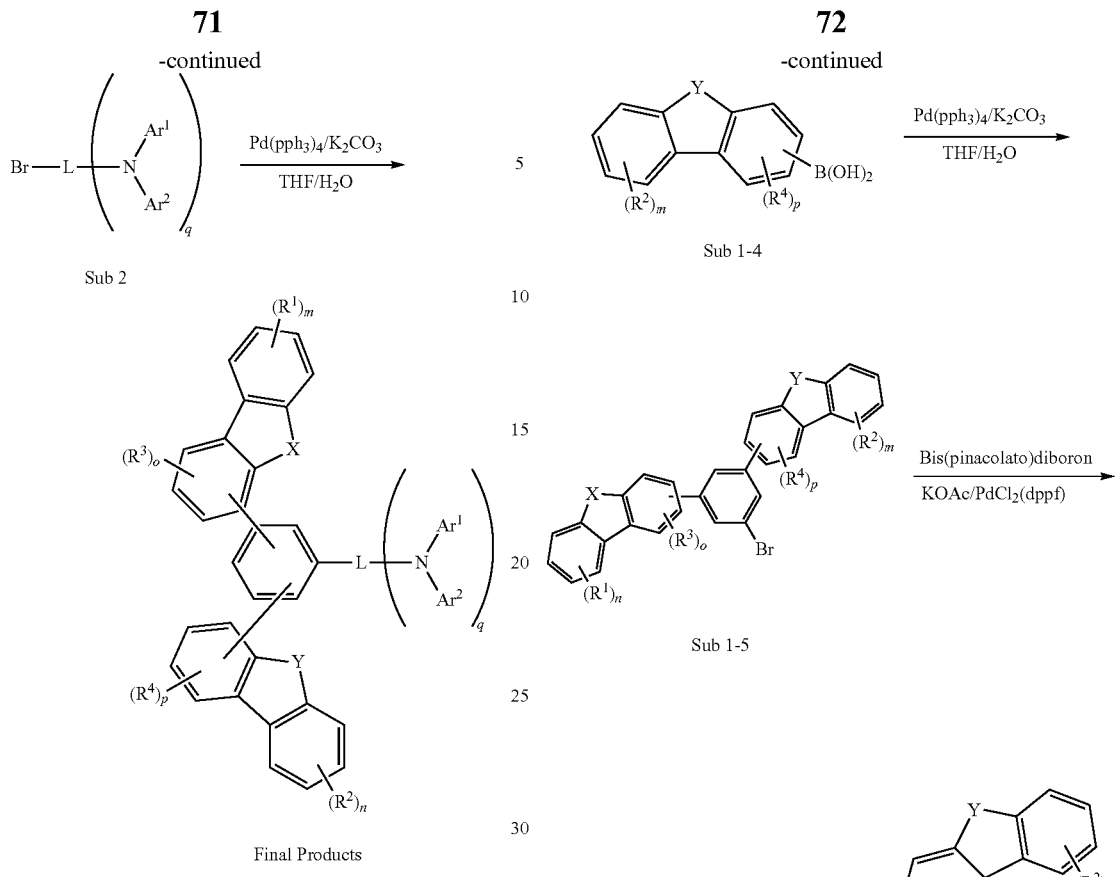
I. Synthesis Example of Sub 1
Sub 1 of the Reaction Scheme 1 can be synthesized according to, but not limited to, the following Reaction Scheme 2.
<Reaction Scheme 2>
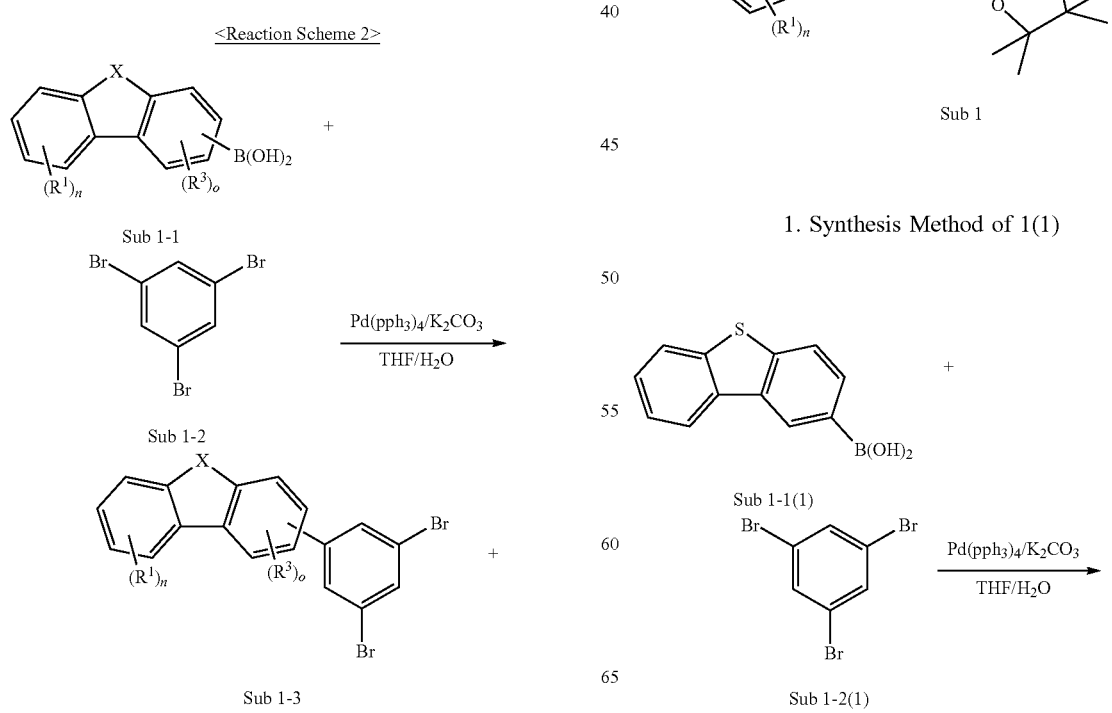
1. Synthesis Method of 1(1)

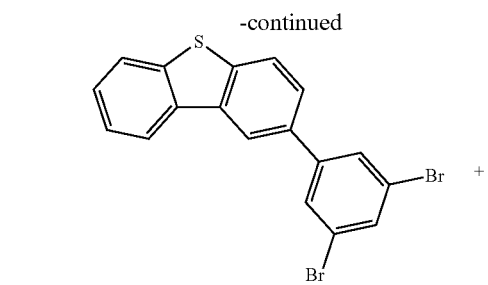
Sub 1-3(1)

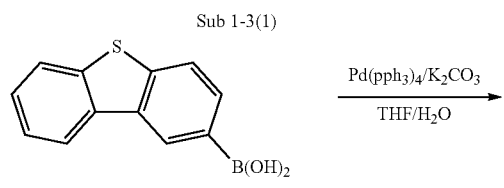
Sub 1-4(1)

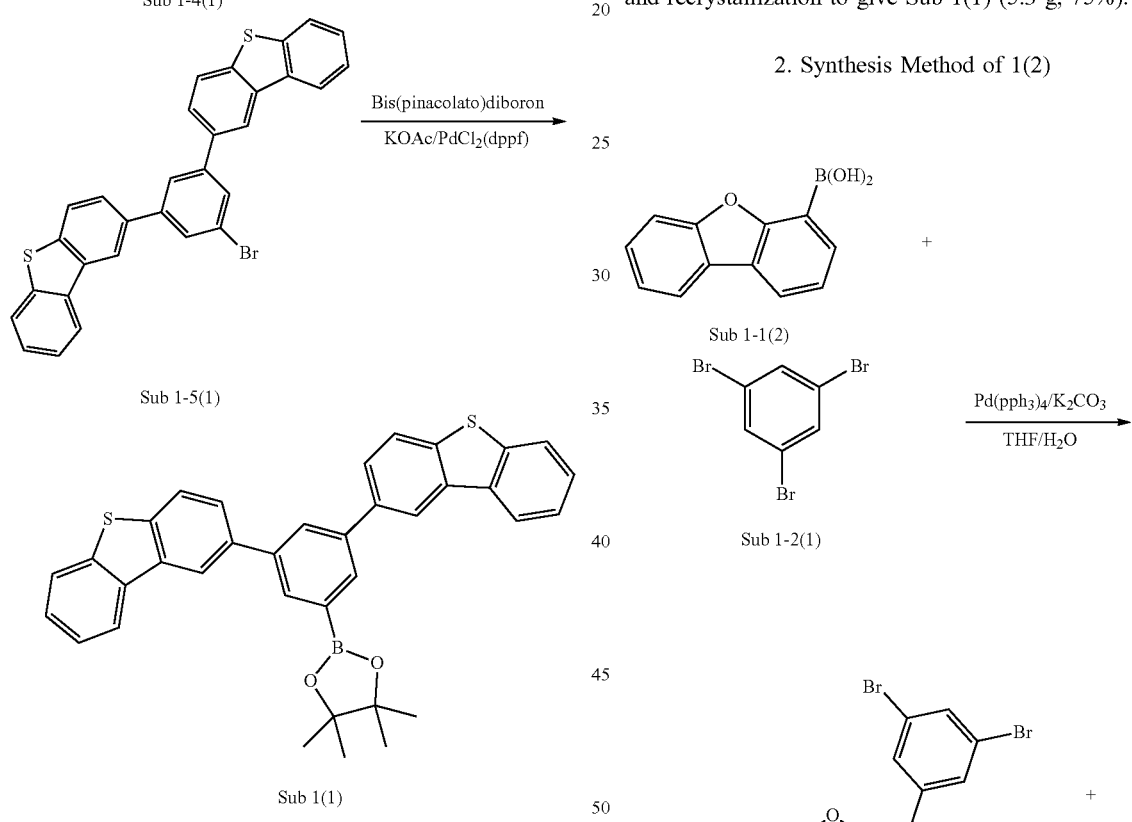

(1) Synthesis Method of Sub 1-3(1)

A mixture of Sub 1-1(1) (4.6 g, 20 mmol), Sub 1-2(1) (6.3 g, 20 mmol), Pd(PPh₃)₄ (0.07 g, 0.06 mmol), K₂CO₃ (8.3 g, 60 mmol) was dissolved in anhydrous THF and trace amount of water, and refluxed for 24 hr. After completion of the reaction, temperature of the reaction solution was cooled to room temperature, extracted with CH₂Cl₂ and washed with water, dried over MgSO₄, and filtered concentrated in vacuo. The crude product was purified by column chromatography to give Sub 1-3(1)(6.7 g, 80%).

(2) Synthesis Method of Sub 1-5(1)

A mixture of Sub 1-3(1) (6.7 g, 16 mmol), Sub 1-4(1) (3.6 g, 16 mmol), Pd(PPh₃)₄ (0.06 g, 0.05 mmol), K₂CO₃ (6.6 g, 48 mmol) was dissolved in anhydrous THF and trace amount of water, and refluxed for 24. After completion of the reaction, temperature of the reaction solution was cooled to room temperature, extracted with CH₂Cl₂, washed with water, dried over anhydrous MgSO₄, filtered and concentrated in vacuo. The crude product was purified by column chromatography to give Sub 1-5(1) (6.5 g, 78%).

(3) Synthesis Method of Sub 1(1)

To a solution of Sub 1-5(1) (6.5 g, 12.5 mmol) in DMF was added Bis(pinacolato)diboron (3.5 g, 13.8 mml), PdCl₂(dppf) (0.3 g, 0.4 mmol), KOAc (10.2 g, 36 mmol) and stirred at 90° C. After completion of the reaction, DMF was removed by distillation and extracted with CH₂Cl₂ and water. Organic phases were dried over MgSO₄, concentrated in vacuo. The crude product was purified silicagel column and recrystallization to give Sub 1(1) (5.3 g, 75%).

2. Synthesis Method of 1(2)

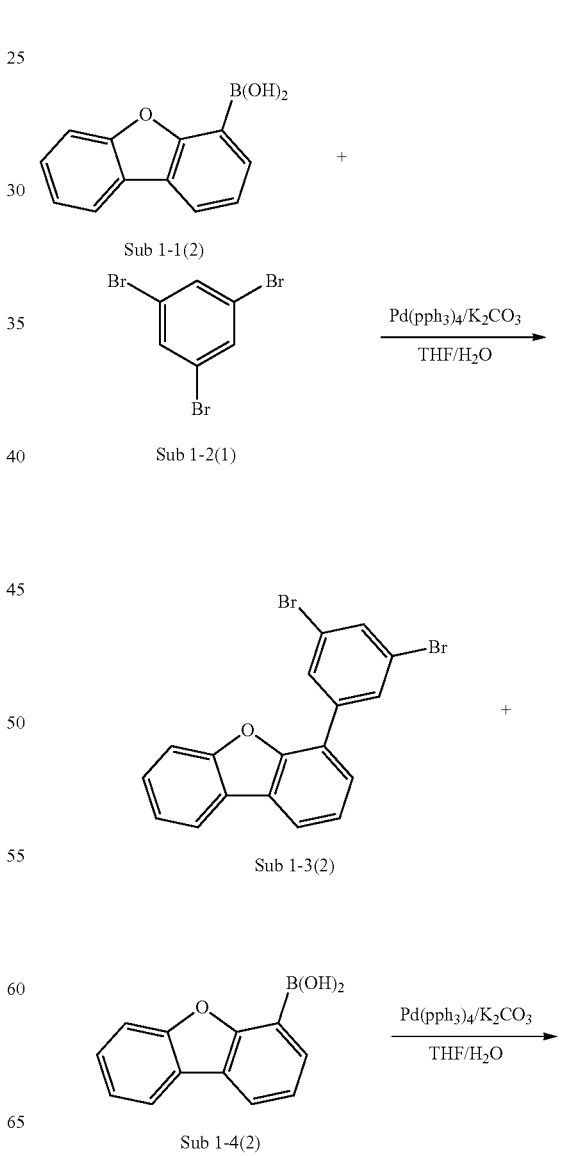

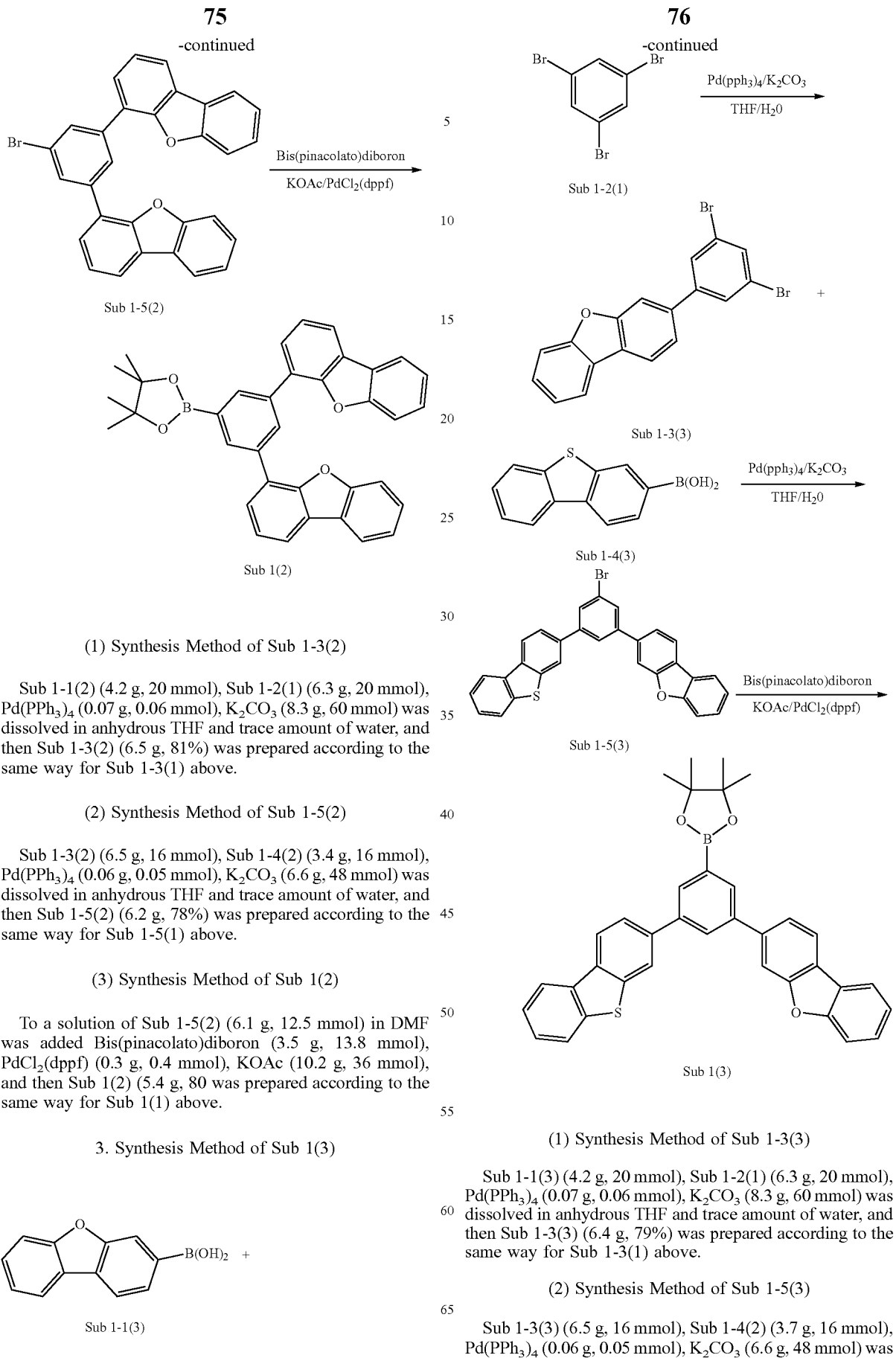

(1) Synthesis Method of Sub 1-3(2)

Sub 1-1(2) (4.2 g, 20 mmol), Sub 1-2(1) (6.3 g, 20 mmol), Pd(PPh$_3$)$_4$ (0.07 g, 0.06 mmol), K$_2$CO$_3$ (8.3 g, 60 mmol) was dissolved in anhydrous THF and trace amount of water, and then Sub 1-3(2) (6.5 g, 81%) was prepared according to the same way for Sub 1-3(1) above.

(2) Synthesis Method of Sub 1-5(2)

Sub 1-3(2) (6.5 g, 16 mmol), Sub 1-4(2) (3.4 g, 16 mmol), Pd(PPh$_3$)$_4$ (0.06 g, 0.05 mmol), K$_2$CO$_3$ (6.6 g, 48 mmol) was dissolved in anhydrous THF and trace amount of water, and then Sub 1-5(2) (6.2 g, 78%) was prepared according to the same way for Sub 1-5(1) above.

(3) Synthesis Method of Sub 1(2)

To a solution of Sub 1-5(2) (6.1 g, 12.5 mmol) in DMF was added Bis(pinacolato)diboron (3.5 g, 13.8 mmol), PdCl$_2$(dppf) (0.3 g, 0.4 mmol), KOAc (10.2 g, 36 mmol), and then Sub 1(2) (5.4 g, 80 was prepared according to the same way for Sub 1(1) above.

3. Synthesis Method of Sub 1(3)

(1) Synthesis Method of Sub 1-3(3)

Sub 1-1(3) (4.2 g, 20 mmol), Sub 1-2(1) (6.3 g, 20 mmol), Pd(PPh$_3$)$_4$ (0.07 g, 0.06 mmol), K$_2$CO$_3$ (8.3 g, 60 mmol) was dissolved in anhydrous THF and trace amount of water, and then Sub 1-3(3) (6.4 g, 79%) was prepared according to the same way for Sub 1-3(1) above.

(2) Synthesis Method of Sub 1-5(3)

Sub 1-3(3) (6.5 g, 16 mmol), Sub 1-4(2) (3.7 g, 16 mmol), Pd(PPh$_3$)$_4$ (0.06 g, 0.05 mmol), K$_2$CO$_3$ (6.6 g, 48 mmol) was dissolved in in anhydrous THF and trace amount of water, and then Sub 1-5(3) (6.5 g, 80%) was prepared according to the same way for Sub 1-5(1).

(3) Synthesis Method of Sub 1(3)

To a solution of Sub 1-5(3) (6.3 g, 12.5 mmol) in DMF was added Bis(pinacolato)diboron (3.5 g, 13.8 mmol), PdCl$_2$(dppf) (0.3 g, 0.4 mmol), KOAc (10.2 g, 36 mmol), and then Sub 1(3)(5.7 g, 82%) was prepared according to the same way for Sub 1(1).

Examples of Sub 1 compounds include, but are not limited to, the following compounds, and FD-MS(Field Desorption-Mass Spectrometry) data of the compounds are given in Table 1 below.

TABLE 1

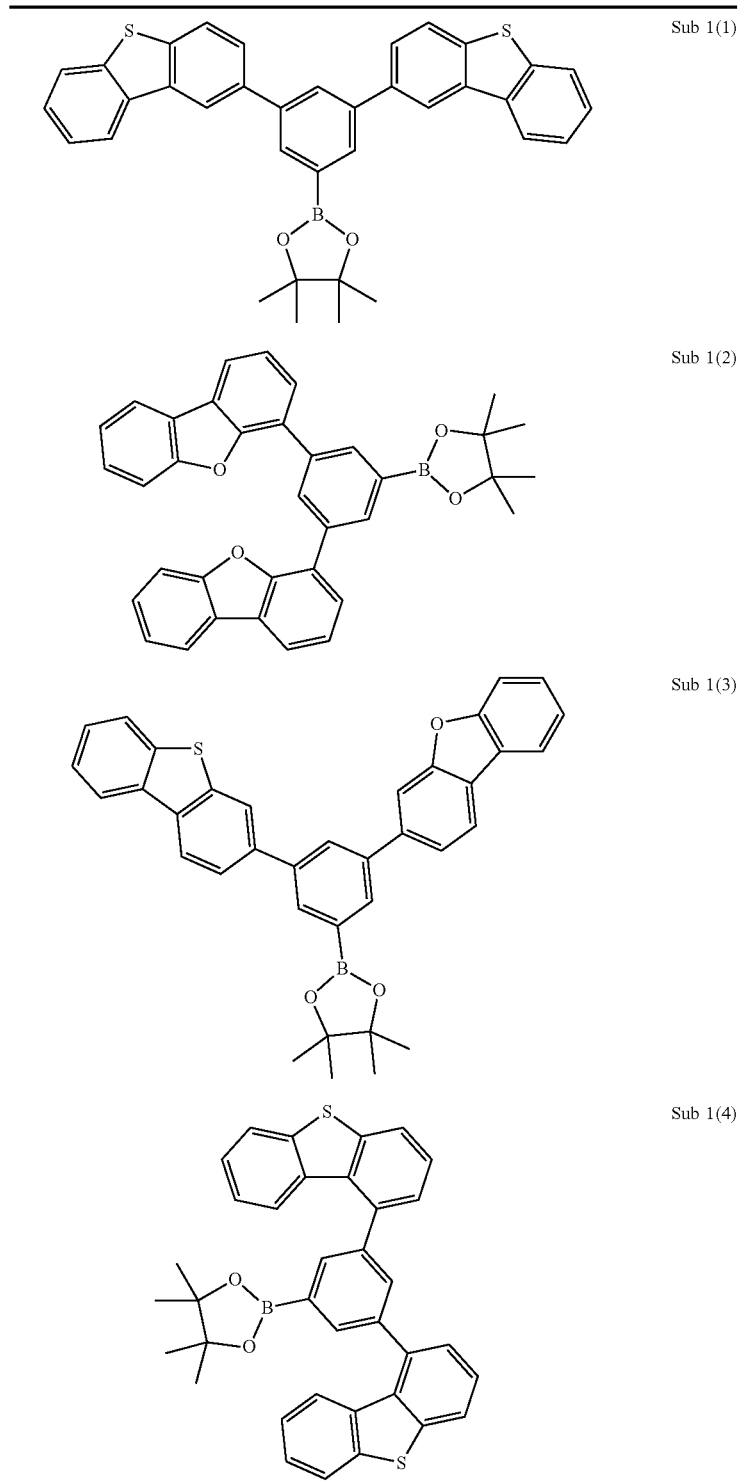

TABLE 1-continued
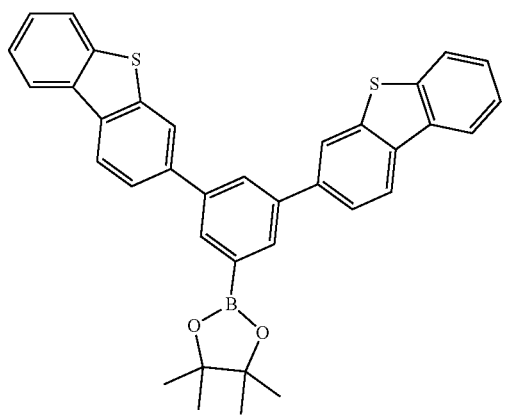 [SMILES: CC1(C)OB(c2cc(-c3ccc4c(c3)sc3ccccc34)cc(-c3ccc4c(c3)sc3ccccc34)c2)OC1(C)C]
Sub 1(5)
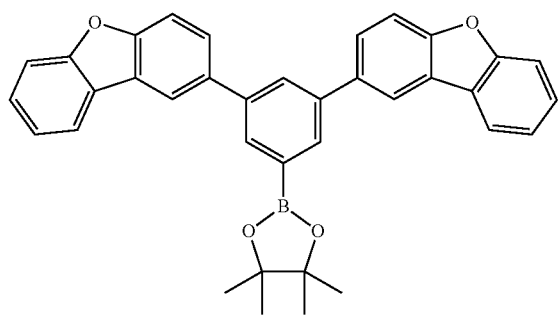 [SMILES: CC1(C)OB(c2cc(-c3ccc4oc5ccccc5c4c3)cc(-c3ccc4oc5ccccc5c4c3)c2)OC1(C)C]
Sub 1(6)
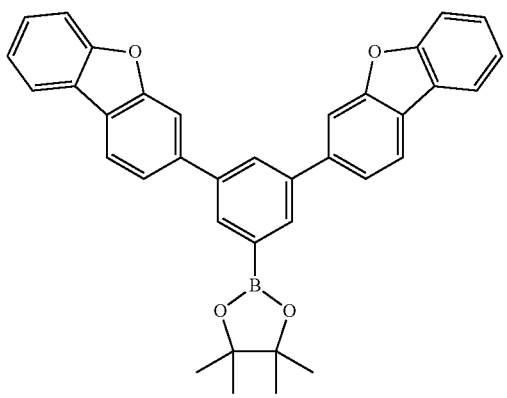 [SMILES: CC1(C)OB(c2cc(-c3ccc4c(c3)oc3ccccc34)cc(-c3ccc4c(c3)oc3ccccc34)c2)OC1(C)C]
Sub 1(7)
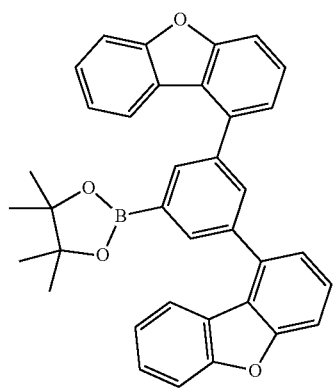 [SMILES: CC1(C)OB(c2cc(-c3cccc4oc5ccccc5c34)cc(-c3cccc4oc5ccccc5c34)c2)OC1(C)C]
Sub 1(8)

TABLE 1-continued
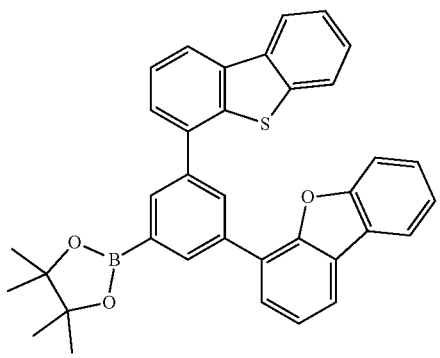 [SMILES: CC1(C)OB(c2cc(-c3cccc4c3oc3ccccc34)cc(-c3cccc4c3sc3ccccc34)c2)OC1(C)C]
Sub 1(9)
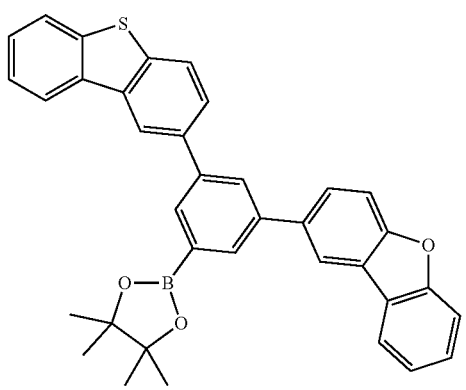 [SMILES: CC1(C)OB(c2cc(-c3ccc4oc5ccccc5c4c3)cc(-c3ccc4sc5ccccc5c4c3)c2)OC1(C)C]
Sub 1(10)
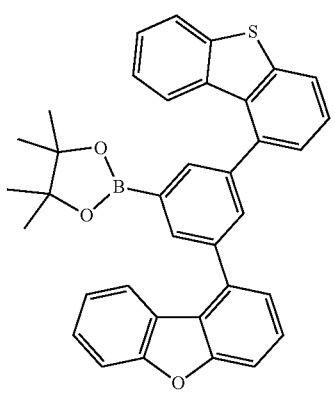 [SMILES: CC1(C)OB(c2cc(-c3cccc4oc5ccccc5c34)cc(-c3cccc4sc5ccccc5c34)c2)OC1(C)C]
Sub 1(11)
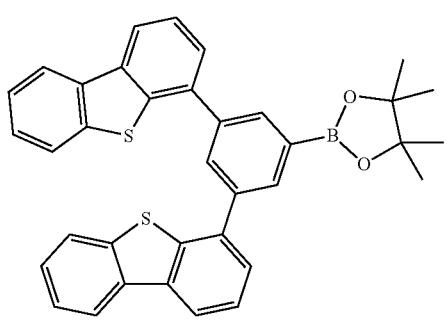
Sub 1(12)

TABLE 1-continued
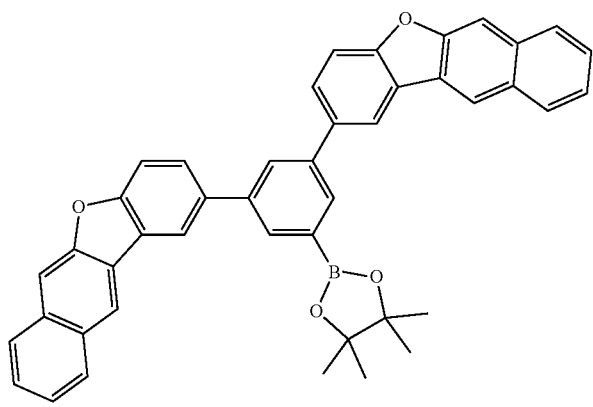 [SMILES: CC1(C)OB(c2cc(-c3ccc4oc5cc6ccccc6cc5c4c3)cc(-c3ccc4oc5cc6ccccc6cc5c4c3)c2)OC1(C)C]
Sub 1(13)
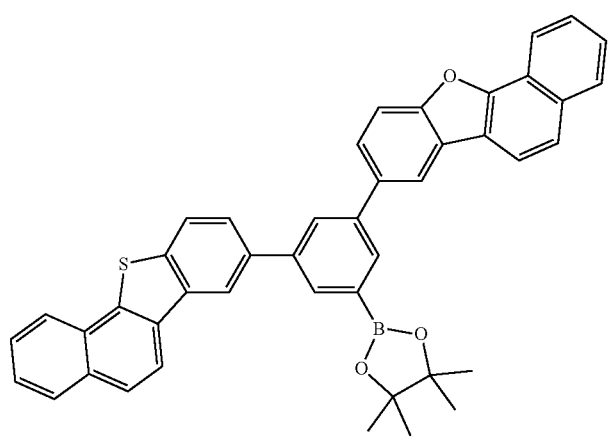 [SMILES: CC1(C)OB(c2cc(-c3ccc4oc5c6ccccc6ccc5c4c3)cc(-c3ccc4sc5c6ccccc6ccc5c4c3)c2)OC1(C)C]
Sub 1(14)
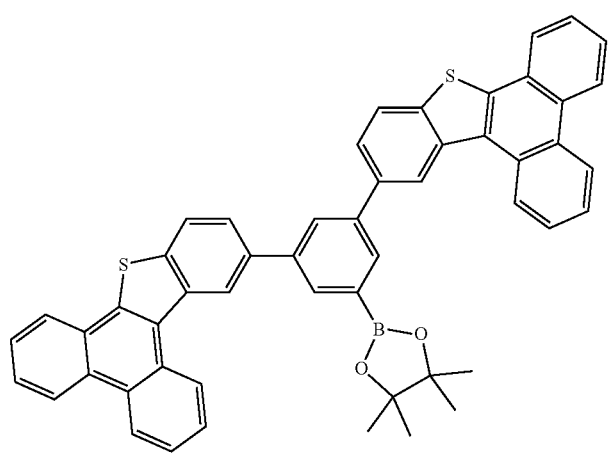 [SMILES: CC1(C)OB(c2cc(-c3ccc4sc5c6ccccc6c6ccccc6c5c4c3)cc(-c3ccc4sc5c6ccccc6c6ccccc6c5c4c3)c2)OC1(C)C]
Sub 1(15)

TABLE 1-continued
Sub 1(16)
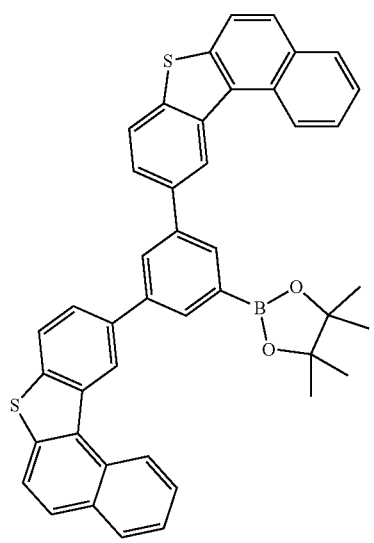 [SMILES: CC1(C)OB(c2cc(-c3ccc4sc5ccc6ccccc6c5c4c3)cc(-c3ccc4sc5ccc6ccccc6c5c4c3)c2)OC1(C)C]
Sub 1(17)
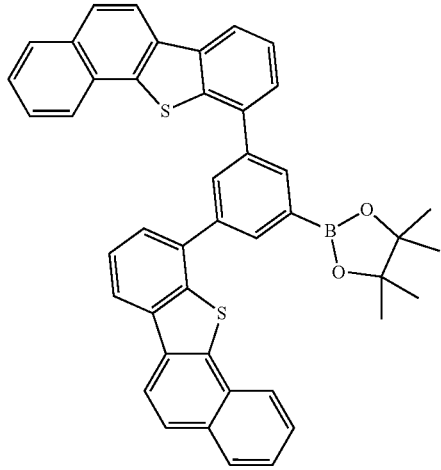 [SMILES: CC1(C)OB(c2cc(-c3cccc4c3sc3c5ccccc5ccc43)cc(-c3cccc4c3sc3c5ccccc5ccc43)c2)OC1(C)C]
Sub 1(18)
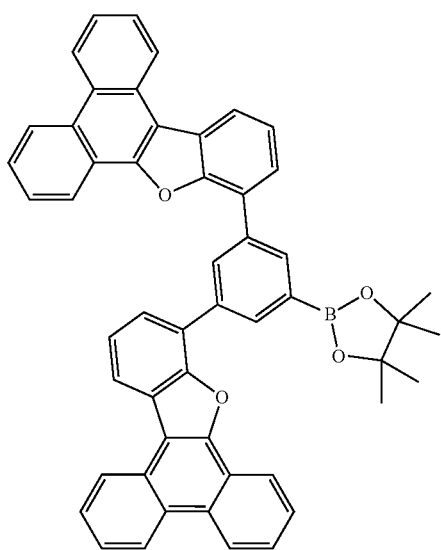 [SMILES: CC1(C)OB(c2cc(-c3cccc4c3oc3c5ccccc5c5ccccc5c43)cc(-c3cccc4c3oc3c5ccccc5c5ccccc5c43)c2)OC1(C)C]

TABLE 1-continued

Sub 1(19)

[Structure of Sub 1(19)]

| compounds | FD-MS |
|---|---|
| Sub 1(1) | m/z = 568.17 ($C_{36}H_{29}BO_2S_2$ = 568.56) |
| Sub 1(2) | m/z = 536.22 ($C_{36}H_{29}BO_4$ = 536.42) |
| Sub 1(3) | m/z = 552.19 ($C_{36}H_{29}BO_3S$ = 552.49) |
| Sub 1(4) | m/z = 568.17 ($C_{36}H_{29}BO_2S_2$ = 568.56) |
| Sub 1(5) | m/z = 568.17 ($C_{36}H_{29}BO_2S_2$ = 568.56) |
| Sub 1(6) | m/z = 536.22 ($C_{36}H_{29}BO_4$ = 536.42) |
| Sub 1(7) | m/z = 536.22 ($C_{36}H_{29}BO_4$ = 536.42) |
| Sub 1(8) | m/z = 536.22 ($C_{36}H_{29}BO_4$ = 536.42) |
| Sub 1(9) | m/z = 552.19 ($C_{36}H_{29}BO_3S$ = 552.49) |
| Sub 1(10) | m/z = 552.19 ($C_{36}H_{29}BO_3S$ = 552.49) |
| Sub 1(11) | m/z = 552.19 ($C_{36}H_{29}BO_3S$ = 552.49) |
| Sub 1(12) | m/z = 568.17 ($C_{36}H_{29}BO_2S_2$ = 568.56) |
| Sub 1(13) | m/z = 636.25 ($C_{44}H_{33}BO_4$ = 636.54) |
| Sub 1(14) | m/z = 652.22 ($C_{44}H_{33}BO_3S$ = 652.61) |
| Sub 1(15) | m/z = 768.23 ($C_{52}H_{37}BO_2S_2$ = 768.79) |
| Sub 1(16) | m/z = 668.20 ($C_{44}H_{33}BO_2S_2$ = 668.67) |
| Sub 1(17) | m/z = 668.20 ($C_{44}H_{33}BO_2S_2$ = 668.67) |
| Sub 1(18) | m/z = 738.28 ($C_{52}H_{37}BO_4$ = 736.66) |
| Sub 1(19) | m/z = 636.25 ($C_{44}H_{33}BO_4$ = 636.54) |

II. Synthesis Method of Sub 2

Sub 2 of the Reaction Scheme 1 can be synthesized according to, but not limited to, the following Reaction Scheme 3.

(When q is 2, and when two of $Ar^1$ and two of $Ar^2$ are different, 2 equivalents of Sub 2-3 can be substituted to 1 equivalent of Sub 2-4.)

1. Synthesis Method of Sub 2-(1)

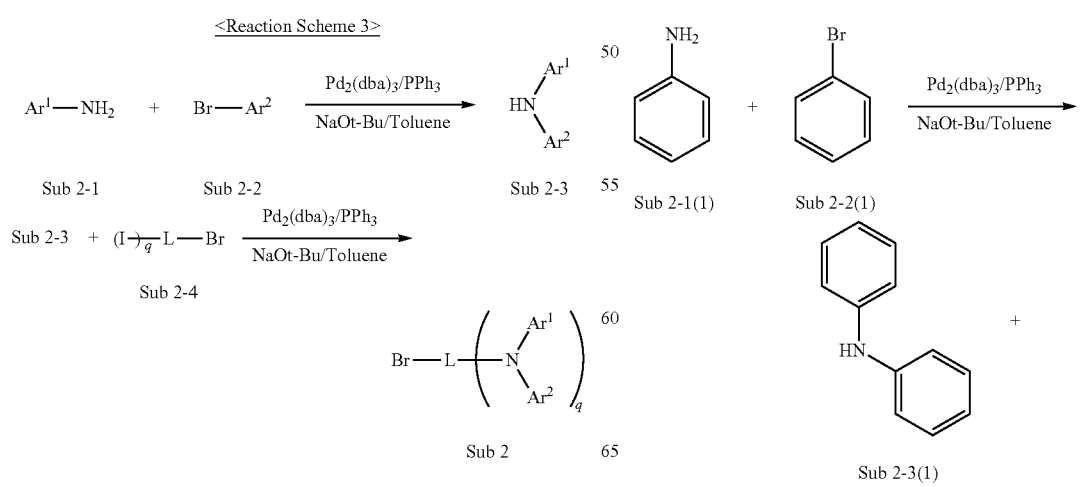

-continued

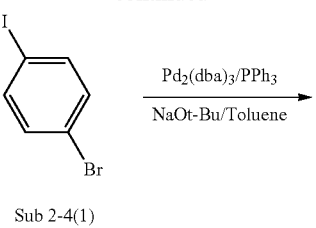

Sub 2-4(1)

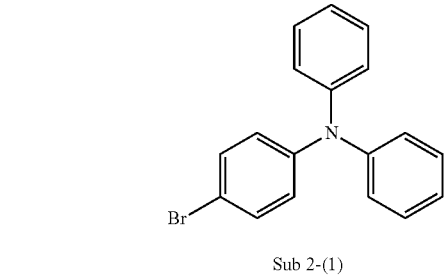

Sub 2-(1)

(1) Synthesis Method of Sub 2-3(1)

To a solution of Sub 2-1(1) (1.9 g, 20 mmol), Sub 2-2(1) (3.5 g, 22 mmol) in toluene was added Pd₂(dba)₃ (1.0 g, 1.1 mmol), PPh₃ (0.6 g, 2.2 mmol), NaOt—Bu (6.3 g, 66 mmol), and refluxed at 100° C. for 24 hr. And then the solution was extracted with ether and water, dried over MgSO₄, evaporated in vacuo. The crude product was purified by silicagel column and recrystallization to give Sub 2-3(1)(2.9 g, 85%)

(2) Synthesis Method of Sub 2-(1)

To a solution of Sub 2-3(1) (2.9 g, 17 mmol), Sub 2-4(1) (5.4 g, 19 mmol) in toluene was added Pd₂(dba)₃ (0.9 g, 1 mmol), PPh₃ (0.5 g, 1.9 mmol), NaOt-Bu (5.4 g, 57 mmol), and refluxed at 100° C. for 24 hr. And then the solution was extracted with ether and water, dried over MgSO₄, evaporated in vacuo. The crude product was purified by silicagel column and recrystallization to give Sub 2-(1)(4.5 g, 81%)

2. Synthesis Method of Sub 2-(53)

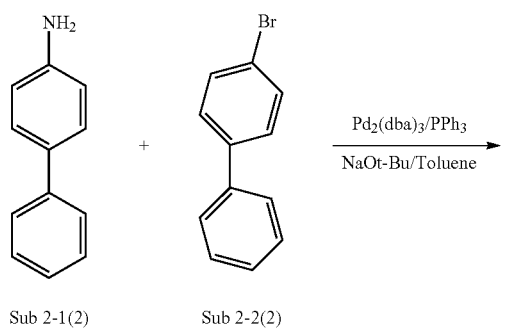

Sub 2-1(2)   Sub 2-2(2)

-continued

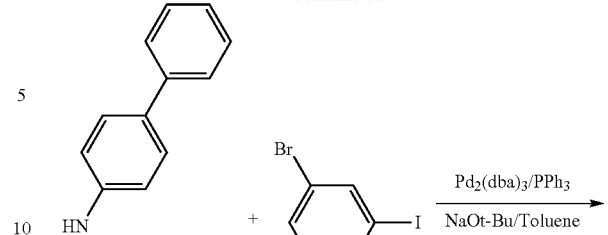

Sub 2-3(2)   Sub 2-4(2)

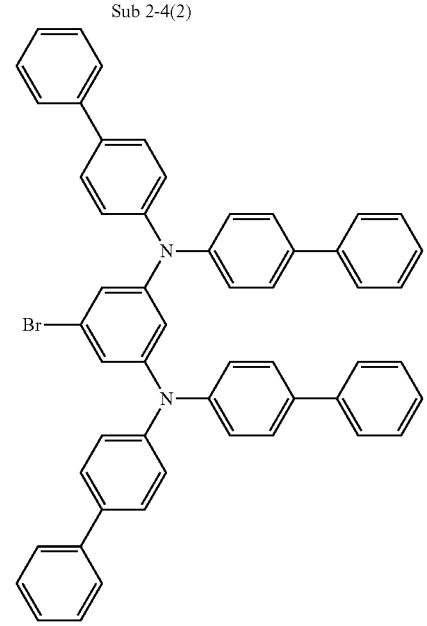

Sub 2-(53)

(1) Synthesis Method of Sub 2-3(2)

To a solution of Sub 2-1(2) (3.4 g, 20 mmol), Sub 2-2(2) (5.1 g, 22 mmol) in toluene was added Pd₂ (dba)₃ (1.0 g, 1.1 mmol), PPh₃ (0.6 g, 2.2 mmol), NaOt-Bu (6.3 g, 66 mmol), Sub 2-3(2)(5.0 g, 78%) was prepared according to the same way for Sub 2-3(1).

(2) Synthesis Method of Sub 2-(53)

To a solution of Sub 2-3(2) (5.0 g, 16 mmol), Sub 2-4(2) (9.0 g, 22 mmol) in toluene was added Pd₂(dba)₃ (0.9 g, 1 mmol), PPh₃ (0.5 g, 1.9 mmol), NaOt-Bu (5.4 g, 57 mmol), Sub 2-(53) (9.9 g, 80%) was prepared according to the same way for Sub 2-3(1).

Examples of Sub 2 compounds include, but are not limited to, the following compounds, and FD-MS data of the compounds are given in Table 2 below.

TABLE 2
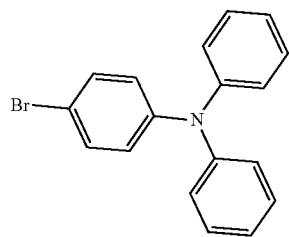 [SMILES: Brc1ccc(N(c2ccccc2)c2ccccc2)cc1]
Sub 2-(1)
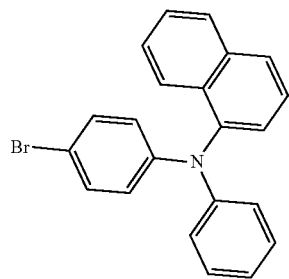 [SMILES: Brc1ccc(N(c2ccccc2)c2cccc3ccccc23)cc1]
Sub 2-(2)
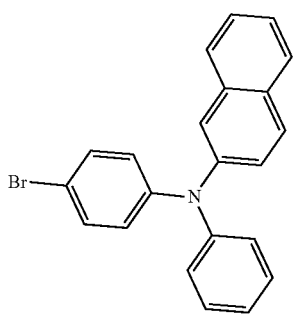 [SMILES: Brc1ccc(N(c2ccccc2)c2ccc3ccccc3c2)cc1]
Sub 2-(3)
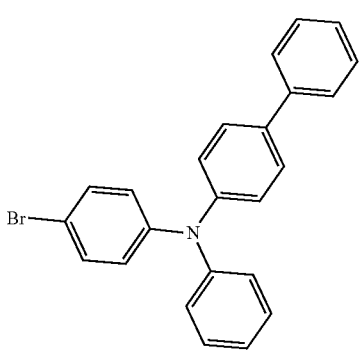 [SMILES: Brc1ccc(N(c2ccccc2)c2ccc(-c3ccccc3)cc2)cc1]
Sub 2-(4)
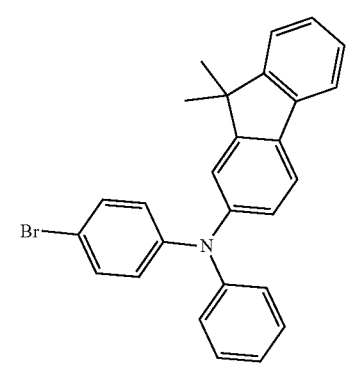 [SMILES: CC1(C)c2ccccc2-c2ccc(N(c3ccccc3)c3ccc(Br)cc3)cc21]
Sub 2-(5)

TABLE 2-continued
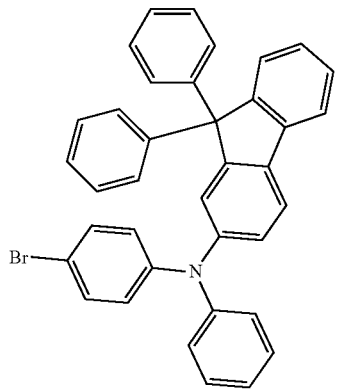 [SMILES: Brc1ccc(N(c2ccccc2)c2ccc3c(c2)C(c2ccccc2)(c2ccccc2)c2ccccc2-3)cc1]
Sub 2-(6)
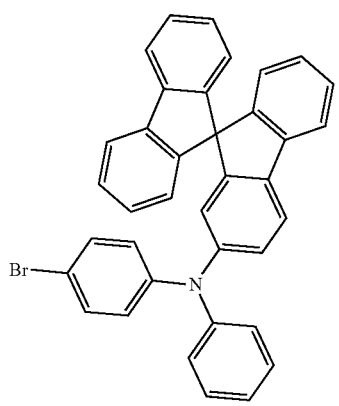 [SMILES: Brc1ccc(N(c2ccccc2)c2ccc3c(c2)C2(c4ccccc4-c4ccccc42)c2ccccc2-3)cc1]
Sub 2-(7)
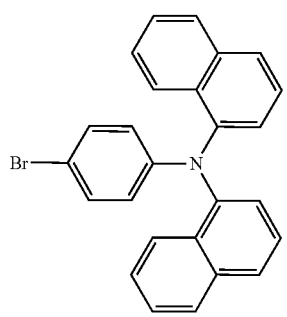 [SMILES: Brc1ccc(N(c2cccc3ccccc23)c2cccc3ccccc23)cc1]
Sub 2-(8)
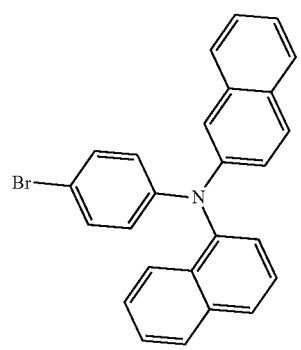 [SMILES: Brc1ccc(N(c2ccc3ccccc3c2)c2cccc3ccccc23)cc1]
Sub 2-(9)

TABLE 2-continued
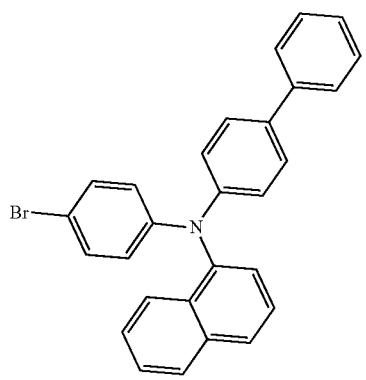 [SMILES: Brc1ccc(N(c2ccc(-c3ccccc3)cc2)c2cccc3ccccc23)cc1]
Sub 2-(10)
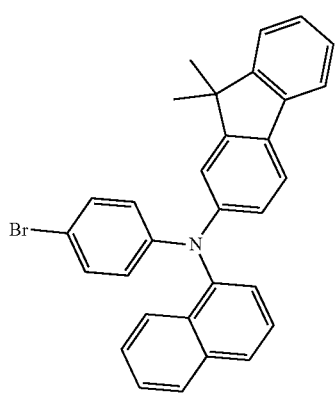 [SMILES: CC1(C)c2ccccc2-c2ccc(N(c3ccc(Br)cc3)c3cccc4ccccc34)cc21]
Sub 2-(11)
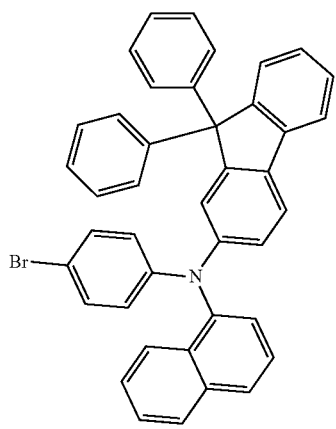 [SMILES: Brc1ccc(N(c2ccc3c(c2)C(c2ccccc2)(c2ccccc2)c2ccccc2-3)c2cccc3ccccc23)cc1]
Sub 2-(12)
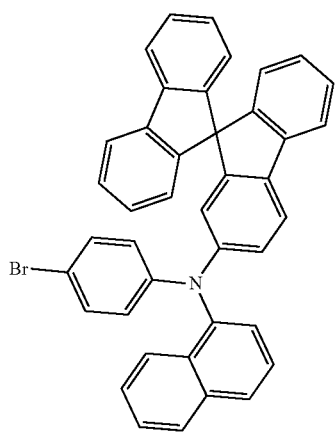 [SMILES: Brc1ccc(N(c2ccc3c(c2)C2(c4ccccc4-c4ccccc42)c2ccccc2-3)c2cccc3ccccc23)cc1]
Sub 2-(13)

TABLE 2-continued
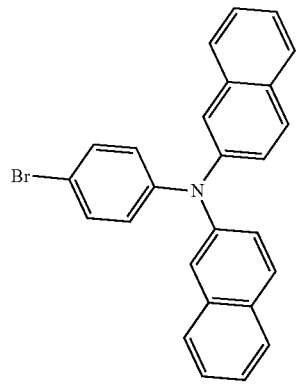 [SMILES: Brc1ccc(N(c2ccc3ccccc3c2)c2ccc3ccccc3c2)cc1]
Sub 2-(14)
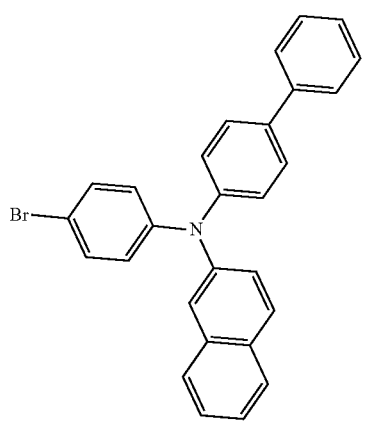 [SMILES: Brc1ccc(N(c2ccc(-c3ccccc3)cc2)c2ccc3ccccc3c2)cc1]
Sub 2-(15)
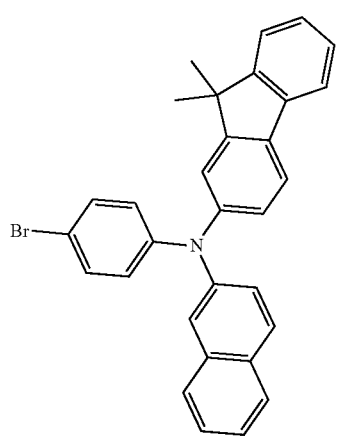 [SMILES: CC1(C)c2ccccc2-c2ccc(N(c3ccc(Br)cc3)c3ccc4ccccc4c3)cc21]
Sub 2-(16)

TABLE 2-continued
Sub 2-(17)
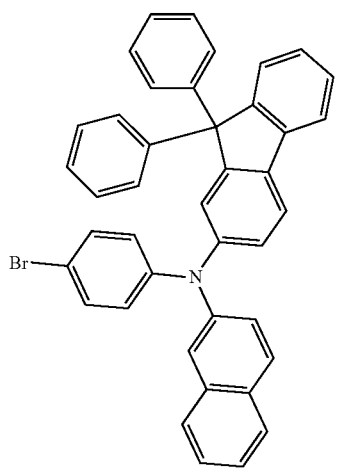 [SMILES: Brc1ccc(N(c2ccc3c(c2)C(c2ccccc2)(c2ccccc2)c2ccccc2-3)c2ccc3ccccc3c2)cc1]
Sub 2-(18)
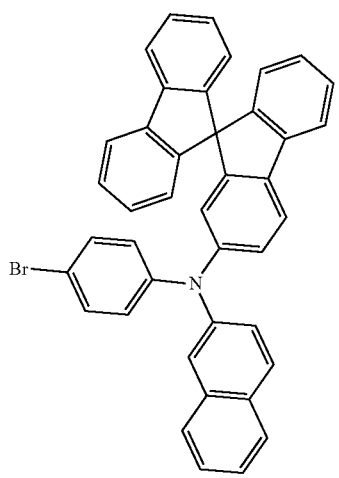 [SMILES: Brc1ccc(N(c2ccc3c(c2)C2(c4ccccc4-c4ccccc42)c2ccccc2-3)c2ccc3ccccc3c2)cc1]
Sub 2-(19)
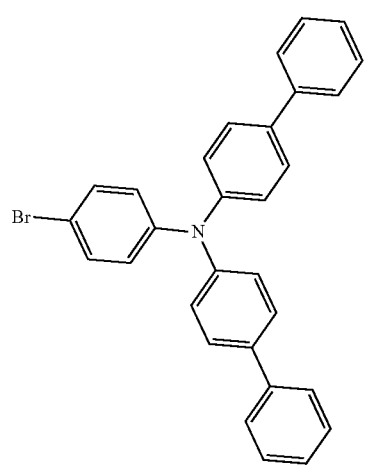 [SMILES: Brc1ccc(N(c2ccc(-c3ccccc3)cc2)c2ccc(-c3ccccc3)cc2)cc1]

TABLE 2-continued
Sub 2-(20)
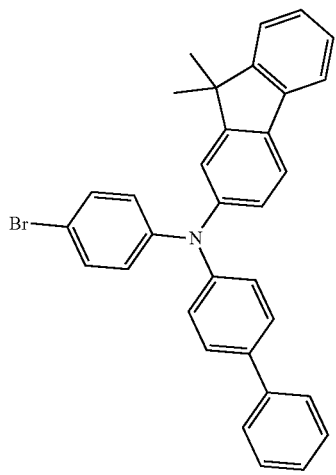 [SMILES: CC1(C)c2ccccc2-c2ccc(N(c3ccc(Br)cc3)c3ccc(-c4ccccc4)cc3)cc21]
Sub 2-(21)
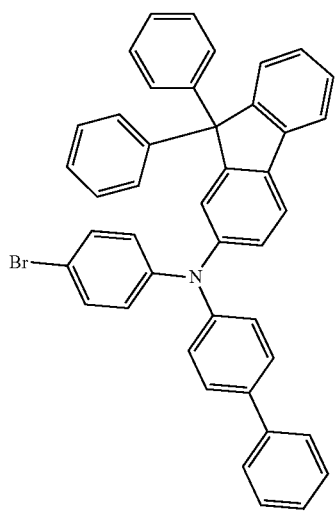 [SMILES: Brc1ccc(N(c2ccc(-c3ccccc3)cc2)c2ccc3c(c2)C(c2ccccc2)(c2ccccc2)c2ccccc2-3)cc1]
Sub 2-(22)
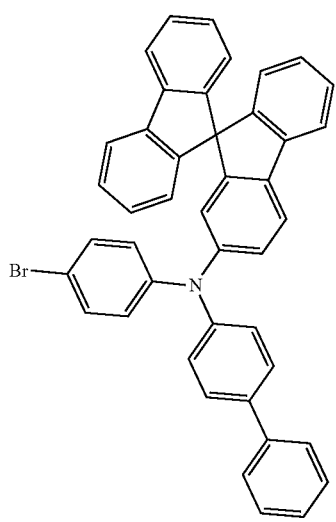 [SMILES: Brc1ccc(N(c2ccc(-c3ccccc3)cc2)c2ccc3c(c2)C2(c4ccccc4-c4ccccc42)c2ccccc2-3)cc1]

TABLE 2-continued
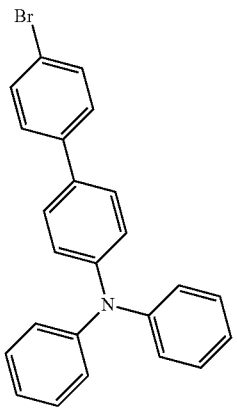 [SMILES: Brc1ccc(-c2ccc(N(c3ccccc3)c3ccccc3)cc2)cc1]
Sub 2-(23)
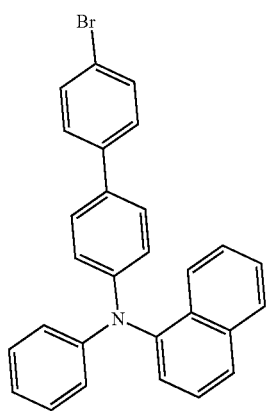 [SMILES: Brc1ccc(-c2ccc(N(c3ccccc3)c3cccc4ccccc34)cc2)cc1]
Sub 2-(24)
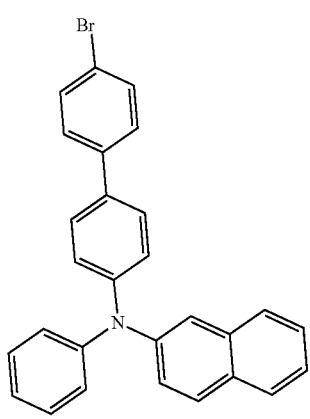 [SMILES: Brc1ccc(-c2ccc(N(c3ccccc3)c3ccc4ccccc4c3)cc2)cc1]
Sub 2-(25)
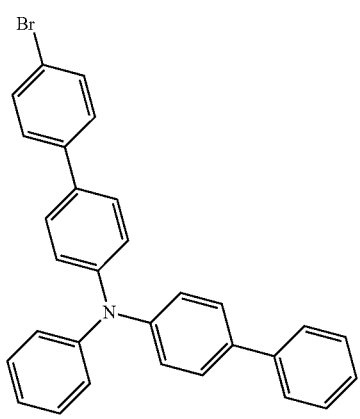 [SMILES: Brc1ccc(-c2ccc(N(c3ccccc3)c3ccc(-c4ccccc4)cc3)cc2)cc1]
Sub 2-(26)

TABLE 2-continued
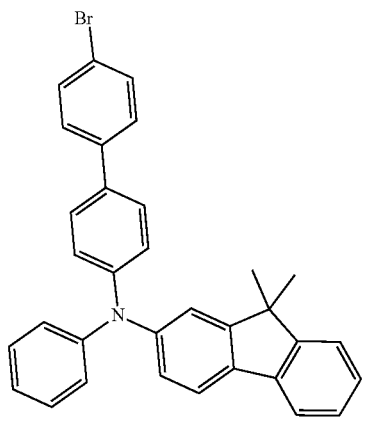 [SMILES: CC1(C)c2ccccc2-c2ccc(N(c3ccccc3)c3ccc(-c4ccc(Br)cc4)cc3)cc21]
Sub 2-(27)
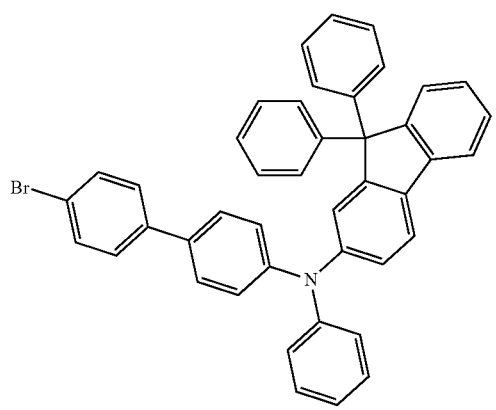 [SMILES: Brc1ccc(-c2ccc(N(c3ccccc3)c3ccc4c(c3)C(c3ccccc3)(c3ccccc3)c3ccccc3-4)cc2)cc1]
Sub 2-(28)
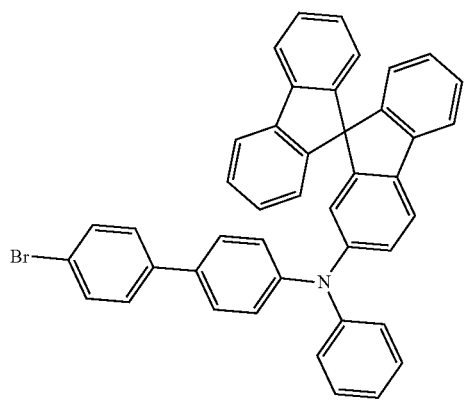 [SMILES: Brc1ccc(-c2ccc(N(c3ccccc3)c3ccc4c(c3)C3(c5ccccc5-c5ccccc53)c3ccccc3-4)cc2)cc1]
Sub 2-(29)
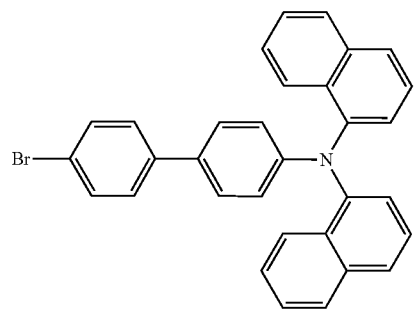 [SMILES: Brc1ccc(-c2ccc(N(c3cccc4ccccc34)c3cccc4ccccc34)cc2)cc1]
Sub 2-(30)

TABLE 2-continued
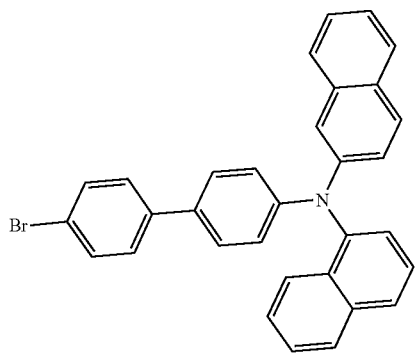 [SMILES: Brc1ccc(-c2ccc(N(c3ccc4ccccc4c3)c3cccc4ccccc34)cc2)cc1]
Sub 2-(31)
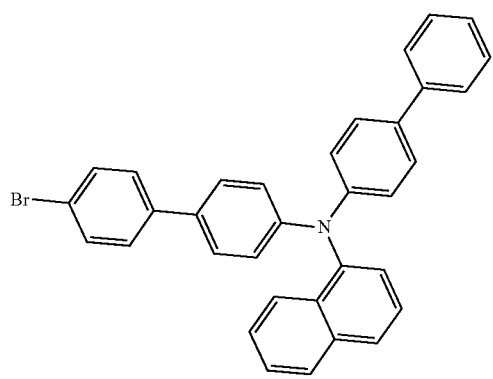 [SMILES: Brc1ccc(-c2ccc(N(c3ccc(-c4ccccc4)cc3)c3cccc4ccccc34)cc2)cc1]
Sub 2-(32)
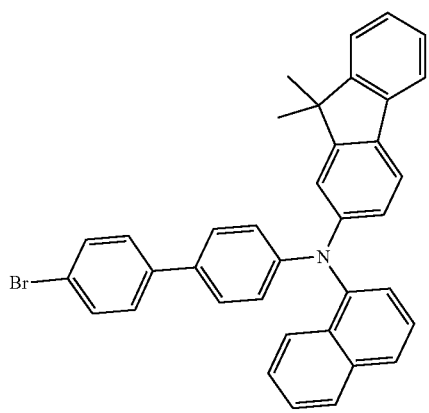 [SMILES: CC1(C)c2ccccc2-c2ccc(N(c3ccc(-c4ccc(Br)cc4)cc3)c3cccc4ccccc34)cc21]
Sub 2-(33)
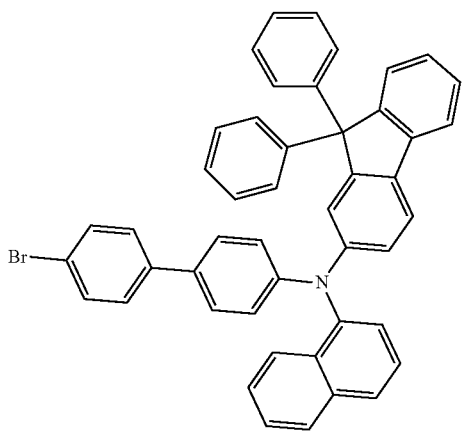 [SMILES: Brc1ccc(-c2ccc(N(c3ccc4c(c3)C(c3ccccc3)(c3ccccc3)c3ccccc3-4)c3cccc4ccccc34)cc2)cc1]
Sub 2-(34)

TABLE 2-continued
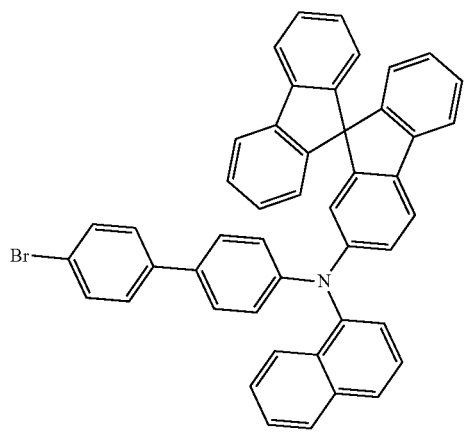 [SMILES: Brc1ccc(-c2ccc(N(c3ccc4c(c3)C3(c5ccccc5-c5ccccc53)c3ccccc3-4)c3cccc4ccccc34)cc2)cc1]
Sub 2-(35)
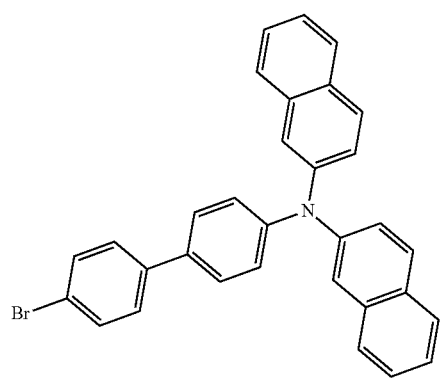 [SMILES: Brc1ccc(-c2ccc(N(c3ccc4ccccc4c3)c3ccc4ccccc4c3)cc2)cc1]
Sub 2-(36)
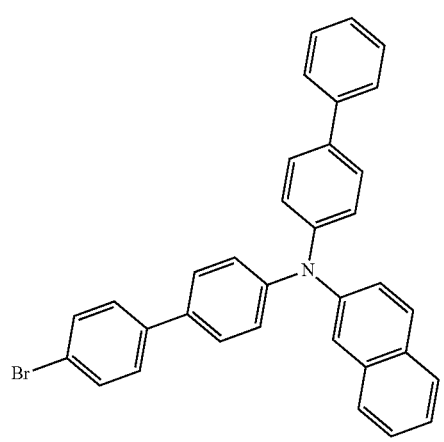 [SMILES: Brc1ccc(-c2ccc(N(c3ccc(-c4ccccc4)cc3)c3ccc4ccccc4c3)cc2)cc1]
Sub 2-(37)

TABLE 2-continued
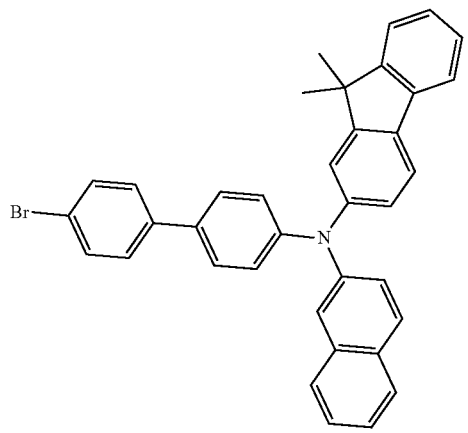 [SMILES: CC1(C)c2ccccc2-c2ccc(N(c3ccc(-c4ccc(Br)cc4)cc3)c3ccc4ccccc4c3)cc21]
Sub 2-(38)
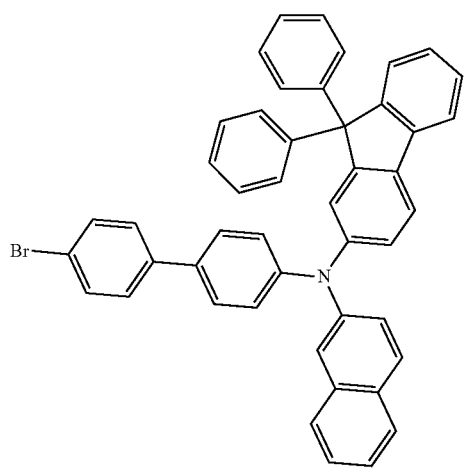 [SMILES: Brc1ccc(-c2ccc(N(c3ccc4c(c3)C(c3ccccc3)(c3ccccc3)c3ccccc3-4)c3ccc4ccccc4c3)cc2)cc1]
Sub 2-(39)
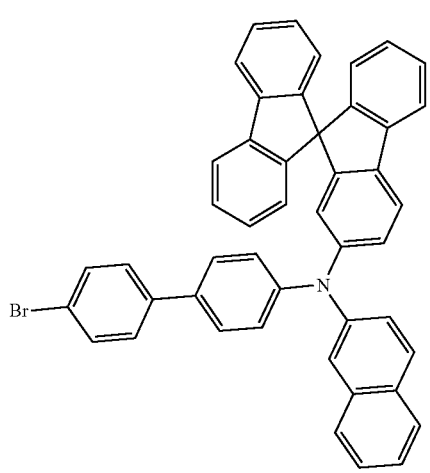 [SMILES: Brc1ccc(-c2ccc(N(c3ccc4c(c3)C3(c5ccccc5-c5ccccc53)c3ccccc3-4)c3ccc4ccccc4c3)cc2)cc1]
Sub 2-(40)

TABLE 2-continued
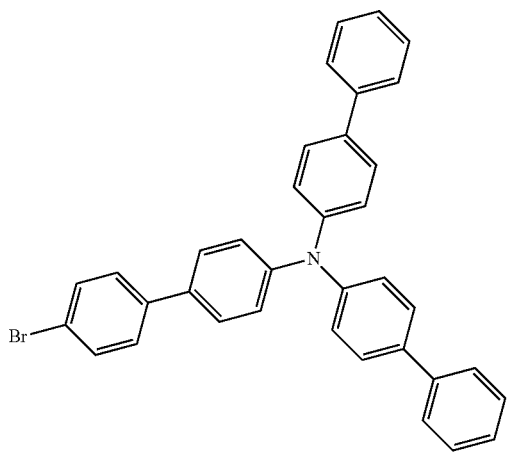 [SMILES: Brc1ccc(-c2ccc(N(c3ccc(-c4ccccc4)cc3)c3ccc(-c4ccccc4)cc3)cc2)cc1]
Sub 2-(41)
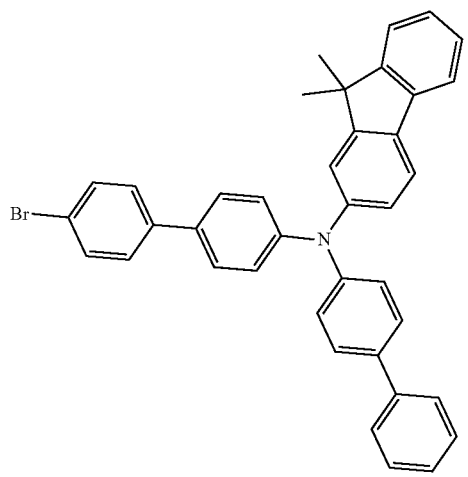 [SMILES: CC1(C)c2ccccc2-c2ccc(N(c3ccc(-c4ccccc4)cc3)c3ccc(-c4ccc(Br)cc4)cc3)cc21]
Sub 2-(42)
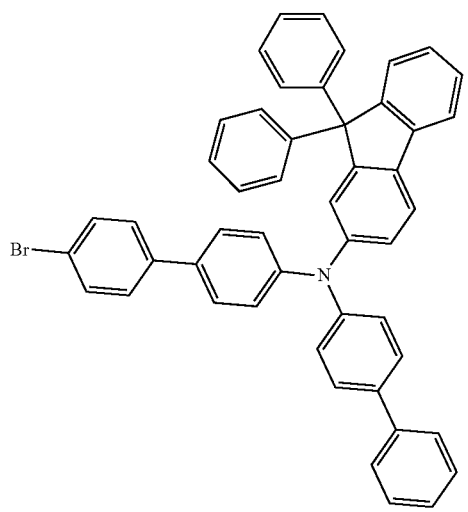 [SMILES: Brc1ccc(-c2ccc(N(c3ccc(-c4ccccc4)cc3)c3ccc4c(c3)C(c3ccccc3)(c3ccccc3)c3ccccc3-4)cc2)cc1]
Sub 2-(43)

TABLE 2-continued
Sub 2-(44)
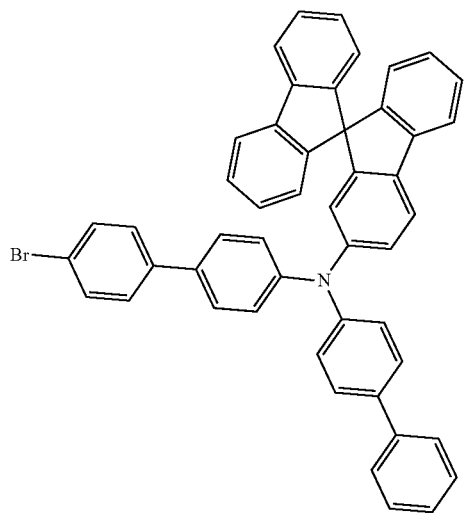 [SMILES: Brc1ccc(-c2ccc(N(c3ccc(-c4ccccc4)cc3)c3ccc4c(c3)C3(c5ccccc5-c5ccccc53)c3ccccc3-4)cc2)cc1]
Sub 2-(45)
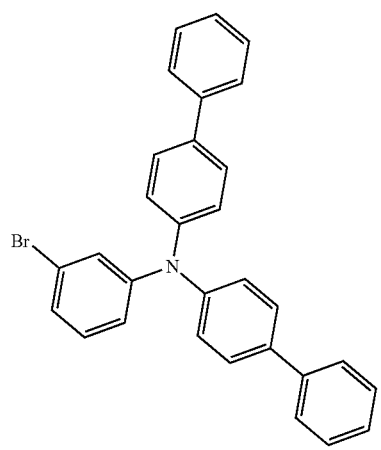 [SMILES: Brc1cccc(N(c2ccc(-c3ccccc3)cc2)c2ccc(-c3ccccc3)cc2)c1]
Sub 2-(46)
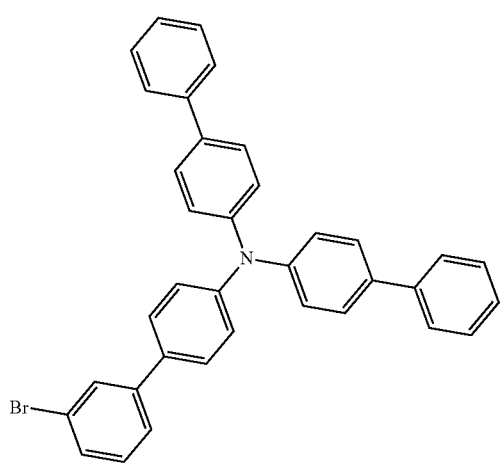 [SMILES: Brc1cccc(-c2ccc(N(c3ccc(-c4ccccc4)cc3)c3ccc(-c4ccccc4)cc3)cc2)c1]

TABLE 2-continued
Sub 2-(47)
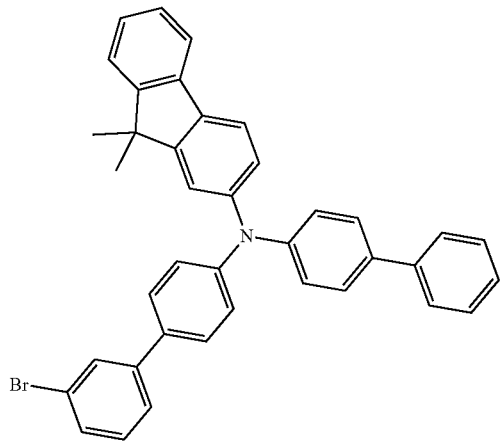 [SMILES: CC1(C)c2ccccc2-c2ccc(N(c3ccc(-c4ccccc4)cc3)c3ccc(-c4cccc(Br)c4)cc3)cc21]
Sub 2-(48)
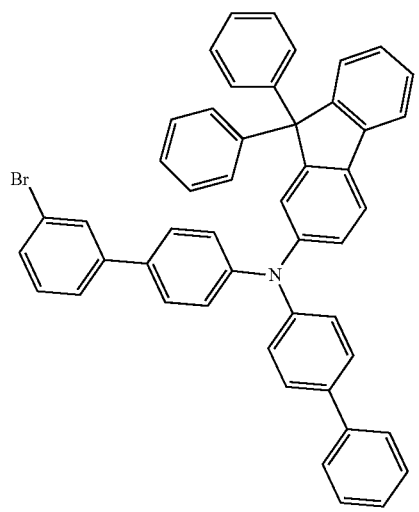 [SMILES: Brc1cccc(-c2ccc(N(c3ccc(-c4ccccc4)cc3)c3ccc4c(c3)C(c3ccccc3)(c3ccccc3)c3ccccc3-4)cc2)c1]
Sub 2-(49)
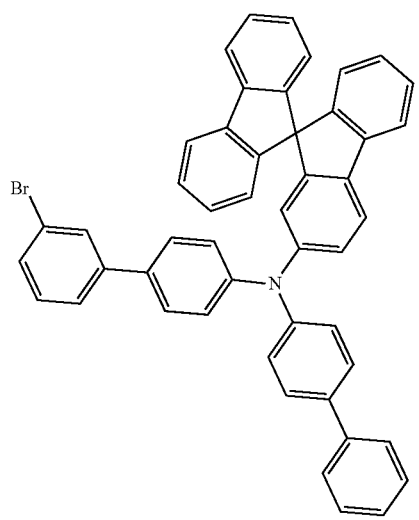 [SMILES: Brc1cccc(-c2ccc(N(c3ccc(-c4ccccc4)cc3)c3ccc4c(c3)C3(c5ccccc5-c5ccccc53)c3ccccc3-4)cc2)c1]

TABLE 2-continued
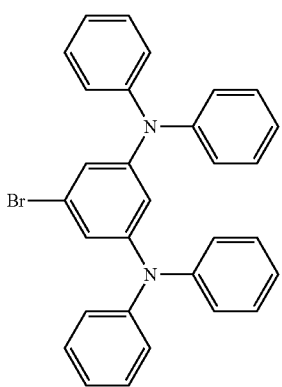 [SMILES: Brc1cc(N(c2ccccc2)c2ccccc2)cc(N(c2ccccc2)c2ccccc2)c1]
Sub 2-(50)
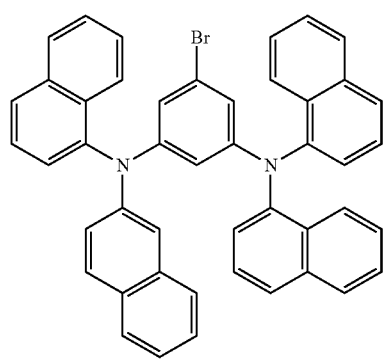 [SMILES: Brc1cc(N(c2ccc3ccccc3c2)c2cccc3ccccc23)cc(N(c2cccc3ccccc23)c2cccc3ccccc23)c1]
Sub 2-(51)
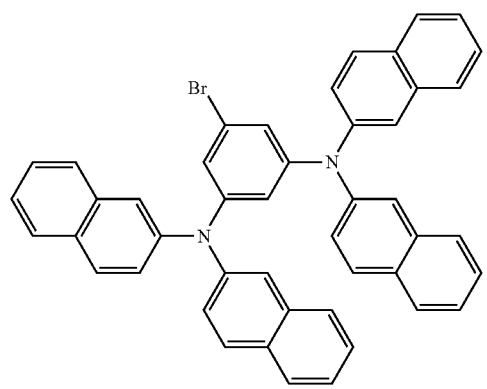 [SMILES: Brc1cc(N(c2ccc3ccccc3c2)c2ccc3ccccc3c2)cc(N(c2ccc3ccccc3c2)c2ccc3ccccc3c2)c1]
Sub 2-(52)
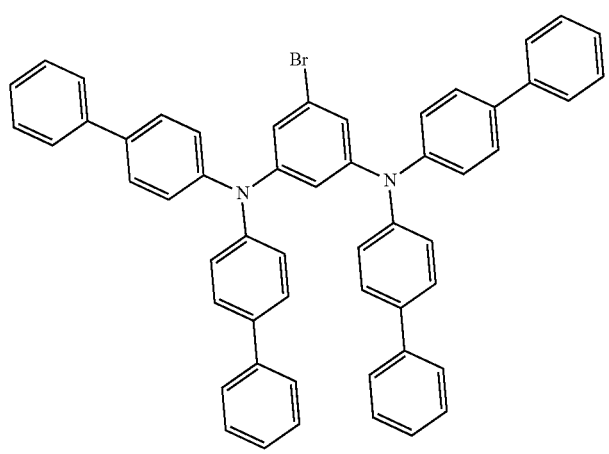 [SMILES: Brc1cc(N(c2ccc(-c3ccccc3)cc2)c2ccc(-c3ccccc3)cc2)cc(N(c2ccc(-c3ccccc3)cc2)c2ccc(-c3ccccc3)cc2)c1]
Sub 2-(53)

TABLE 2-continued

Sub 2-(54)
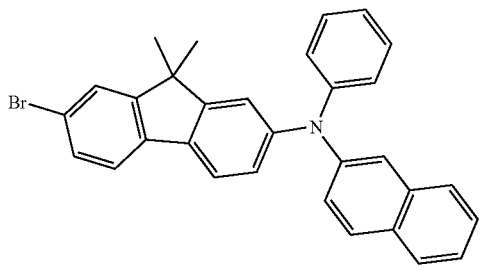 [SMILES: CC1(C)c2cc(Br)ccc2-c2ccc(N(c3ccccc3)c3ccc4ccccc4c3)cc21]

Sub 2-(55)
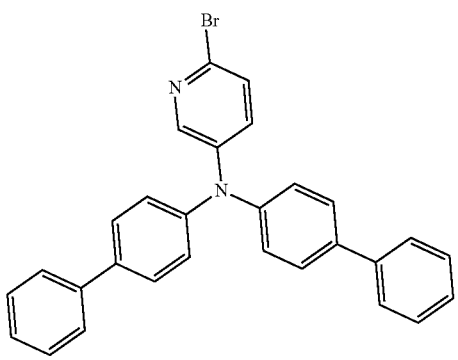 [SMILES: Brc1ccc(N(c2ccc(-c3ccccc3)cc2)c2ccc(-c3ccccc3)cc2)cn1]

Sub 2-(56)
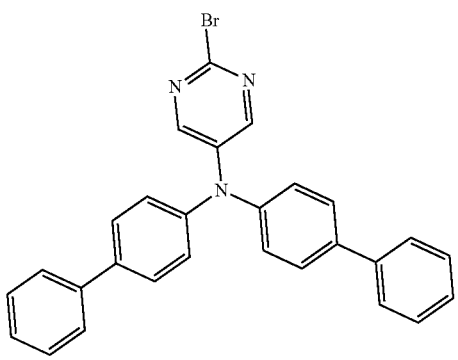 [SMILES: Brc1ncc(N(c2ccc(-c3ccccc3)cc2)c2ccc(-c3ccccc3)cc2)cn1]

| compounds | FD-MS |
|---|---|
| Sub 2-(1) | m/z = 323.03 ($C_{18}H_{14}BrN$ = 324.21) |
| Sub 2-(2) | m/z = 373.05 ($C_{22}H_{16}BrN$ = 374.27) |
| Sub 2-(3) | m/z = 373.05 ($C_{22}H_{16}BrN$ = 374.27) |
| Sub 2-(4) | m/z = 399.06 ($C_{24}H_{18}BrN$ = 400.31) |
| Sub 2-(5) | m/z = 439.09 ($C_{27}H_{22}BrN$ = 440.37) |
| Sub 2-(6) | m/z = 563.12 ($C_{37}H_{26}BrN$ = 564.51) |
| Sub 2-(7) | m/z = 561.11 ($C_{37}H_{24}BrN$ = 562.50) |
| Sub 2-(8) | m/z = 423.06 ($C_{26}H_{18}BrN$ = 424.33) |
| Sub 2-(9) | m/z = 423.06 ($C_{26}H_{18}BrN$ = 424.33) |
| Sub 2-(10) | m/z = 449.08 ($C_{28}H_{20}BrN$ = 450.37) |
| Sub 2-(11) | m/z = 489.11 ($C_{31}H_{24}BrN$ = 490.43) |
| Sub 2-(12) | m/z = 613.41 ($C_{41}H_{28}BrN$ = 641.57) |
| Sub 2-(13) | m/z = 611.12 ($C_{41}H_{26}BrN$ = 612.56) |
| Sub 2-(14) | m/z = 423.06 ($C_{26}H_{18}BrN$ = 424.33) |
| Sub 2-(15) | m/z = 449.08 ($C_{28}H_{20}BrN$ = 450.37) |
| Sub 2-(16) | m/z = 489.11 ($C_{31}H_{24}BrN$ = 490.43) |
| Sub 2-(17) | m/z = 613.14 ($C_{41}H_{28}BrN$ = 614.57) |
| Sub 2-(18) | m/z = 611.12 ($C_{41}H_{26}BrN$ = 612.56) |
| Sub 2-(19) | m/z = 475.09 ($C_{30}H_{22}BrN$ = 476.41) |
| Sub 2-(20) | m/z = 515.12 ($C_{33}H_{26}BrN$ = 516.47) |
| Sub 2-(21) | m/z = 639.16 ($C_{43}H_{30}BrN$ = 640.61) |
| Sub 2-(22) | m/z = 637.14 ($C_{43}H_{28}BrN$ = 638.59) |
| Sub 2-(23) | m/z = 399.06 ($C_{24}H_{18}BrN$ = 400.31) |
| Sub 2-(24) | m/z = 449.08 ($C_{28}H_{20}BrN$ = 450.37) |
| Sub 2-(25) | m/z = 449.08 ($C_{28}H_{20}BrN$ = 450.37) |
| Sub 2-(26) | m/z = 475.09 ($C_{30}H_{22}BrN$ = 476.41) |
| Sub 2-(27) | m/z = 515.12 ($C_{33}H_{26}BrN$ = 516.47) |
| Sub 2-(28) | m/z = 639.16 ($C_{43}H_{30}BrN$ = 640.61) |
| Sub 2-(29) | m/z = 637.14 ($C_{43}H_{28}BrN$ = 638.59) |
| Sub 2-(30) | m/z = 499.09 ($C_{32}H_{22}BrN$ = 500.43) |

TABLE 2-continued

| | |
|---|---|
| Sub 2-(31) | m/z = 499.09 ($C_{32}H_{22}BrN$ = 500.43) |
| Sub 2-(32) | m/z = 525.11 ($C_{34}H_{24}BrN$ = 526.47) |
| Sub 2-(33) | m/z = 565.14 ($C_{37}H_{28}BrN$ = 566.53) |
| Sub 2-(34) | m/z = 689.17 ($C_{47}H_{32}BrN$ = 690.67) |
| Sub 2-(35) | m/z = 687.16 ($C_{47}H_{30}BrN$ = 688.65) |
| Sub 2-(36) | m/z = 499.09 ($C_{32}H_{22}BrN$ = 500.43) |
| Sub 2-(37) | m/z = 525.11 ($C_{34}H_{24}BrN$ = 526.47) |
| Sub 2-(38) | m/z = 565.14 ($C_{37}H_{28}BrN$ = 566.53) |
| Sub 2-(39) | m/z = 689.17 ($C_{47}H_{32}BrN$ = 690.67) |
| Sub 2-(40) | m/z = 687.16 ($C_{47}H_{30}BrN$ = 688.65) |
| Sub 2-(41) | m/z = 551.12 ($C_{36}H_{26}BrN$ = 552.50) |
| Sub 2-(42) | m/z = 591.16 ($C_{39}H_{30}BrN$ = 592.57) |
| Sub 2-(43) | m/z = 715.19 ($C_{49}H_{34}BrN$ = 716.70) |
| Sub 2-(44) | m/z = 713.17 ($C_{49}H_{32}BrN$ = 714.69) |
| Sub 2-(45) | m/z = 475.09 ($C_{30}H_{22}BrN$ = 476.41) |
| Sub 2-(46) | m/z = 551.12 ($C_{36}H_{26}BrN$ = 552.50) |
| Sub 2-(47) | m/z = 591.16 ($C_{39}H_{30}BrN$ = 592.57) |
| Sub 2-(48) | m/z = 715.19 ($C_{49}H_{34}BrN$ = 716.70) |
| Sub 2-(49) | m/z = 713.17 ($C_{49}H_{32}BrN$ = 714.69) |
| Sub 2-(50) | m/z = 490.10 ($C_{30}H_{23}BrN_2$ = 491.42) |
| Sub 2-(51) | m/z = 690.17 ($C_{46}H_{31}BrN_2$ = 691.7) |
| Sub 2-(52) | m/z = 690.17 ($C_{46}H_{31}BrN_2$ = 691.7) |
| Sub 2-(53) | m/z = 794.23 ($C_{54}H_{39}BrN_2$ = 795.8) |
| Sub 2-(54) | m/z = 489.11 ($C_{31}H_{24}BrN$ = 490.43) |
| Sub 2-(55) | m/z = 476.09 ($C_{29}H_{21}BrN_2$ = 477.39) |
| Sub 2-(56) | m/z = 477.08 ($C_{28}H_{20}BrN_3$ = 478.38) |

III. Synthesis Method of Final Product

To a dissolving solution of Sub 1 (1 eq) in THF was added Sub 2 (1.2 eq), Pd(PPh$_3$)$_4$ (0.035 eq), NaOH (3 eq), and water, and then refluxed. After completion of the reaction, the reaction solution was extracted with ether and water, and dried over MgSO$_4$ and evaporated. The crude product was purified by silicagel column and recrystallization to give a Final Product.

1. Synthesis Method of 1-25

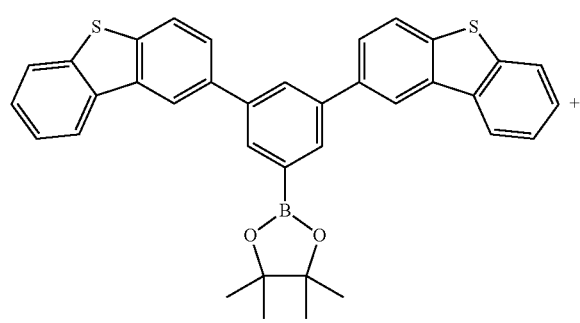

Sub 1(1)

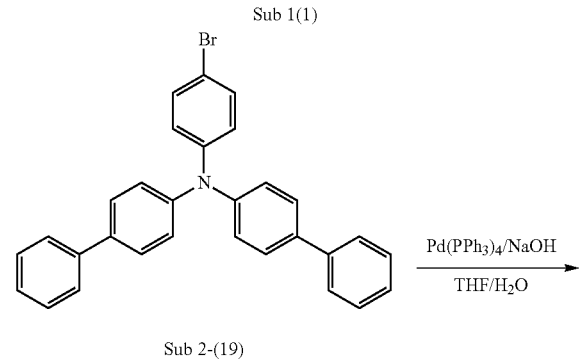

Sub 2-(19)

Pd(PPh$_3$)$_4$/NaOH
THF/H$_2$O

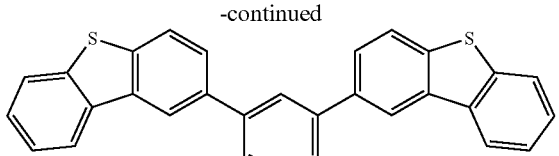

-continued

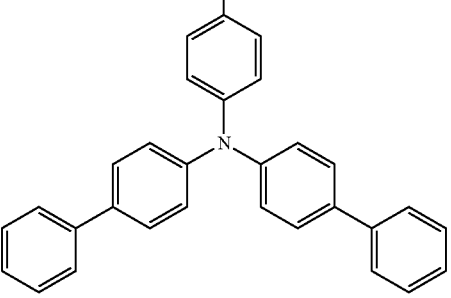

1-25

To a dissolving solution of Sub 1(1) (11.4 g, 20 mmol) in THF was added Sub 2-(19) (11.4 g, 24 mmol), Pd(PPh$_3$)$_4$ (0.8 g, 0.7 mmol), NaOH (2.4 g, 60 mmol), and water, and then refluxed. After completion of the reaction, the reaction solution was extracted with ether and water, and dried over MgSO$_4$ and evaporated. The crude product was purified by silicagel column and recrystallization to give 1-25 (14.1 g, 84%).

2. Synthesis Method of 2-26

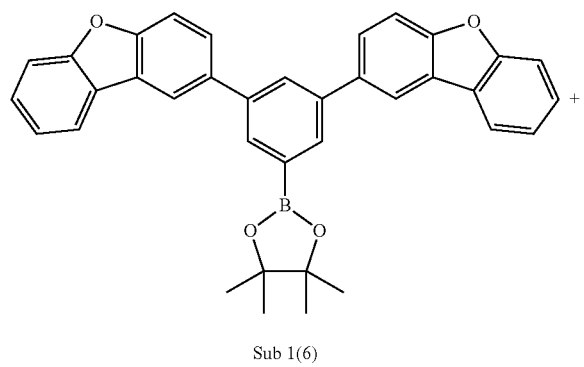

Sub 1(6)

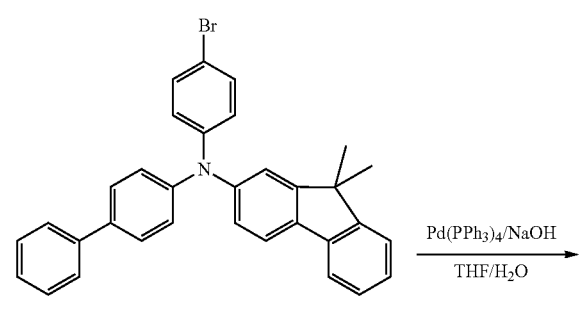

Sub 2-(20)

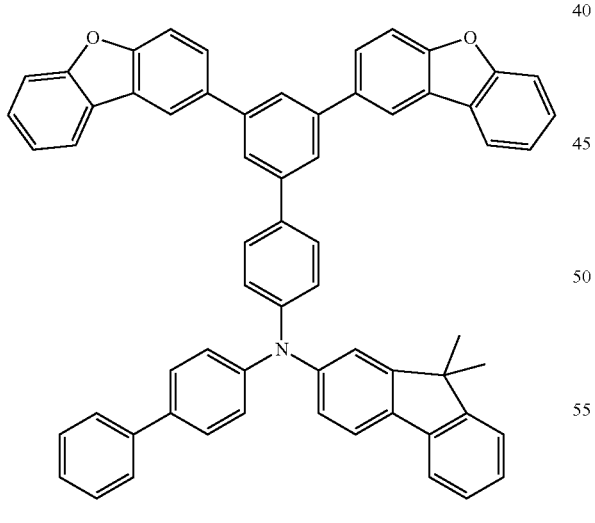

2-26

3. Synthesis Method of 4-35

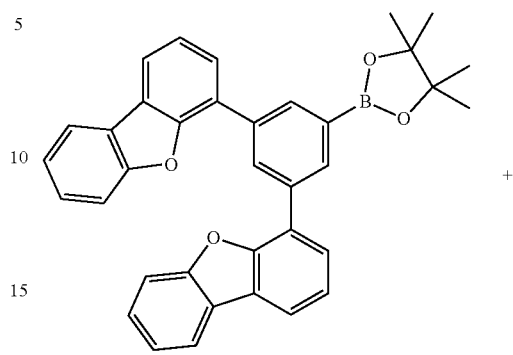

Sub 1(2)

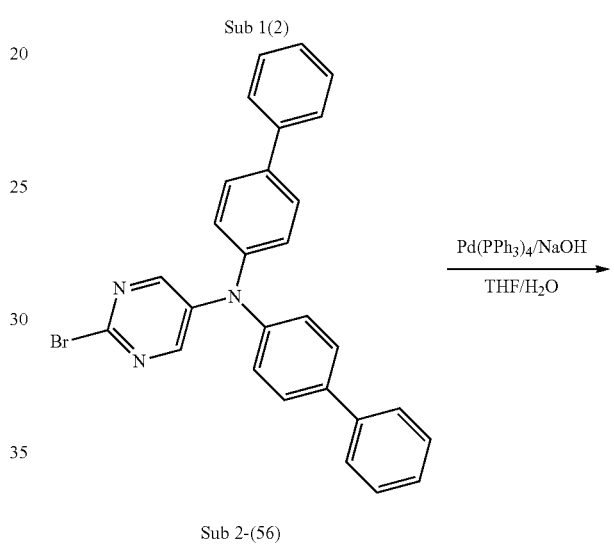

Sub 2-(56)

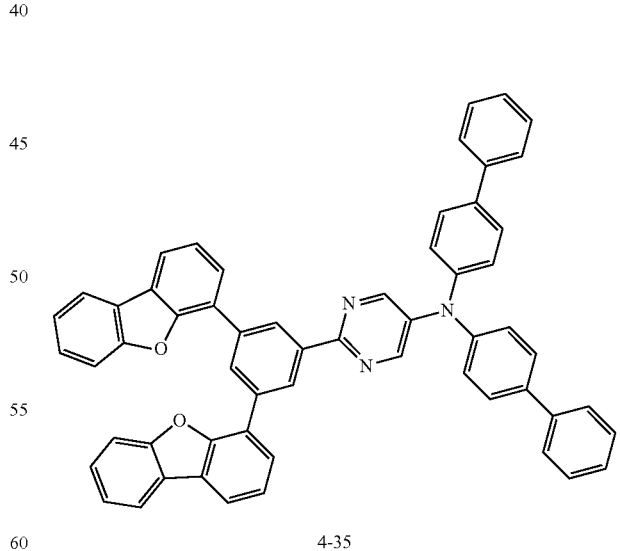

4-35

To a dissolving solution of Sub 1(6) (10.7 g, 20 mmol) in THF was added Sub 2-(20) (12.4 g, 24 mmol), Pd(PPh$_3$)$_4$ (0.8 g, 0.7 mmol), NaOH (2.4 g, 60 mmol), and water. And then 2-26 (13.2 g, 78%) was prepared according to the same way for 1-25.

To a dissolving solution of Sub 1(2) (10.7 g, 20 mmol) in THF was added Sub 2-(56) (11.5 g, 24 mmol), Pd(PPh$_3$)$_4$ (0.8 g, 0.7 mmol), NaOH(2.4 g, 60 mmol), and water. And then 4-35 (12.1 g, 75%) was prepared according to the same way for 1-25.

4. Synthesis Method of 6-1
5. Synthesis Method of 7-1
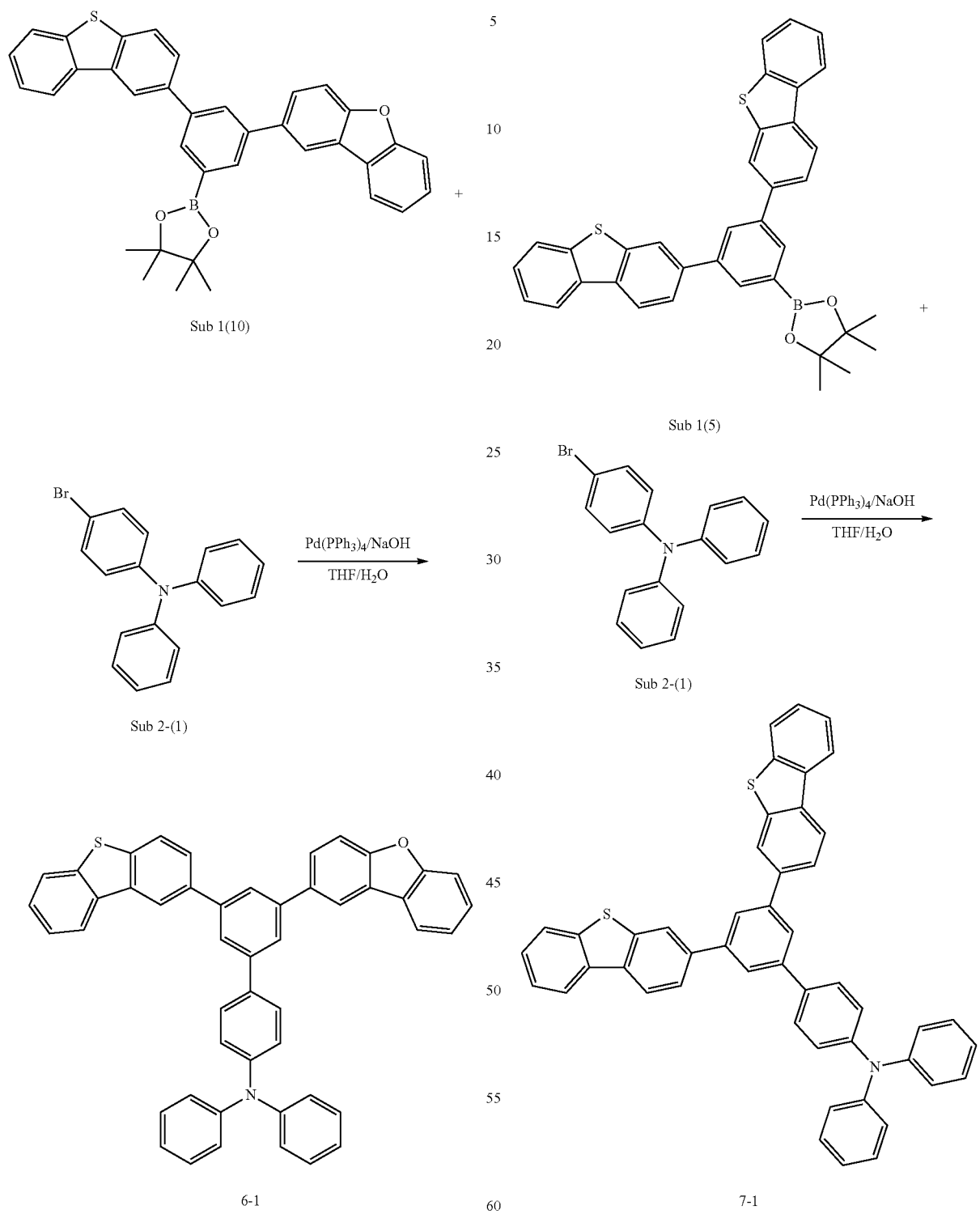
To a dissolving solution of Sub 1(10) (11.0 g, 20 mmol) in THF was added Sub 2-(1) (7.8 g, 24 mmol), Pd(PPh$_3$)$_4$ (0.8 g, 0.7 mmol), NaOH (2.4 g, 60 mmol), and water. And then 6-1 (12.1 g, 75%) was prepared according to the same way for 1-25.
To a dissolving solution of Sub 1(5) (11.4 g, 20 mmol) in THF was added Sub 2-(1) (7.8 g, 24 mmol), Pd(PPh$_3$)$_4$ (0.8 g, 0.7 mmol), NaOH (2.4 g, 60 mmol), and water. And then 7-1 (11.0 g, 80%) was prepared according to the same way for 1-25.

6. Synthesis Method of 7-9

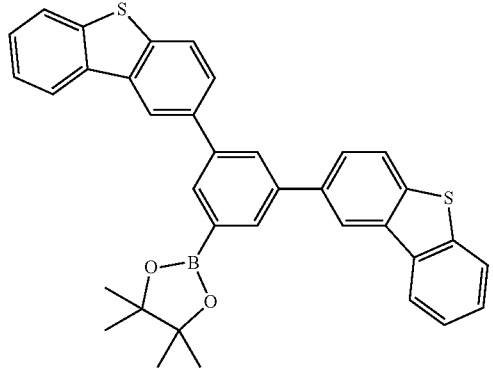

Sub 1(1)

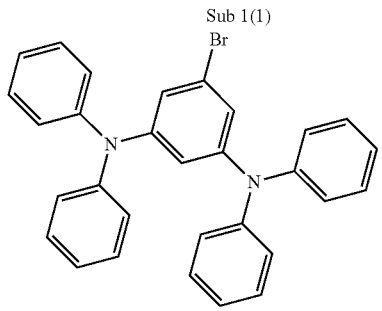

Sub 2-(50)

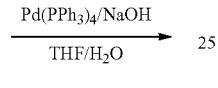

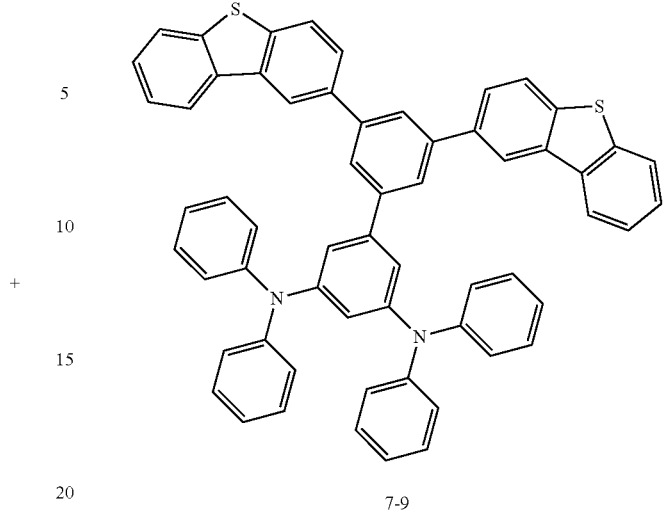

7-9

To a dissolving solution of Sub 1(1) (11.4 g, 20 mmol) in THF was added Sub 2-(50) (11.8 g, 24 mmol), Pd(PPh$_3$)$_4$ (0.8 g, 0.7 mmol), NaOH (2.4 g, 60 mmol), and water. And then 7-9 (12.6 g, 74%) was prepared according to the same way for 1-25.

TABLE 3

| compounds | FD-MS | compounds | FD-MS |
|---|---|---|---|
| 1-1 | m/z = 685.19($C_{48}H_{31}NS_2$ = 685.90) | 1-2 | m/z = 735.21($C_{52}H_{33}NS_2$ = 735.96) |
| 1-3 | m/z = 735.21($C_{52}H_{33}NS_2$ = 735.96) | 1-4 | m/z = 761.22($C_{54}H_{35}NS_2$ = 761.99) |
| 1-5 | m/z = 801.25($C_{57}H_{39}NS_2$ = 802.06) | 1-6 | m/z = 925.28($C_{67}H_{43}NS_2$ = 926.20) |
| 1-7 | m/z = 923.27($C_{67}H_{41}NS_2$ = 924.18) | 1-8 | m/z = 785.22($C_{56}H_{35}NS_2$ = 786.01) |
| 1-9 | m/z = 785.22($C_{56}H_{35}NS_2$ = 786.01) | 1-10 | m/z = 811.24($C_{58}H_{37}NS_2$ = 812.05) |
| 1-11 | m/z = 851.27($C_{61}H_{41}NS_2$ = 852.11) | 1-12 | m/z = 975.30($C_{71}H_{45}NS_2$ = 976.25) |
| 1-13 | m/z = 973.28($C_{71}H_{43}NS_2$ = 974.24) | 1-14 | m/z = 785.22($C_{56}H_{35}NS_2$ = 786.01) |
| 1-15 | m/z = 811.24($C_{58}H_{37}NS_2$ = 812.05) | 1-16 | m/z = 851.27($C_{61}H_{41}NS_2$ = 852.11) |
| 1-17 | m/z = 975.30($C_{71}H_{45}NS_2$ = 976.25) | 1-18 | m/z = 973.28($C_{71}H_{43}NS_2$ = 974.24) |
| 1-19 | m/z = 837.25($C_{60}H_{39}NS_2$ = 838.09) | 1-20 | m/z = 877.28($C_{63}H_{43}NS_2$ = 878.15) |
| 1-21 | m/z = 1001.31($C_{73}H_{47}NS_2$ = 1002.29) | 1-22 | m/z = 999.30($C_{73}H_{45}NS_2$ = 1000.28) |
| 1-23 | m/z = 837.25($C_{60}H_{39}NS_2$ = 838.09) | 1-24 | m/z = 937.28($C_{68}H_{43}NS_2$ = 938.21) |
| 1-25 | m/z = 937.28($C_{68}H_{43}NS_2$ = 938.21) | 1-26 | m/z = 838.25($C_{59}H_{38}N_2S_2$ = 839.08) |
| 1-27 | m/z = 839.24($C_{58}H_{37}N_3S_2$ = 840.06) | 1-28 | m/z = 913.28($C_{66}H_{43}NS_2$ = 914.18) |
| 2-1 | m/z = 653.24($C_{48}H_{31}NO_2$ = 653.77) | 2-2 | m/z = 703.25($C_{52}H_{33}NO_2$ = 703.82) |
| 2-3 | m/z = 703.25($C_{52}H_{33}NO_2$ = 703.82) | 2-4 | m/z = 729.27($C_{54}H_{35}NO_2$ = 729.86) |
| 2-5 | m/z = 769.30($C_{57}H_{39}NO_2$ = 769.93) | 2-6 | m/z = 893.33($C_{67}H_{43}NO_2$ = 894.06) |
| 2-7 | m/z = 891.31($C_{67}H_{41}NO_2$ = 892.05) | 2-8 | m/z = 753.27($C_{56}H_{35}NO_2$ = 753.88) |
| 2-9 | m/z = 753.27($C_{56}H_{35}NO_2$ = 753.88) | 2-10 | m/z = 779.28($C_{58}H_{37}NO_2$ = 779.92) |
| 2-11 | m/z = 819.31($C_{61}H_{41}NO_2$ = 819.98) | 2-12 | m/z = 943.35($C_{71}H_{45}NO_2$ = 944.12) |
| 2-13 | m/z = 941.33($C_{71}H_{43}NO_2$ = 942.11) | 2-14 | m/z = 753.27($C_{56}H_{35}NO_2$ = 753.88) |
| 2-15 | m/z = 779.28($C_{58}H_{37}NO_2$ = 779.92) | 2-16 | m/z = 819.31($C_{61}H_{41}NO_2$ = 819.98) |
| 2-17 | m/z = 943.35($C_{71}H_{45}NO_2$ = 944.12) | 2-18 | m/z = 941.33($C_{71}H_{43}NO_2$ = 942.11) |
| 2-19 | m/z = 805.30($C_{60}H_{33}NO_2$ = 805.96) | 2-20 | m/z = 845.33($C_{63}H_{43}NO_2$ = 846.02) |
| 2-21 | m/z = 969.36($C_{73}H_{47}NO_2$ = 970.16) | 2-22 | m/z = 967.35($C_{73}H_{45}NO_2$ = 968.14) |
| 2-23 | m/z = 805.30($C_{60}H_{33}NO_2$ = 805.96) | 2-24 | m/z = 905.33($C_{68}H_{43}NO_2$ = 906.07) |
| 2-25 | m/z = 905.33($C_{68}H_{43}NO_2$ = 906.07) | 2-26 | m/z = 806.29($C_{53}H_{38}N_3O_2$ = 806.95) |
| 2-27 | m/z = 807.29($C_{58}H_{37}N_3O_2$ = 807.93) | 2-28 | m/z = 881.33($C_{66}H_{43}NO_2$ = 882.05) |
| 3-1 | m/z = 685.19($C_{48}H_{31}NS_2$ = 685.90) | 3-2 | m/z = 735.21($C_{52}H_{33}NS_2$ = 735.96) |
| 3-3 | m/z = 735.21($C_{52}H_{33}NS_2$ = 735.96) | 3-4 | m/z = 761.22($C_{54}H_{35}NS_2$ = 761.99) |
| 3-5 | m/z = 801.25($C_{57}H_{33}NS_2$ = 802.06) | 3-6 | m/z = 925.28($C_{67}H_{43}NS_2$ = 926.20) |
| 3-7 | m/z = 923.27($C_{67}H_{41}NS_2$ = 924.18) | 3-8 | m/z = 785.22($C_{56}H_{35}NS_2$ = 786.01) |
| 3-9 | m/z = 785.22($C_{56}H_{35}NS_2$ = 786.01) | 3-10 | m/z = 811.24($C_{58}H_{37}NS_2$ = 812.05) |
| 3-11 | m/z = 851.27($C_{61}H_{41}NS_2$ = 852.11) | 3-12 | m/z = 975.30($C_{71}H_{45}NS_2$ = 976.25) |
| 3-13 | m/z = 973.28($C_{71}H_{43}NS_2$ = 974.24) | 3-14 | m/z = 785.22($C_{56}H_{35}NS_2$ = 786.01) |

TABLE 3-continued

| compounds | FD-MS | compounds | FD-MS |
|---|---|---|---|
| 3-15 | m/z = 811.24($C_{58}H_{37}NS_2$ = 812.05) | 3-16 | m/z = 851.27($C_{61}H_{41}NS_2$ = 852.11) |
| 3-17 | m/z = 975.30($C_{71}H_{45}NS_2$ = 976.25) | 3-18 | m/z = 973.28($C_{71}H_{43}NS_2$ = 974.24) |
| 3-19 | m/z = 837.25($C_{60}H_{33}NS_2$ = 838.09) | 3-20 | m/z = 877.28($C_{63}H_{43}NS_2$ = 878.15) |
| 3-21 | m/z = 1001.31($C_{73}H_{47}NS_2$ = 1002.29) | 3-22 | m/z = 999.30($C_{73}H_{45}NS_2$ = 1000.28) |
| 3-23 | m/z = 837.25($C_{60}H_{33}NS_2$ = 838.09) | 3-24 | m/z = 937.28($C_{68}H_{43}NS_2$ = 938.21) |
| 3-25 | m/z = 937.28($C_{68}H_{43}NS_2$ = 938.21) | 3-26 | m/z = 838.25($C_{53}H_{38}N_2S_2$ = 839.08) |
| 3-27 | m/z = 839.24($C_{58}H_{37}N_3S_2$ = 840.06) | 3-28 | m/z = 913.28($C_{66}H_{43}NS_2$ = 914.18) |
| 4-1 | m/z = 653.24($C_{48}H_{31}NO_2$ = 653.77) | 4-2 | m/z = 703.25($C_{52}H_{33}NO_2$ = 703.82) |
| 4-3 | m/z = 703.25($C_{52}H_{33}NO_2$ = 703.82) | 4-4 | m/z = 729.27($C_{54}H_{35}NO_2$ = 729.86) |
| 4-5 | m/z = 769.30($C_{57}H_{33}NO_2$ = 769.93) | 4-6 | m/z = 893.33($C_{67}H_{43}NO_2$ = 894.06) |
| 4-7 | m/z = 891.31($C_{67}H_{41}NO_2$ = 892.05) | 4-8 | m/z = 753.27($C_{56}H_{35}NO_2$ = 753.88) |
| 4-9 | m/z = 753.27($C_{56}H_{35}NO_2$ = 753.88) | 4-10 | m/z = 779.28($C_{58}H_{37}NO_2$ = 779.92) |
| 4-11 | m/z = 819.31($C_{61}H_{41}NO_2$ = 819.98) | 4-12 | m/z = 943.35($C_{71}H_{45}NO_2$ = 944.12) |
| 4-13 | m/z = 941.33($C_{71}H_{43}NO_2$ = 942.11) | 4-14 | m/z = 753.27($C_{56}H_{35}NO_2$ = 753.88) |
| 4-15 | m/z = 779.28($C_{58}H_{37}NO_2$ = 779.92) | 4-16 | m/z = 819.31($C_{61}H_{41}NO_2$ = 819.98) |
| 4-17 | m/z = 943.35($C_{71}H_{45}NO_2$ = 944.12 | 4-18 | m/z = 941.33($C_{71}H_{43}NO_2$ = 942.11) |
| 4-19 | m/z = 805.30($C_{60}H_{33}NO_2$ = 805.96) | 4-20 | m/z = 845.33($C_{63}H_{43}NO_2$ = 846.02) |
| 4-21 | m/z = 969.36($C_{23}H_{42}NO_2$ = 970.16) | 4-22 | m/z = 967.35($C_{23}H_{45}NO_2$ = 968.14) |
| 4-23 | m/z = 805.30($C_{60}H_{33}NO_2$ = 805.96) | 4-24 | m/z = 905.33($C_{68}H_{43}NO_2$ = 906.07) |
| 4-25 | m/z = 905.33($C_{68}H_{43}NO_2$ = 906.07) | 4-26 | m/z = 806.29($C_{53}H_{38}N_2O_2$ = 806.95) |
| 4-27 | m/z = 807.29($C_{58}H_{32}N_3O_2$ = 807.93) | 4-28 | m/z = 881.33($C_{66}H_{43}NO_2$ = 882.05) |
| 5-1 | m/z = 937.28($C_{68}H_{43}NS_2$ = 938.21) | 5-3 | m/z = 905.33($C_{68}H_{43}NO_2$ = 906.07) |
| 5-2 | m/z = 937.28($C_{68}H_{43}NS_2$ = 938.21) | 5-4 | m/z = 1005.36($C_{26}H_{42}NO_2$ = 1006.19) |
| 6-1 | m/z = 669.21($C_{48}H_{31}NOS$ = 669.83) | 6-2 | m/z = 719.23($C_{52}H_{33}NOS$ = 719.89) |
| 6-3 | m/z = 719.23($C_{52}H_{33}NOS$ = 719.89) | 6-4 | m/z = 745.24($C_{54}H_{35}NOS$ = 745.93) |
| 6-5 | m/z = 785.28($C_{52}H_{33}NOS$ = 785.99) | 6-6 | m/z = 909.31($C_{67}H_{43}NOS$ = 910.13) |
| 6-7 | m/z = 907.29($C_{62}H_{41}NOS$ = 908.11) | 6-8 | m/z = 769.24($C_{56}H_{35}NOS$ = 769.95) |
| 6-9 | m/z = 769.24($C_{56}H_{35}NOS$ = 769.95) | 6-10 | m/z = 795.26($C_{58}H_{32}NOS$ = 795.99) |
| 6-11 | m/z = 835.26($C_{61}H_{41}NOS$ = 836.05) | 6-12 | m/z = 959.32($C_{21}H_{45}NOS$ = 960.19) |
| 6-13 | m/z = 957.31($C_{71}H_{43}NOS$ = 958.17) | 6-14 | m/z = 769.24($C_{56}H_{35}NOS$ = 769.95) |
| 6-15 | m/z = 795.26($C_{58}H_{32}NOS$ = 795.99) | 6-16 | m/z = 835.29($C_{61}H_{41}NOS$ = 836.05) |
| 6-17 | m/z = 959.32($C_{21}H_{45}NOS$ = 960.19) | 6-18 | m/z = 957.31($C_{71}H_{43}NOS$ = 958.17) |
| 6-19 | m/z = 821.28($C_{60}H_{33}NOS$ = 822.02) | 6-20 | m/z = 861.31($C_{63}H_{43}NOS$ = 862.09) |
| 6-21 | m/z = 985.34($C_{23}H_{42}NOS$ = 986.23) | 6-22 | m/z = 983.32($C_{23}H_{45}NOS$ = 984.21) |
| 6-23 | m/z = 821.28($C_{60}H_{33}NOS$ = 822.02) | 6-24 | m/z = 921.31($C_{68}H_{43}NOS$ = 922.14) |
| 6-25 | m/z = 921.31($C_{68}H_{43}NOS$ = 922.14) | 6-26 | m/z = 822.27($C_{53}H_{38}N_2OS$ = 823.01) |
| 6-27 | m/z = 823.27($C_{58}H_{32}N_3OS$ = 824.00) | 6-28 | m/z = 897.31($C_{66}H_{43}NOS$ = 898.12) |
| 7-1 | m/z = 685.19($C_{48}H_{31}NS_2$ = 685.90) | 7-2 | m/z = 735.21($C_{52}H_{33}NS_2$ = 735.96) |
| 7-3 | m/z = 735.21($C_{52}H_{33}NS_2$ = 735.96) | 7-4 | m/z = 761.22($C_{54}H_{35}NS_2$ = 761.99) |
| 7-5 | m/z = 769.30($C_{52}H_{33}NO_2$ = 769.93) | 7-6 | m/z = 893.33($C_{62}H_{43}NO_2$ = 894.06) |
| 7-7 | m/z = 907.29($C_{62}H_{41}NOS$ = 908.11) | 7-8 | m/z = 469.24($C_{56}H_{35}NOS$ = 769.95) |
| 7-9 | m/z = 852.26($C_{60}H_{40}N_2S_2$ = 853.10) | 7-10 | m/z = 1052.33($C_{26}H_{48}N_2S_2$ = 1053.34) |
| 7-11 | m/z = 1052.33($C_{26}H_{48}N_2S_2$ = 1053.34) | 7-12 | m/z = 1156.39($C_{84}H_{56}N_2S_2$ = 1157.49) |
| 7-13 | m/z = 820.31($C_{60}H_{40}N_2O_2$ = 820.97) | 7-14 | m/z = 1020.37($C_{26}H_{48}N_2O_2$ = 1021.21) |
| 7-15 | m/z = 1020.37($C_{26}H_{48}N_2O_2$ = 1021.21) | 7-16 | m/z = 1124.43($C_{84}H_{56}N_2O_2$ = 1125.36) |
| 7-17 | m/z = 836.29($C_{60}H_{40}N_2OS$ = 837.04) | 7-18 | m/z = 1036.35($C_{26}H_{48}N_2OS$ = 1037.27) |
| 7-19 | m/z = 1036.35($C_{26}H_{48}N_2OS$ = 1037.27) | 7-20 | m/z = 1140.41($C_{84}H_{56}N_2OS$ = 1141.42) |
| 7-21 | m/z = 1268.42($C_{93}H_{60}N_2S_2$ = 1269.61) | 7-22 | m/z = 1166.37($C_{85}H_{54}N_2S_2$ = 1167.48) |
| 7-23 | m/z = 1140.41($C_{84}H_{56}N_2OS$ = 1141.42) | 7-24 | m/z = 1324.50($C_{100}H_{64}N_2O_2$ = 1325.6) |

Fabrication and Evaluation of Organic Electronic Element

[Test Example 1] Green Organic Light Emitting Diode (a Hole Transport Layer)

Organic light emitting diodes (OLEDs) were fabricated according to a conventional method by using a synthesized compound as a hole transport layer material. First, an ITO layer (anode) was formed on a glass substrate, and a film of $N^1$-(naphthalen-2-yl)-$N^4$,$N^4$-bis(4-(naphthalen-2-yl(phenyl)amino)phenyl)-$N^1$-phenylbenzene-1,4-diamine (hereinafter, "2-TNATA") was vacuum-deposited on the ITO layer to form a hole injection layer with a thickness of 60 nm. Subsequently, a film of the compound 1-1 of the present invention was vacuum-deposited on the hole injection layer to form a hole transport layer with a thickness of 60 nm. Subsequently, a light emitting layer with a thickness of 30 nm was deposited on the hole transport layer by doping the hole transport layer with the 4,4'-N,N'-dicarbazole-biphenyl (hereinafter, "CBP") as a host material and tris(2-phenylpyridine)-iridium (hereinafter, "Ir(ppy)$_3$") as a dopant material in a weight ratio of 90:10. Next, a film of ((1,1'-bisphenyl)-4-olato)bis(2-methyl-8-quinolinolato)aluminum (hereinafter, "BAlq") was vacuum-deposited with a thickness of 10 nm on the light emitting layer to form a hole blocking layer, and a film of tris(8-quinolinolato)aluminum (hereinafter, "Alq$_3$") was formed with a thickness of 40 nm to form an electron transport layer. Next, LiF as halogenated alkali metal was deposited with a thickness of 0.2 nm on the electron transport layer to form an electron injection layer, and then Al was deposited with a thickness of 150 nm on the electron injection layer to form a cathode. In this way, the OLED was completed.

[Test Example 21] to [Test Example 138] Green Organic Light Emitting Diode (a Hole Transport Layer)

The OLED was manufactured in the same manner as described in Test Example 1, except that any one of the compounds 1-2 to 1-28, 2-1 to 2-28, 3-1 to 3-28, 4-1 to 4-28, 5-1, 5-2, 6-19 to 6-23, and 7-1 to 7-20 of the present invention in the Table 4 below was used as the hole transport layer material, instead of the inventive compound 1-1.

[Comparative Example 1] Green Organic Light Emitting Diode (a Hole Transport Layer)

An OLED was manufactured in the same manner as described in Test Example 1, except that Comparative Compound A represented below was used as the hole transport layer material, instead of the inventive compound 1-1.

<Comparative Compound A>

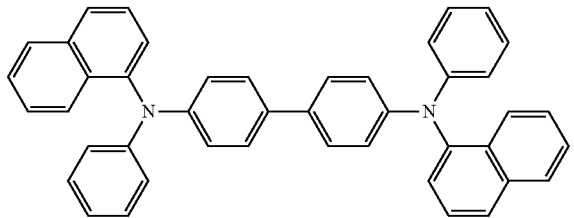

[Comparative Example 2] Green Organic Light Emitting Diode (a Hole Transport Layer)

An OLED was manufactured in the same manner as described in Test Example 1, except that Comparative Compound B represented below was used as the hole transport layer material, instead of the inventive compound 1-1.

<Comparative Compound B>

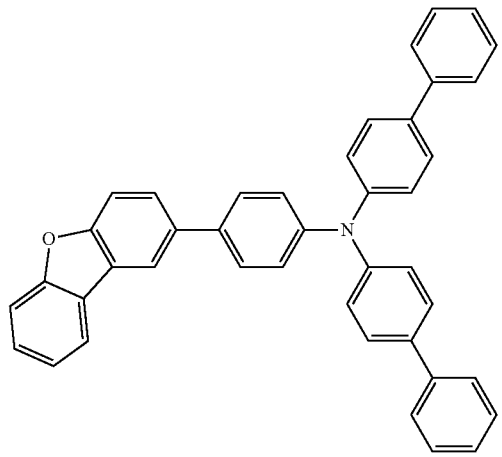

[Comparative Example 3] Green Organic Light Emitting Diode (a Hole Transport Layer)

An OLED was manufactured in the same manner as described in Test Example 1, except that Comparative Compound C represented below was used as the hole transport layer material, instead of the inventive compound 1-1.

<Comparative Compound C>

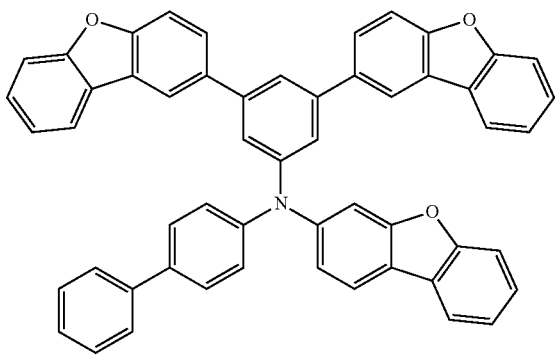

[Comparative Example 4] Green Organic Light Emitting Diode (a Hole Transport Layer)

An OLED was manufactured in the same manner as described in Test Example 1, except that Comparative Compound D represented below was used as the hole transport layer material, instead of the inventive compound 1-1.

<Comparative Compound D>

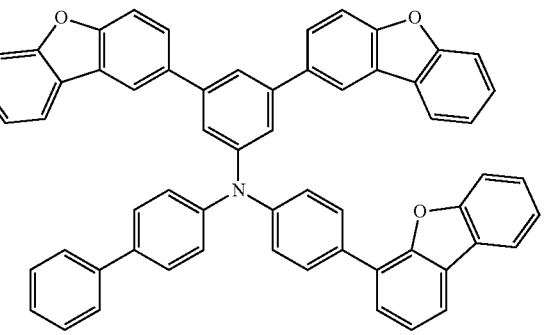

A forward bias DC voltage was applied to each of the OLEDs manufactured through Test Examples 1 to 138 and Comparative Example 1 to 4, and electro-luminescence (EL) characteristics of the OLED were measured by PR-650 (Photoresearch). Also, T95 life span was measured by life span measuring equipment (Mcscience) at a reference brightness of 5000 cd/m$^2$. Table 4 below shows evaluation results of OLEDs manufactured Test Examples and Comparative Examples.

TABLE 4

| | Compound | Voltage (V) | Current Density (mA/cm$^2$) | Brightness (cd/m$^2$) | Efficiency (cd/A) | Lifetime T(95) | CIE (x, y) |
|---|---|---|---|---|---|---|---|
| Com.Ex(1) | Com. Com. A | 6.4 | 20.8 | 5000.0 | 24.0 | 60.2 | (0.31, 0.60) |
| Com.Ex(2) | Com. Com. B | 6.0 | 14.8 | 5000.0 | 33.8 | 78.3 | (0.31, 0.61) |
| Com.Ex(3) | Com. Com. C | 6.2 | 16.5 | 5000.0 | 30.2 | 72.5 | (0.31, 0.60) |
| Com.Ex(4) | Com. Com. D | 6.1 | 18.0 | 5000.0 | 27.8 | 75.5 | (0.33, 0.61) |
| Ex.(1) | Com.(1-1) | 5.1 | 9.8 | 5000.0 | 50.9 | 94.3 | (0.30, 0.60) |
| Ex.(2) | Com.(1-2) | 5.2 | 9.6 | 5000.0 | 52.1 | 105.5 | (0.31, 0.61) |
| Ex.(3) | Com.(1-3) | 5.1 | 9.7 | 5000.0 | 51.3 | 123.5 | (0.31, 0.60) |
| Ex.(4) | Com.(1-4) | 5.1 | 9.5 | 5000.0 | 52.5 | 91.6 | (0.33, 0.61) |
| Ex.(5) | Com.(1-5) | 5.2 | 9.2 | 5000.0 | 54.6 | 114.7 | (0.32, 0.61) |
| Ex.(6) | Com.(1-6) | 5.1 | 9.9 | 5000.0 | 50.7 | 142.3 | (0.33, 0.60) |
| Ex.(7) | Com.(1-7) | 5.2 | 9.3 | 5000.0 | 54.0 | 131.4 | (0.32, 0.61) |
| Ex.(8) | Com.(1-8) | 5.2 | 10.0 | 5000.0 | 50.1 | 126.9 | (0.31, 0.60) |
| Ex.(9) | Com.(1-9) | 5.1 | 9.8 | 5000.0 | 51.0 | 94.1 | (0.31, 0.61) |
| Ex.(10) | Com.(1-10) | 5.1 | 9.3 | 5000.0 | 53.8 | 108.9 | (0.31, 0.60) |
| Ex.(11) | Com.(1-11) | 5.1 | 9.4 | 5000.0 | 53.0 | 98.2 | (0.33, 0.61) |
| Ex.(12) | Com.(1-12) | 5.1 | 9.2 | 5000.0 | 54.6 | 111.1 | (0.30, 0.60) |
| Ex.(13) | Com.(1-13) | 5.2 | 9.7 | 5000.0 | 51.5 | 122.9 | (0.31, 0.61) |
| Ex.(14) | Com.(1-14) | 5.0 | 9.4 | 5000.0 | 53.3 | 106.5 | (0.31, 0.60) |
| Ex.(15) | Com.(1-15) | 5.1 | 9.7 | 5000.0 | 51.3 | 98.0 | (0.33, 0.61) |
| Ex.(16) | Com.(1-16) | 5.1 | 10.0 | 5000.0 | 50.0 | 149.1 | (0.32, 0.61) |
| Ex.(17) | Com.(1-17) | 5.1 | 9.6 | 5000.0 | 52.2 | 145.2 | (0.33, 0.60) |
| Ex.(18) | Com.(1-18) | 5.1 | 10.0 | 5000.0 | 50.1 | 133.0 | (0.32, 0.61) |
| Ex.(19) | Com.(1-19) | 5.1 | 9.3 | 5000.0 | 53.5 | 138.9 | (0.31, 0.60) |
| Ex.(20) | Com.(1-20) | 5.0 | 9.9 | 5000.0 | 50.5 | 110.3 | (0.31, 0.61) |
| Ex.(21) | Com.(1-21) | 5.2 | 9.3 | 5000.0 | 54.1 | 102.9 | (0.31, 0.60) |
| Ex.(22) | Com.(1-22) | 5.1 | 9.2 | 5000.0 | 54.2 | 135.7 | (0.33, 0.61) |
| Ex.(23) | Com.(1-23) | 5.0 | 9.6 | 5000.0 | 52.3 | 120.5 | (0.30, 0.60) |
| Ex.(24) | Com.(1-24) | 5.0 | 9.7 | 5000.0 | 51.3 | 111.4 | (0.31, 0.61) |
| Ex.(25) | Com.(1-25) | 5.1 | 9.5 | 5000.0 | 52.8 | 115.7 | (0.31, 0.60) |
| Ex.(26) | Com.(1-26) | 5.1 | 9.8 | 5000.0 | 50.9 | 91.4 | (0.33, 0.61) |
| Ex.(27) | Com.(1-27) | 5.0 | 9.3 | 5000.0 | 54.0 | 127.4 | (0.32, 0.61) |
| Ex.(28) | Com.(1-28) | 5.2 | 9.6 | 5000.0 | 52.2 | 128.1 | (0.33, 0.60) |
| Ex.(29) | Com.(2-1) | 5.5 | 11.2 | 5000.0 | 44.7 | 124.6 | (0.31, 0.61) |
| Ex.(30) | Com.(2-2) | 5.5 | 11.8 | 5000.0 | 42.5 | 122.1 | (0.31, 0.60) |
| Ex.(31) | Com.(2-3) | 5.5 | 11.5 | 5000.0 | 43.4 | 117.3 | (0.33, 0.61) |
| Ex.(32) | Com.(2-4) | 5.4 | 12.1 | 5000.0 | 41.4 | 113.0 | (0.32, 0.61) |
| Ex.(33) | Com.(2-5) | 5.4 | 11.3 | 5000.0 | 44.2 | 99.7 | (0.33, 0.60) |
| Ex.(34) | Com.(2-6) | 5.4 | 11.6 | 5000.0 | 43.0 | 99.9 | (0.32, 0.61) |
| Ex.(35) | Com.(2-7) | 5.4 | 11.2 | 5000.0 | 44.6 | 123.8 | (0.31, 0.60) |
| Ex.(36) | Com.(2-8) | 5.4 | 11.4 | 5000.0 | 43.8 | 91.4 | (0.31, 0.60) |
| Ex.(37) | Com.(2-9) | 5.5 | 11.2 | 5000.0 | 44.5 | 132.4 | (0.31, 0.60) |
| Ex.(38) | Com.(2-10) | 5.4 | 11.7 | 5000.0 | 42.7 | 145.5 | (0.33, 0.61) |
| Ex.(39) | Com.(2-11) | 5.4 | 12.3 | 5000.0 | 40.5 | 115.0 | (0.30, 0.60) |
| Ex.(40) | Com.(2-12) | 5.5 | 11.4 | 5000.0 | 43.9 | 121.0 | (0.31, 0.61) |
| Ex.(41) | Com.(2-13) | 5.4 | 12.3 | 5000.0 | 40.8 | 133.8 | (0.31, 0.60) |
| Ex.(42) | Com.(2-14) | 5.4 | 12.2 | 5000.0 | 41.1 | 128.7 | (0.33, 0.61) |
| Ex.(43) | Com.(2-15) | 5.4 | 12.4 | 5000.0 | 40.2 | 130.8 | (0.32, 0.61) |
| Ex.(44) | Com.(2-16) | 5.5 | 12.0 | 5000.0 | 41.6 | 123.7 | (0.33, 0.61) |
| Ex.(45) | Com.(2-17) | 5.4 | 11.1 | 5000.0 | 44.8 | 112.9 | (0.32, 0.61) |
| Ex.(46) | Com.(2-18) | 5.4 | 11.3 | 5000.0 | 44.3 | 105.3 | (0.31, 0.60) |
| Ex.(47) | Com.(2-19) | 5.5 | 12.1 | 5000.0 | 41.2 | 132.8 | (0.31, 0.61) |
| Ex.(48) | Com.(2-20) | 5.4 | 12.4 | 5000.0 | 40.4 | 96.8 | (0.31, 0.60) |
| Ex.(49) | Com.(2-21) | 5.5 | 11.6 | 5000.0 | 43.0 | 103.8 | (0.33, 0.61) |
| Ex.(50) | Com.(2-22) | 5.5 | 11.7 | 5000.0 | 42.8 | 146.7 | (0.30, 0.60) |
| Ex.(51) | Com.(2-23) | 5.5 | 12.1 | 5000.0 | 41.5 | 147.5 | (0.31, 0.61) |
| Ex.(52) | Com.(2-24) | 5.5 | 12.3 | 5000.0 | 40.7 | 130.1 | (0.31, 0.60) |
| Ex.(53) | Com.(2-25) | 5.5 | 11.8 | 5000.0 | 42.2 | 96.2 | (0.33, 0.61) |
| Ex.(54) | Com.(2-26) | 5.4 | 12.4 | 5000.0 | 40.4 | 122.0 | (0.32, 0.61) |
| Ex.(55) | Com.(2-27) | 5.4 | 11.9 | 5000.0 | 42.0 | 106.4 | (0.33, 0.61) |
| Ex.(56) | Com.(2-28) | 5.5 | 11.2 | 5000.0 | 44.7 | 114.4 | (0.32, 0.61) |
| Ex.(57) | Com.(3-1) | 5.2 | 9.6 | 5000.0 | 52.2 | 129.2 | (0.31, 0.60) |
| Ex.(58) | Com.(3-2) | 5.1 | 9.1 | 5000.0 | 54.8 | 145.3 | (0.33, 0.61) |
| Ex.(59) | Com.(3-3) | 5.2 | 9.5 | 5000.0 | 52.6 | 148.5 | (0.30, 0.60) |
| Ex.(60) | Com.(3-4) | 5.1 | 9.7 | 5000.0 | 51.3 | 124.1 | (0.31, 0.61) |
| Ex.(61) | Com.(3-5) | 5.2 | 9.6 | 5000.0 | 51.8 | 125.6 | (0.31, 0.61) |
| Ex.(62) | Com.(3-6) | 5.1 | 10.0 | 5000.0 | 50.0 | 146.6 | (0.33, 0.61) |
| Ex.(63) | Com.(3-7) | 5.1 | 9.6 | 5000.0 | 52.1 | 103.9 | (0.32, 0.61) |
| Ex.(64) | Com.(3-8) | 5.1 | 9.1 | 5000.0 | 54.8 | 104.9 | (0.33, 0.61) |
| Ex.(65) | Com.(3-9) | 5.1 | 9.8 | 5000.0 | 51.1 | 141.7 | (0.32, 0.61) |
| Ex.(66) | Com.(3-10) | 5.2 | 9.9 | 5000.0 | 50.7 | 92.1 | (0.31, 0.60) |
| Ex.(67) | Com.(3-11) | 5.1 | 9.1 | 5000.0 | 54.9 | 140.3 | (0.31, 0.60) |
| Ex.(68) | Com.(3-12) | 5.1 | 9.1 | 5000.0 | 54.8 | 131.6 | (0.31, 0.60) |
| Ex.(69) | Com.(3-13) | 5.0 | 9.5 | 5000.0 | 52.8 | 125.3 | (0.33, 0.61) |
| Ex.(70) | Com.(3-14) | 5.1 | 9.9 | 5000.0 | 50.7 | 94.4 | (0.30, 0.60) |
| Ex.(71) | Com.(3-15) | 5.0 | 10.0 | 5000.0 | 50.2 | 130.3 | (0.31, 0.61) |
| Ex.(72) | Com.(3-16) | 5.1 | 9.8 | 5000.0 | 51.0 | 141.1 | (0.31, 0.60) |

TABLE 4-continued

| | Compound | Voltage (V) | Current Density (mA/cm²) | Brightness (cd/m²) | Efficiency (cd/A) | Lifetime T(95) | CIE (x, y) |
|---|---|---|---|---|---|---|---|
| Ex.(73) | Com.(3-17) | 5.1 | 9.9 | 5000.0 | 50.4 | 113.6 | (0.33, 0.61) |
| Ex.(74) | Com.(3-18) | 5.2 | 9.5 | 5000.0 | 52.9 | 119.3 | (0.32, 0.61) |
| Ex.(75) | Com.(3-19) | 5.1 | 9.3 | 5000.0 | 53.5 | 133.7 | (0.33, 0.61) |
| Ex.(76) | Com.(3-20) | 5.1 | 9.3 | 5000.0 | 53.5 | 112.3 | (0.30, 0.60) |
| Ex.(77) | Com.(3-21) | 5.1 | 9.5 | 5000.0 | 52.5 | 114.8 | (0.31, 0.60) |
| Ex.(78) | Com.(3-22) | 5.1 | 9.6 | 5000.0 | 51.8 | 92.2 | (0.31, 0.60) |
| Ex.(79) | Com.(3-23) | 5.1 | 9.6 | 5000.0 | 52.0 | 107.4 | (0.33, 0.61) |
| Ex.(80) | Com.(3-24) | 5.1 | 9.2 | 5000.0 | 54.4 | 127.4 | (0.32, 0.61) |
| Ex.(81) | Com.(3-25) | 5.1 | 9.6 | 5000.0 | 52.2 | 128.4 | (0.33, 0.60) |
| Ex.(82) | Com.(3-26) | 5.1 | 9.1 | 5000.0 | 54.8 | 103.6 | (0.32, 0.61) |
| Ex.(83) | Com.(3-27) | 5.1 | 9.5 | 5000.0 | 52.6 | 102.9 | (0.31, 0.60) |
| Ex.(84) | Com.(3-28) | 5.0 | 9.7 | 5000.0 | 51.3 | 105.1 | (0.31, 0.61) |
| Ex.(85) | Com.(4-1) | 5.4 | 11.6 | 5000.0 | 43.2 | 141.1 | (0.31, 0.60) |
| Ex.(86) | Com.(4-2) | 5.4 | 11.4 | 5000.0 | 43.8 | 148.2 | (0.33, 0.61) |
| Ex.(87) | Com.(4-3) | 5.4 | 11.1 | 5000.0 | 44.9 | 121.6 | (0.30, 0.60) |
| Ex.(88) | Com.(4-4) | 5.4 | 12.4 | 5000.0 | 40.2 | 138.3 | (0.31, 0.61) |
| Ex.(89) | Com.(4-5) | 5.4 | 11.5 | 5000.0 | 43.4 | 135.4 | (0.31, 0.61) |
| Ex.(90) | Com.(4-6) | 5.5 | 12.3 | 5000.0 | 40.6 | 143.5 | (0.33, 0.61) |
| Ex.(91) | Com.(4-7) | 5.4 | 11.5 | 5000.0 | 43.3 | 124.1 | (0.32, 0.61) |
| Ex.(92) | Com.(4-8) | 5.5 | 11.6 | 5000.0 | 43.2 | 107.6 | (0.33, 0.60) |
| Ex.(93) | Com.(4-9) | 5.5 | 11.2 | 5000.0 | 44.8 | 90.8 | (0.31, 0.61) |
| Ex.(94) | Com.(4-10) | 5.5 | 12.1 | 5000.0 | 41.2 | 148.4 | (0.31, 0.60) |
| Ex.(95) | Com.(4-11) | 5.5 | 11.6 | 5000.0 | 43.2 | 105.3 | (0.33, 0.61) |
| Ex.(96) | Com.(4-12) | 5.5 | 12.3 | 5000.0 | 40.8 | 125.2 | (0.32, 0.61) |
| Ex.(97) | Com.(4-13) | 5.4 | 11.8 | 5000.0 | 42.3 | 135.5 | (0.33, 0.60) |
| Ex.(98) | Com.(4-14) | 5.5 | 11.1 | 5000.0 | 45.0 | 104.8 | (0.32, 0.61) |
| Ex.(99) | Com.(4-15) | 5.4 | 11.5 | 5000.0 | 43.5 | 104.3 | (0.31, 0.61) |
| Ex.(100) | Com.(4-16) | 5.5 | 12.1 | 5000.0 | 41.4 | 132.0 | (0.31, 0.61) |
| Ex.(101) | Com.(4-17) | 5.5 | 11.5 | 5000.0 | 43.7 | 143.1 | (0.31, 0.60) |
| Ex.(102) | Com.(4-18) | 5.4 | 12.0 | 5000.0 | 41.6 | 120.6 | (0.33, 0.61) |
| Ex.(103) | Com.(4-19) | 5.5 | 12.1 | 5000.0 | 41.5 | 141.9 | (0.30, 0.60) |
| Ex.(104) | Com.(4-20) | 5.5 | 11.2 | 5000.0 | 44.5 | 114.0 | (0.31, 0.61) |
| Ex.(105) | Com.(4-21) | 5.5 | 12.4 | 5000.0 | 40.3 | 104.5 | (0.31, 0.61) |
| Ex.(106) | Com.(4-22) | 5.4 | 11.3 | 5000.0 | 44.3 | 132.7 | (0.33, 0.61) |
| Ex.(107) | Com.(4-23) | 5.4 | 12.1 | 5000.0 | 41.3 | 114.5 | (0.33, 0.61) |
| Ex.(108) | Com.(4-24) | 5.5 | 12.3 | 5000.0 | 40.6 | 106.5 | (0.30, 0.60) |
| Ex.(109) | Com.(4-25) | 5.4 | 11.7 | 5000.0 | 42.7 | 139.5 | (0.31, 0.61) |
| Ex.(110) | Com.(4-26) | 5.5 | 12.0 | 5000.0 | 41.7 | 149.0 | (0.31, 0.60) |
| Ex.(111) | Com.(4-27) | 5.4 | 12.3 | 5000.0 | 40.7 | 109.7 | (0.33, 0.61) |
| Ex.(112) | Com.(4-28) | 5.5 | 12.0 | 5000.0 | 41.6 | 135.6 | (0.32, 0.61) |
| Ex.(113) | Com.(5-1) | 5.0 | 9.2 | 5000.0 | 54.4 | 141.1 | (0.31, 0.60) |
| Ex.(114) | Com.(5-2) | 5.4 | 11.8 | 5000.0 | 42.5 | 148.2 | (0.33, 0.61) |
| Ex.(115) | Com.(6-19) | 5.4 | 10.9 | 5000.0 | 46.0 | 121.6 | (0.30, 0.60) |
| Ex.(116) | Com.(6-20) | 5.3 | 11.0 | 5000.0 | 45.3 | 138.3 | (0.31, 0.61) |
| Ex.(117) | Com.(6-21) | 5.3 | 10.8 | 5000.0 | 46.2 | 135.4 | (0.31, 0.61) |
| Ex.(118) | Com.(6-22) | 5.4 | 11.0 | 5000.0 | 45.6 | 143.5 | (0.33, 0.61) |
| Ex.(119) | Com.(6-23) | 5.3 | 10.5 | 5000.0 | 47.6 | 124.1 | (0.32, 0.61) |
| Ex.(120) | Com.(7-1) | 5.1 | 9.6 | 5000.0 | 52.1 | 107.6 | (0.33, 0.60) |
| Ex.(121) | Com.(7-2) | 5.1 | 9.8 | 5000.0 | 50.8 | 90.8 | (0.31, 0.61) |
| Ex.(122) | Com.(7-3) | 5.0 | 9.4 | 5000.0 | 53.0 | 148.4 | (0.31, 0.61) |
| Ex.(123) | Com.(7-4) | 5.0 | 9.9 | 5000.0 | 50.4 | 105.3 | (0.33, 0.61) |
| Ex.(124) | Com.(7-5) | 5.5 | 11.5 | 5000.0 | 43.6 | 125.2 | (0.32, 0.61) |
| Ex.(125) | Com.(7-6) | 5.5 | 11.7 | 5000.0 | 42.8 | 135.5 | (0.33, 0.60) |
| Ex.(126) | Com.(7-7) | 5.4 | 10.5 | 5000.0 | 47.7 | 104.8 | (0.32, 0.61) |
| Ex.(127) | Com.(7-9) | 5.4 | 11.3 | 5000.0 | 44.3 | 104.3 | (0.31, 0.61) |
| Ex.(128) | Com.(7-10) | 5.4 | 11.5 | 5000.0 | 43.5 | 132.0 | (0.31, 0.61) |
| Ex.(129) | Com.(7-11) | 5.4 | 11.2 | 5000.0 | 44.7 | 143.1 | (0.31, 0.60) |
| Ex.(130) | Com.(7-12) | 5.4 | 11.6 | 5000.0 | 43.2 | 120.6 | (0.33, 0.61) |
| Ex.(131) | Com.(7-13) | 5.5 | 12.2 | 5000.0 | 40.9 | 141.9 | (0.30, 0.60) |
| Ex.(132) | Com.(7-14) | 5.5 | 12.2 | 5000.0 | 40.9 | 114.0 | (0.31, 0.61) |
| Ex.(133) | Com.(7-15) | 5.6 | 12.5 | 5000.0 | 40.1 | 104.5 | (0.31, 0.61) |
| Ex.(134) | Com.(7-16) | 5.5 | 12.3 | 5000.0 | 40.7 | 132.7 | (0.33, 0.61) |
| Ex.(135) | Com.(7-17) | 5.5 | 11.8 | 5000.0 | 42.5 | 114.5 | (0.33, 0.61) |
| Ex.(136) | Com.(7-18) | 5.5 | 11.7 | 5000.0 | 42.8 | 132.0 | (0.31, 0.60) |
| Ex.(137) | Com.(7-19) | 5.5 | 11.7 | 5000.0 | 42.9 | 128.5 | (0.33, 0.61) |
| Ex.(138) | Com.(7-20) | 5.5 | 11.8 | 5000.0 | 42.2 | 92.3 | (0.32, 0.61) |

As shown in Table 4 above, the OLEDs using the above compounds as materials for a hole transport layer, have reduced driving voltage and significantly improved luminous efficiency and lifespan.

This is explained that the compounds of the present invention bonding an amine group with two of dibenzofuran or dibenzothiophene substituted an aryl not a heteroaryl, than the comparative compounds like comparative compound A which is NPB, comparative compound B substituted one of dibenzofuran, and comparative compound C and D substituted three of dibenzofuran, have more proper HOMO and LUMO value and it is caused faster mobility by means of improving charge balance with adjacent layers. So, the OLEDs comprising the compounds of the present invention was obtained a reduced driving voltage and an improved lifespan.

Accordingly, it was shown that even with the same core, the chemical properties of the compounds and the element properties of the compounds depend on the substituent bonded to the core.

[Test Example 139] Blue Organic Light Emitting Diode (Emission-Auxiliary Layer)

Organic light emitting diodes (OLEDs) were fabricated according to a conventional method by using a synthesized compound as a hole transport layer material. First, an ITO layer (anode) was formed on a glass substrate, and a film of 2-TNATA was vacuum-deposited on the ITO layer to form a hole injection layer with a thickness of 60 nm. Subsequently, a film of 4,4-bis[N-(1-naphthyl)-N-phenylamino] biphenyl (hereinafter, "NPD") was vacuum-deposited on the hole injection layer to form a hole transport layer with a thickness of 60 nm. Subsequently, a film of the compound 1-1 of the present invention was vacuum-deposited on the hole injection layer to form a emission-auxiliary layer with a thickness of 20 nm. Subsequently, a light emitting layer with a thickness of 30 nm was deposited on the emission-auxiliary layer by using the 9,10-di(naphthalen-2-yl)anthracene as a host material and BD-052X (produced by Idemitsu kosan) as a dopant material in a weight ratio of 96:4.

Next, a film of BAlq was vacuum-deposited with a thickness of 10 nm on the light emitting layer to form a hole blocking layer, and a film of $Alq_3$ was formed with a thickness of 40 nm to form an electron transport layer. Next, LiF as halogenated alkali metal was deposited with a thickness of 0.2 nm on the electron transport layer to form an electron injection layer, and then Al was deposited with a thickness of 150 nm on the electron injection layer to form a cathode. In this way, the OLED was completed.

[Test Example 140] to [Test Example 183] Blue Organic Light Emitting Diode (an Emission-Auxiliary Layer)

The OLED was manufactured in the same manner as described in Test Example 139, except that any one of the compounds 1-2 to 1-7, 2-1 to 2-7, 3-1 to 3-7, 4-1 to 4-7, 6-1 to 6-5, and 7-9 to 7-20 of the present invention in the Table 5 below was used as the emission-auxiliary layer material, instead of the inventive compound 1-1.

[Comparative Example 5] Blue Organic Light Emitting Diode (an Emission-Auxiliary Layer)

An OLED was manufactured in the same manner as described in Test Example 139, except not to form the emission-auxiliary layer.

[Comparative Example 6] Blue Organic Light Emitting Diode (an Emission-Auxiliary Layer)

An OLED was manufactured in the same manner as described in Test Example 139, except that Comparative Compound B represented below was used as the emission-auxiliary layer material, instead of the inventive compound 1-1.

[Comparative Example 7] Blue Organic Light Emitting Diode (an Emission-Auxiliary Layer)

An OLED was manufactured in the same manner as described in Test Example 139, except that Comparative Compound C represented below was used as the emission-auxiliary layer material, instead of the inventive compound 1-1.

[Comparative Example 8] Blue Organic Light Emitting Diode (an Emission-Auxiliary Layer)

An OLED was manufactured in the same manner as described in Test Example 139, except that Comparative Compound D represented below was used as the emission-auxiliary layer material, instead of the inventive compound 1-1.

A forward bias DC voltage was applied to each of the OLEDs manufactured through Test Examples 139 to 183 and Comparative Example 5 to 8, and electro-luminescence (EL) characteristics of the OLED were measured by PR-650 (Photoresearch). Also, T95 life span was measured by life span measuring equipment (Mcscience) at a reference brightness of 5000 $cd/m^2$. Table 5 below shows evaluation results of OLEDs manufactured Test Examples and Comparative Examples.

TABLE 5

| | Compound | Voltage (V) | Current Density ($mA/cm^2$) | Brightness ($cd/m^2$) | Efficiency (cd/A) | Lifetime T(95) |
|---|---|---|---|---|---|---|
| Com.Ex(5) | — | 5.3 | 11.1 | 500.0 | 4.5 | 63.2 |
| Com.Ex(6) | Com. Com. B | 5.6 | 8.2 | 500.0 | 6.1 | 85.1 |
| Com.Ex(7) | Com. Com. C | 5.7 | 7.3 | 500.0 | 6.9 | 84.9 |
| Com.Ex(8) | Com. Com. D | 5.8. | 7.5 | 500.0 | 6.7 | 84.7 |
| Ex.(139) | Com.(1-1) | 5.4 | 3.9 | 500.0 | 12.9 | 94.9 |
| Ex.(140) | Com.(1-2) | 5.2 | 4.0 | 500.0 | 12.5 | 104.0 |
| Ex.(141) | Com.(1-3) | 5.3 | 3.9 | 500.0 | 12.9 | 137.8 |
| Ex.(142) | Com.(1-4) | 5.5 | 4.9 | 500.0 | 10.3 | 133.4 |
| Ex.(143) | Com.(1-5) | 5.3 | 4.7 | 500.0 | 10.7 | 118.9 |
| Ex.(144) | Com.(1-6) | 5.4 | 4.8 | 500.0 | 10.5 | 114.3 |
| Ex.(145) | Com.(1-7) | 5.2 | 4.2 | 500.0 | 11.8 | 113.3 |
| Ex.(146) | Com.(2-1) | 5.2 | 5.6 | 500.0 | 8.9 | 114.2 |
| Ex.(147) | Com.(2-2) | 5.2 | 5.9 | 500.0 | 8.4 | 132.8 |
| Ex.(148) | Com.(2-3) | 5.3 | 6.1 | 500.0 | 8.2 | 108.6 |
| Ex.(149) | Com.(2-4) | 5.3 | 6.0 | 500.0 | 8.3 | 137.0 |
| Ex.(150) | Com.(2-5) | 5.4 | 5.8 | 500.0 | 8.6 | 134.6 |
| Ex.(151) | Com.(2-6) | 5.3 | 5.7 | 500.0 | 8.7 | 122.1 |
| Ex.(152) | Com.(2-7) | 5.2 | 6.2 | 500.0 | 8.1 | 103.0 |
| Ex.(153) | Com.(3-1) | 5.5 | 4.7 | 500.0 | 10.6 | 130.6 |
| Ex.(154) | Com.(3-2) | 5.4 | 4.0 | 500.0 | 12.6 | 115.6 |

TABLE 5-continued

| | Compound | Voltage (V) | Current Density (mA/cm²) | Brightness (cd/m²) | Efficiency (cd/A) | Lifetime T(95) |
|---|---|---|---|---|---|---|
| Ex.(155) | Com.(3-3) | 5.3 | 4.3 | 500.0 | 11.7 | 138.9 |
| Ex.(156) | Com.(3-4) | 5.2 | 4.8 | 500.0 | 10.5 | 116.2 |
| Ex.(157) | Com.(3-5) | 5.2 | 4.5 | 500.0 | 11.1 | 113.4 |
| Ex.(158) | Com.(3-6) | 5.3 | 4.8 | 500.0 | 10.5 | 136.5 |
| Ex.(159) | Com.(3-7) | 5.4 | 4.1 | 500.0 | 12.1 | 105.4 |
| Ex.(160) | Com.(4-1) | 5.4 | 5.6 | 500.0 | 8.9 | 136.4 |
| Ex.(161) | Com.(4-2) | 5.5 | 5.8 | 500.0 | 8.6 | 115.3 |
| Ex.(162) | Com.(4-3) | 5.4 | 5.7 | 500.0 | 8.8 | 123.5 |
| Ex.(163) | Com.(4-4) | 5.4 | 5.6 | 500.0 | 8.9 | 132.1 |
| Ex.(164) | Com.(4-5) | 5.3 | 5.7 | 500.0 | 8.7 | 135.4 |
| Ex.(165) | Com.(4-6) | 5.3 | 5.6 | 500.0 | 8.9 | 126.7 |
| Ex.(166) | Com.(4-7) | 5.3 | 5.6 | 500.0 | 9.0 | 129.1 |
| Ex.(167) | Com.(6-1) | 5.2 | 5.4 | 500.0 | 9.2 | 138.0 |
| Ex.(168) | Com.(6-2) | 5.3 | 5.0 | 500.0 | 10.0 | 116.0 |
| Ex.(169) | Com.(6-3) | 5.5 | 5.2 | 500.0 | 9.7 | 138.4 |
| Ex.(170) | Com.(6-4) | 5.5 | 5.2 | 500.0 | 9.6 | 119.1 |
| Ex.(171) | Com.(6-5) | 5.5 | 5.4 | 500.0 | 9.2 | 114.2 |
| Ex.(172) | Com.(7-9) | 5.4 | 3.4 | 500.0 | 14.8 | 124.7 |
| Ex.(173) | Com.(7-10) | 5.3 | 3.4 | 500.0 | 14.6 | 103.2 |
| Ex.(174) | Com.(7-11) | 5.5 | 3.4 | 500.0 | 14.9 | 115.4 |
| Ex.(175) | Com.(7-12) | 5.3 | 3.4 | 500.0 | 14.7 | 137.7 |
| Ex.(176) | Com.(7-13) | 5.4 | 3.9 | 500.0 | 13.0 | 118.8 |
| Ex.(177) | Com.(7-14) | 5.5 | 3.9 | 500.0 | 12.8 | 121.9 |
| Ex.(178) | Com.(7-15) | 5.3 | 3.9 | 500.0 | 12.9 | 113.8 |
| Ex.(179) | Com.(7-16) | 5.3 | 4.1 | 500.0 | 12.3 | 105.7 |
| Ex.(180) | Com.(7-17) | 5.4 | 3.7 | 500.0 | 13.5 | 130.1 |
| Ex.(181) | Com.(7-18) | 5.5 | 3.8 | 500.0 | 13.1 | 127.5 |
| Ex.(182) | Com.(7-19) | 5.4 | 3.6 | 500.0 | 13.8 | 114.5 |
| Ex.(183) | Com.(7-20) | 5.5 | 3.6 | 500.0 | 13.7 | 134.6 |

As shown in Table 5 above, the OLEDs using the above compounds as materials for the emitting auxiliary layer, has significantly improved luminous efficiency and lifespan compared to the OLEDs of the comparative Examples which don't form the emitting auxiliary layer, but has similar driving voltage.

Also, in the case where the OLEDs using the compounds of the present invention bonding an amine group with two of dibenzofuran or dibenzothiophene substituted an aryl not a hetero aryl were used as materials for the emitting auxiliary layer than the OLEDs using comparative compound B substituted one of dibenzofuran, and comparative compound C and D substituted three of dibenzofuran, significantly improved luminous efficiency and a lifespan was obtained.

This is, when the compounds of the present invention were used as the emitting auxiliary layer, deep HOMO energy level what is inherent properties of the compound of the present invention was caused a charge balance of between hole and electron in the lighting emitting layer due to move suitable amounts of the hole from in a hole transport layer to a lighting emitting layer, and also efficiency and lifespan were improved because of that the high T1 value block the movement of electrons from the light emitting layer to the hole transport layer and prevent the emission to interface of the hole transport layer.

Although exemplary embodiments of the present invention have been described for illustrative purposes, those skilled in the art will appreciate that various modifications, additions and substitutions are possible, without departing from the scope and spirit of the invention as disclosed in the accompanying claims. Therefore, the embodiment disclosed in the present invention is intended to illustrate the scope of the technical idea of the present invention, and the scope of the present invention is not limited by the embodiment. The scope of the present invention shall be construed on the basis of the accompanying claims, and it shall be construed that all of the technical ideas included within the scope equivalent to the claims belong to the present invention.

The invention claimed is:

1. A compound of Formula 1:

[Formula 1]

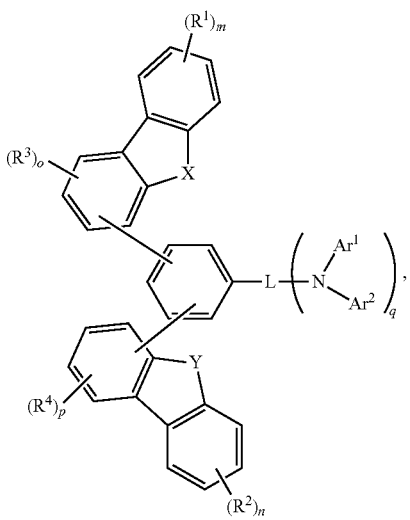

wherein:
X and Y are independently O or S,
$Ar^1$ and $Ar^2$ are independently a $C_6$-$C_{60}$ aryl group or a fluorenyl group with the proviso that at least one of $Ar^1$ and $Ar^2$ is a fluorenyl group,
q is 1,
L is selected from the group consisting of a $C_6$-$C_{60}$ arylene group, a fluorenylene group, a fused ring group of a $C_3$-$C_{60}$ aliphatic ring and a $C_6$-$C_{60}$ aromatic ring, and a $C_2$-$C_{60}$ heterocyclic group containing at least one heteroatom selected from the group consisting of O, N, S, Si, and P, $R^1$ to $R^4$ are (i) each independently selected from the group consisting of hydrogen, deuterium, halogen, a $C_6$-$C_{60}$ aryl group, a fluorenyl group, a $C_2$-$C_{60}$ heterocyclic group containing at least one heteroatom selected from the group consisting of O, N, S, Si, and P, a fused ring group of a $C_3$-$C_{60}$ aliphatic ring and a $C_6$-$C_{60}$ aromatic ring, $C_1$-$C_{50}$ alkyl group, $C_2$-$C_{20}$ alkenyl group, $C_2$-$C_{20}$ alkynyl group, $C_1$-$C_{30}$ alkoxy group, $C_6$-$C_{30}$ aryloxy group, and —L'—N($R^a$)($R^b$), or (ii) at least one of adjacent $R^1$s to $R^4$s, when m, n, o and p are each an integer of 2 or more, optionally forms a ring, and $R^1$ to $R^4$ not forming a ring are the same as defined above, m and n are each an integer from 0 to 4, o and p are each an integer of 0 to 3, and where m, n, o or p is an integer of 2 or more, plural $R^1$s, $R^2$s, $R^3$s or $R^4$s are the same as or different from each other, L' is selected from the group consisting of a single bond, a $C_6$-$C_{60}$ arylene group, a fluorenylene group, a fused ring group of a $C_3$-$C_{60}$ aliphatic ring and a $C_6$-$C_{60}$ aromatic ring, and a $C_2$-$C_{60}$ heterocyclic group containing at least one heteroatom selected from the group consisting of O, N, S, Si, and P, $R^a$ and $R^b$ are each independently selected from the group consisting of a $C_6$-$C_{60}$ aryl group, a fluorenyl group, a fused ring group of a $C_3$-$C_{60}$ aliphatic ring and a $C_6$-$C_{60}$ aromatic ring, and a $C_2$-$C_{60}$ heterocyclic group containing at least one heteroatom selected from the group consisting of O, N, S, Si, and P, and where $Ar^1$ and $Ar^2$ are the aryl group or fluorenyl group, $Ar^1$ and $Ar^2$ are each optionally substituted with one or more substituents selected from the group consisting of deuterium, halogen, a silane group, a siloxane group, a boron group, a germanium group, a cyano group, a nitro group, a $C_1$-$C_{20}$ alkylthio group, a $C_1$-$C_{20}$ alkoxy group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted by deuterium, a fluorenyl group, a $C_3$-$C_{20}$ cycloalkyl group, a $C_7$-$C_{20}$ arylalkyl group, and a $C_8$-$C_{20}$ arylalkenyl group, where L is the arylene group, fluorenylene group, fused ring group or hetero cyclic group, L is optionally substituted with one or more substituents selected from the group consisting of deuterium, halogen, a silane group, a siloxane group, a boron group, a germanium group, a cyano group, a nitro group, a $C_1$-$C_{20}$ alkylthio group, a $C_1$-$C_{20}$ alkoxy group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_2$-$C_{20}$ heterocyclic group containing at least one heteroatom selected from the group consisting of O, N, S, Si, and P, a $C_3$-$C_{20}$ cycloalkyl group, a $C_7$-$C_{20}$ arylalkyl group, and a $C_8$-$C_{20}$ arylalkenyl group, where $R^1$ to $R^4$ are the aryl group, fluorenyl group, hetero cyclic group, fused ring group, alkyl group, alkenyl group, alkynyl group, alkoxy group, or aryloxy group, $R^1$ to $R^4$ are each optionally substituted with one or more substituents selected from the group consisting of deuterium, halogen, a silane group, a siloxane group, a boron group, a germanium group, a cyano group, a nitro group, a $C_1$-$C_{20}$ alkylthio group, a $C_1$-$C_{20}$ alkoxy group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_2$-$C_{20}$ heterocyclic group containing at least one heteroatom selected from the group consisting of O, N, S, Si, and P, a $C_3$-$C_{20}$ cycloalkyl group, a $C_7$-$C_{20}$ arylalkyl group, and a $C_8$-$C_{20}$ arylalkenyl group.

2. The compound of claim 1, represented by one of Formulas 2 to 5:

[Formula 2]

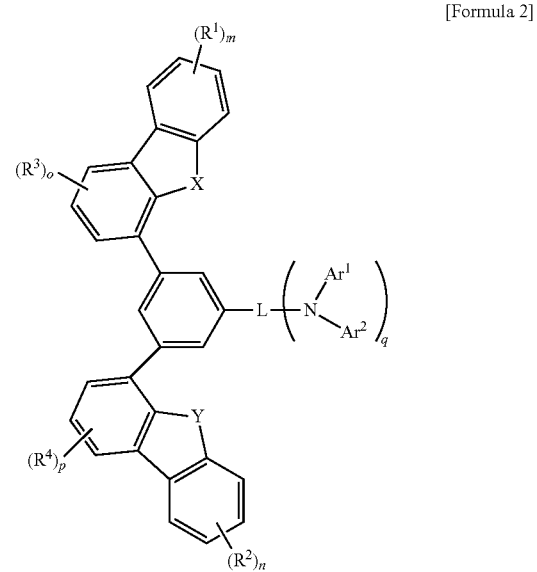

[Formula 3]

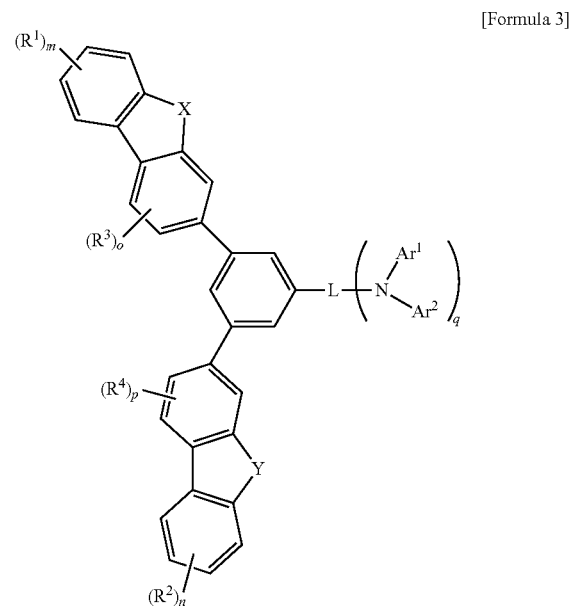

[Formula 4]
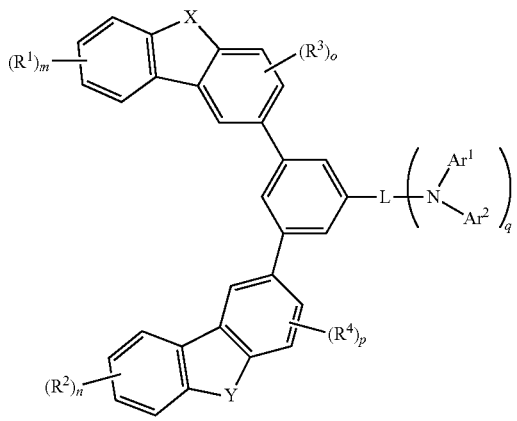
[Formula 5]
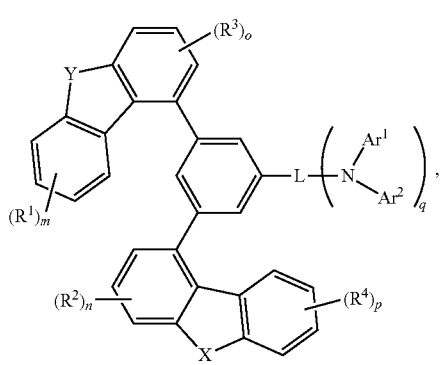
wherein X, Y, Ar¹, Ar², L, R¹ to R⁴, m, n, o, p and q are the same as defined in claim 1.
3. The compound of claim 1, selected from the group consisting of:
1-5
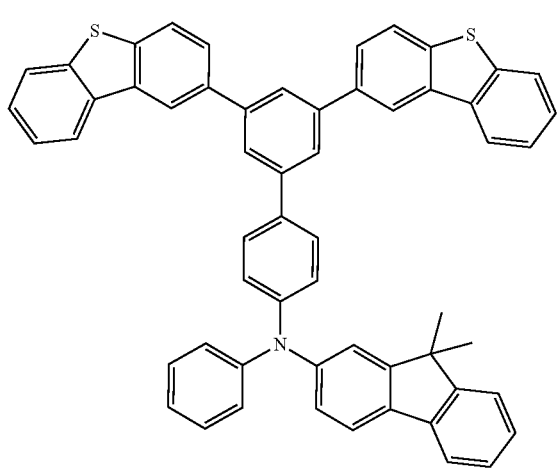
1-6
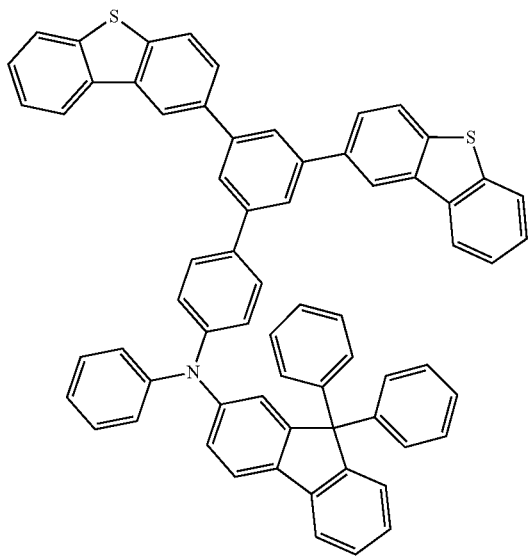
1-7
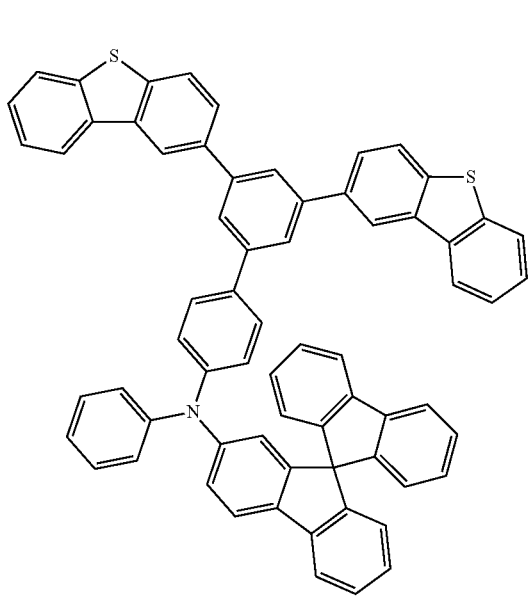
1-11
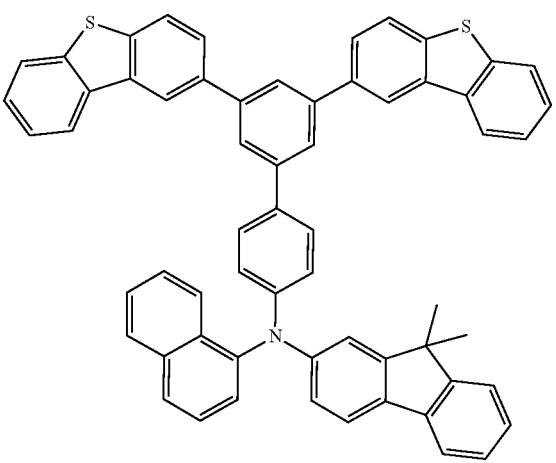

1-12
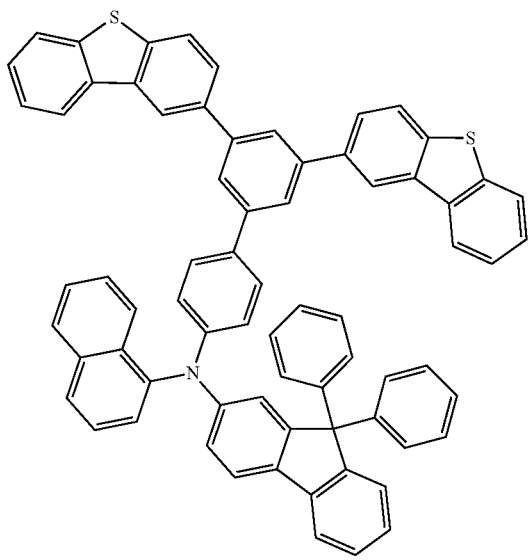
1-13
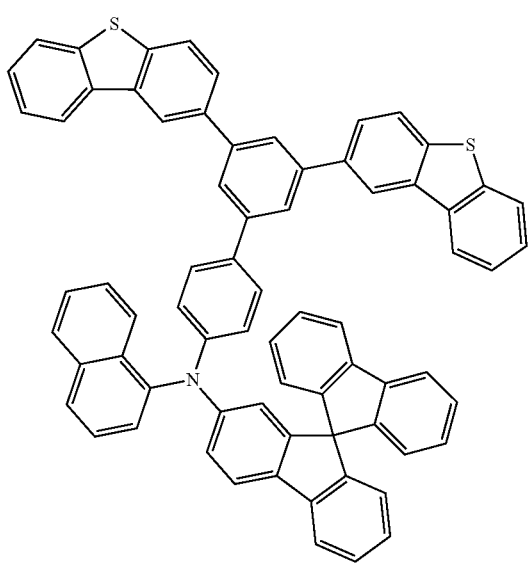
1-16
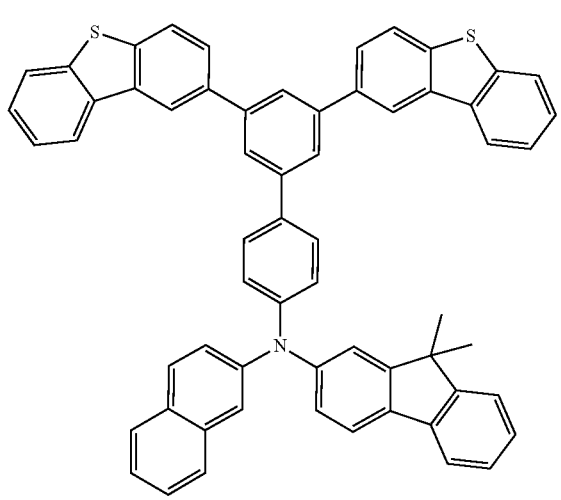
1-17
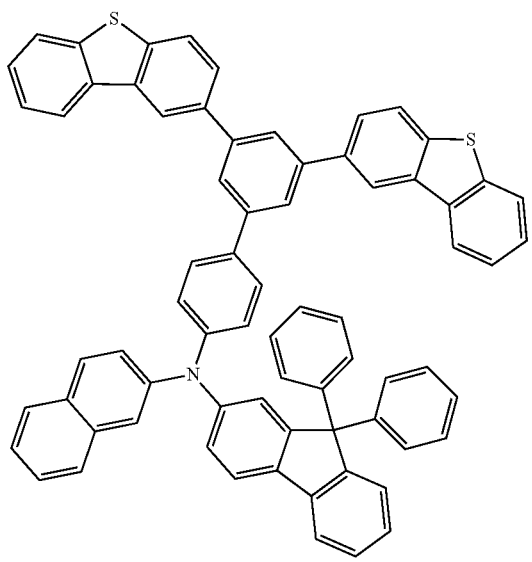
1-18
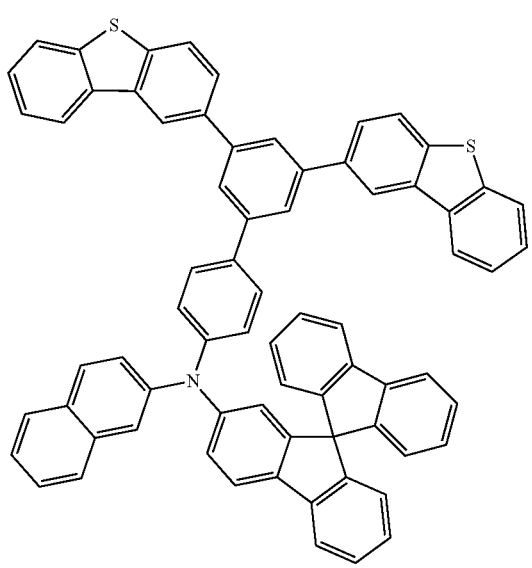
1-20
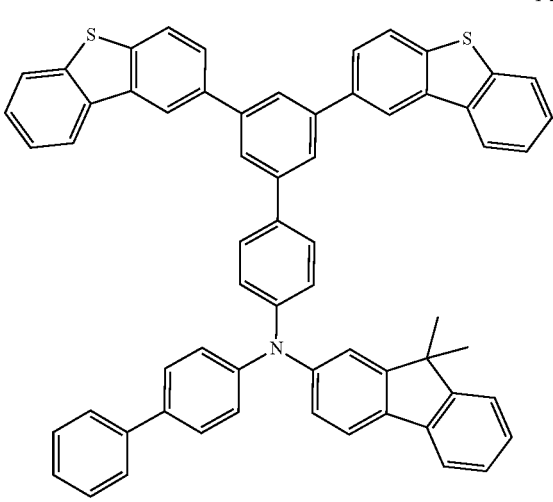

-continued
1-21
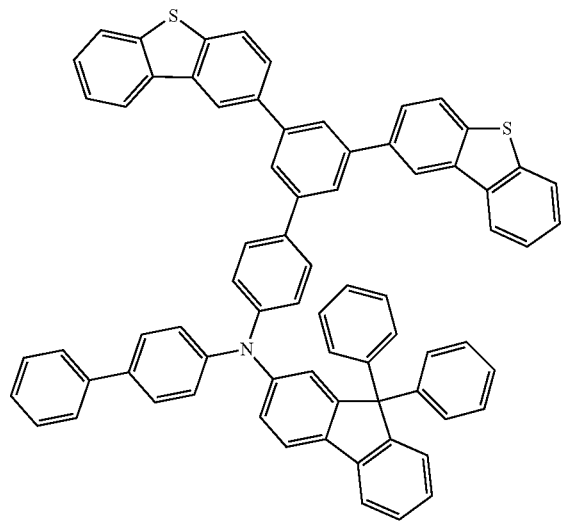
1-22
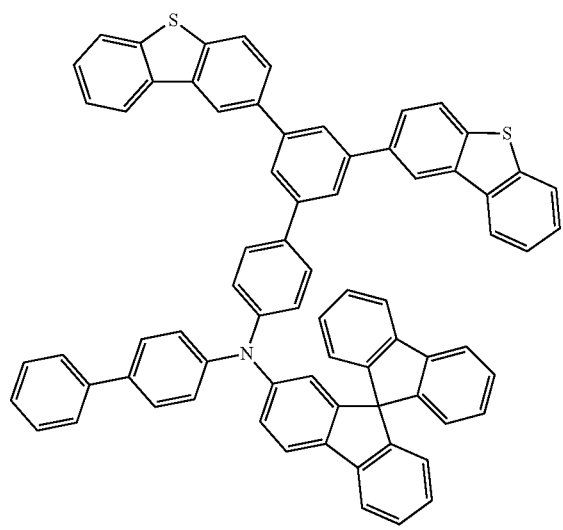
2-5
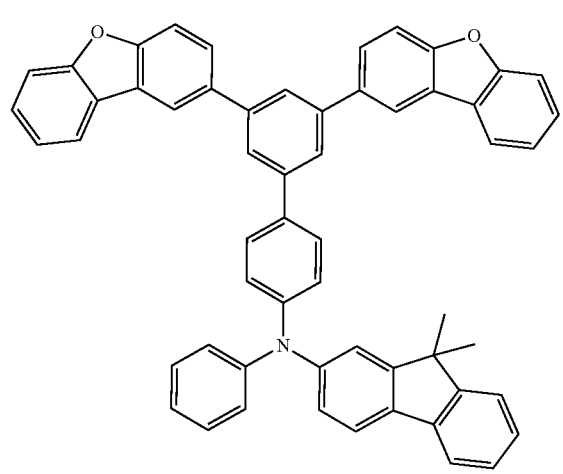
-continued
2-6
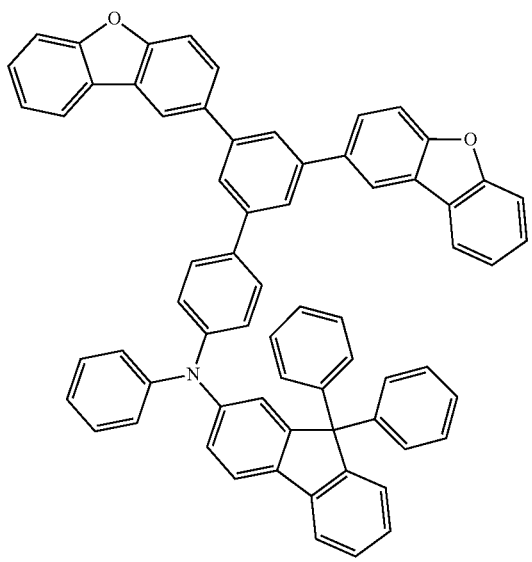
2-7
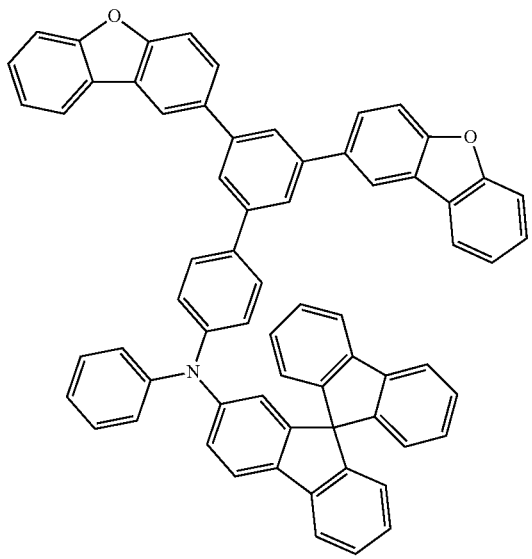
2-11
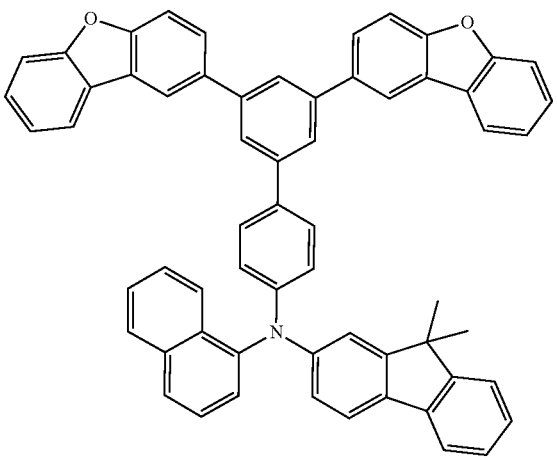

US 11,271,175 B2
2-12
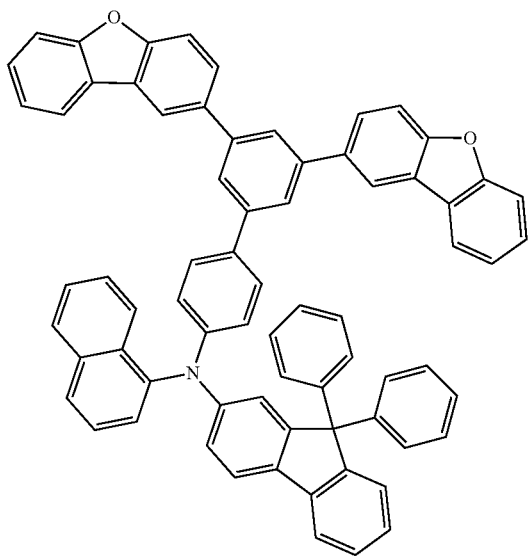
2-13
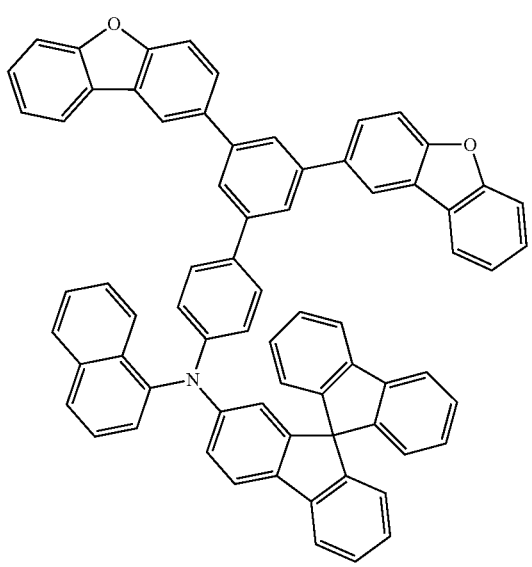
2-16
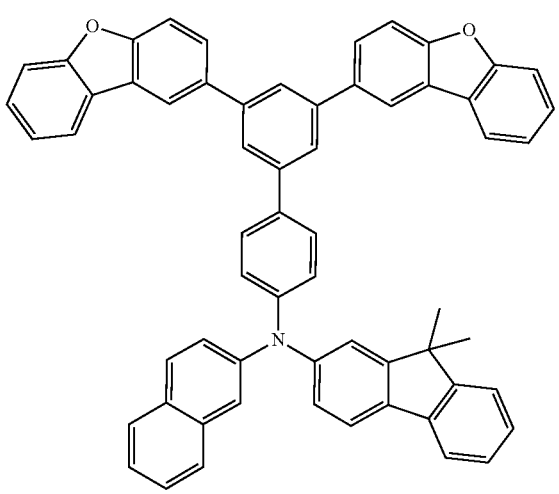
2-17
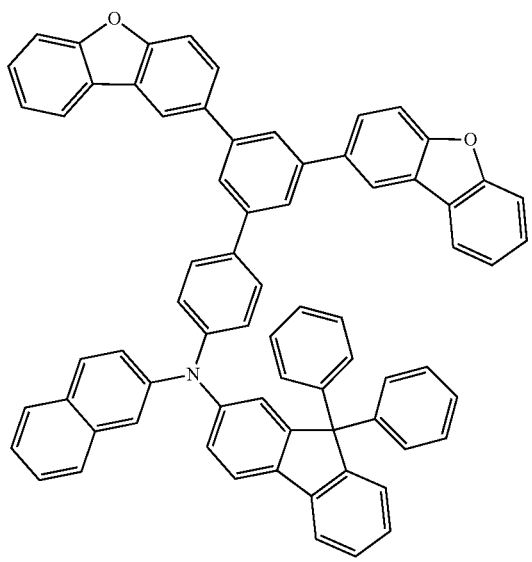
2-18
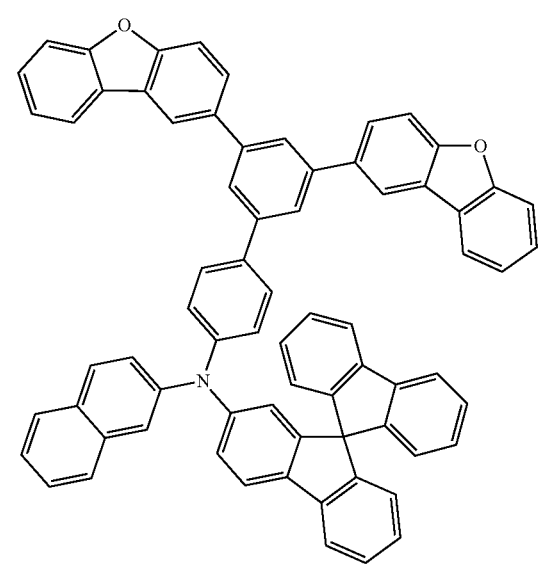
2-20

2-21
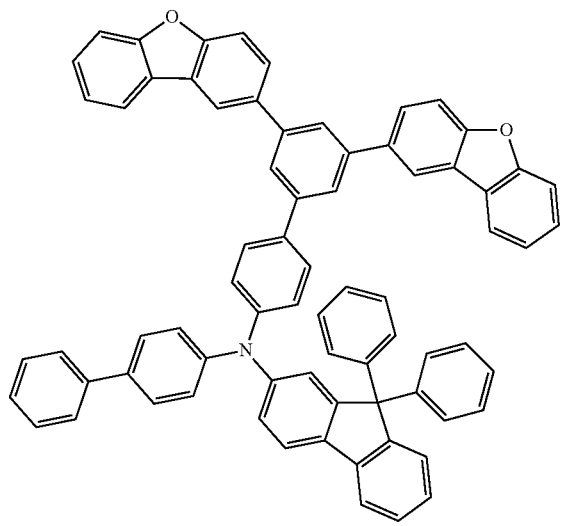
2-22
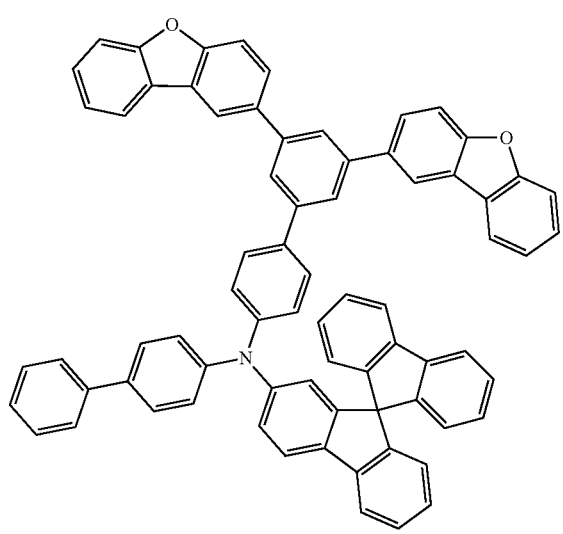
3-5
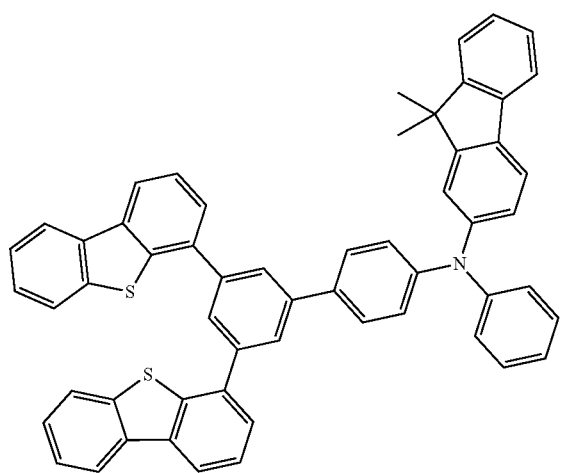
3-6
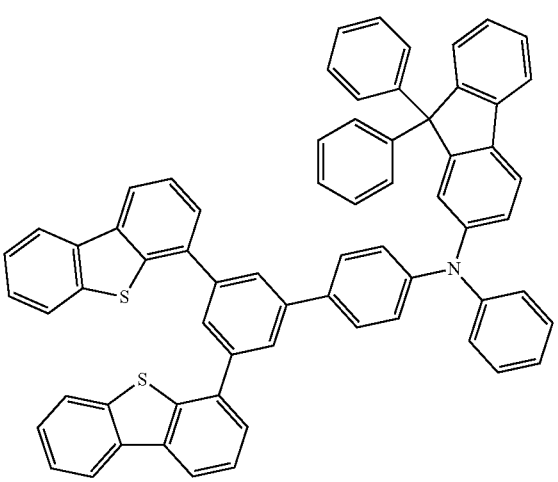
3-7
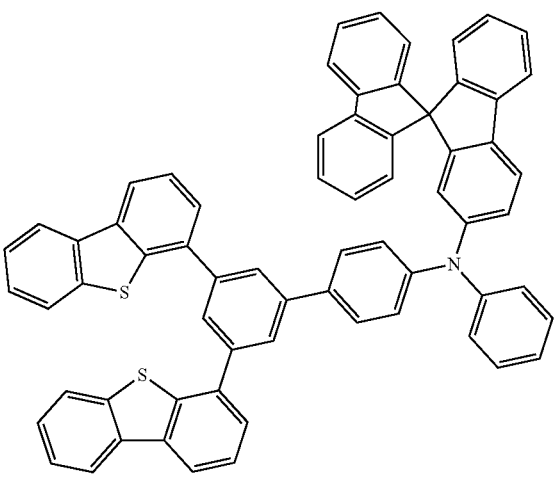
3-11
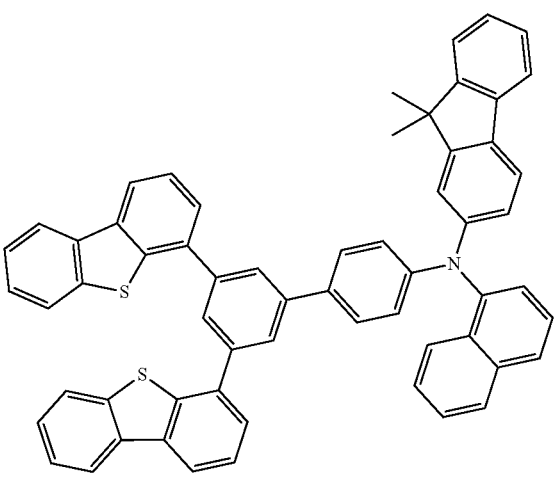

3-12
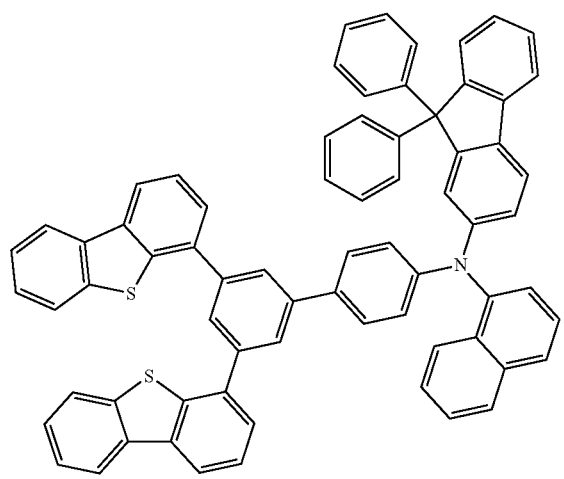
3-17
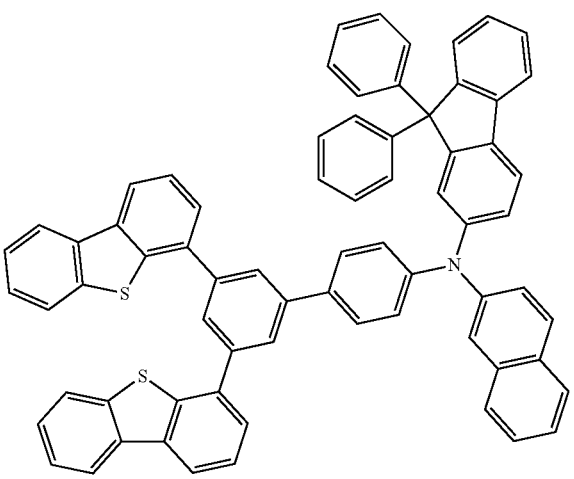
3-13
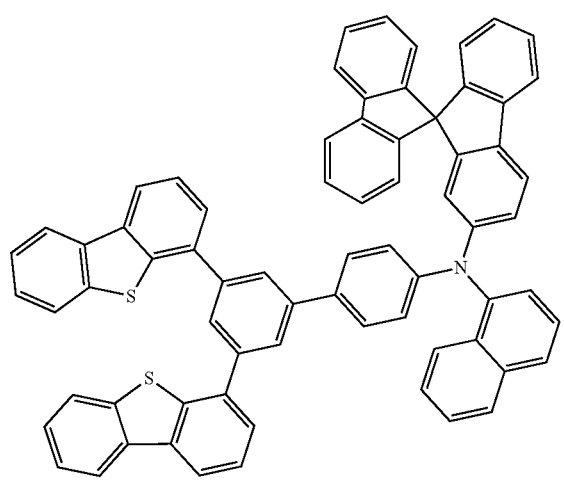
3-18
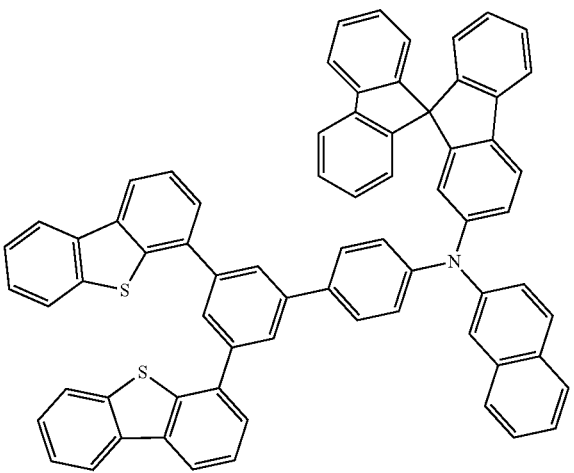
3-16
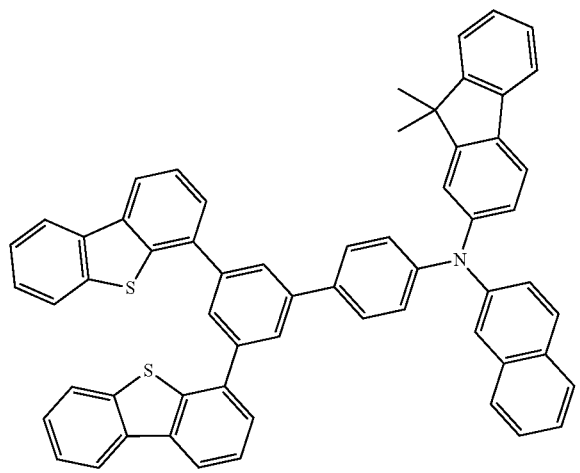
3-20
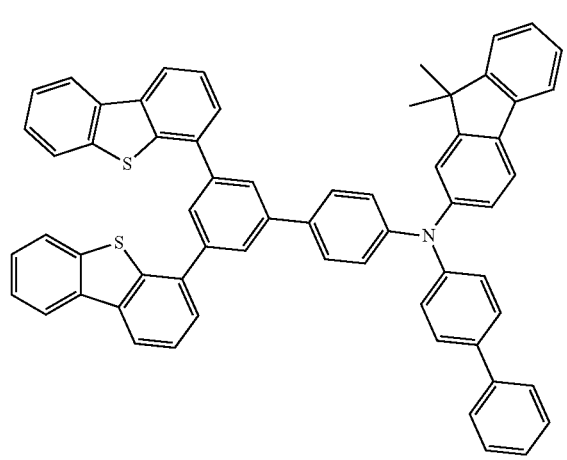

3-21
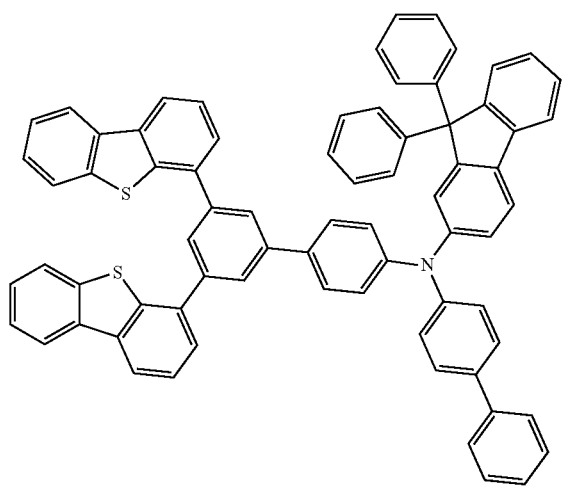
3-22
4-6
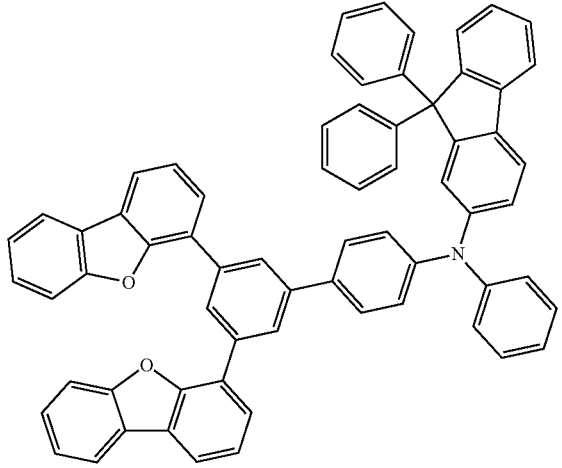
4-7
4-5
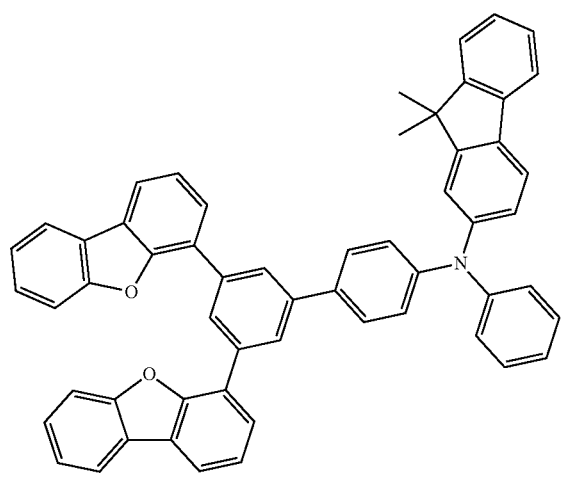
4-11
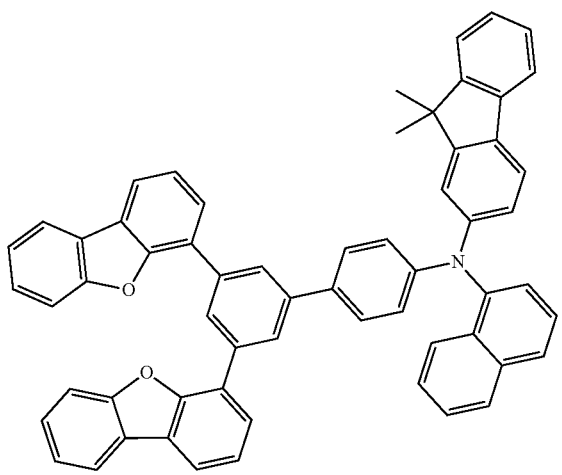

4-12
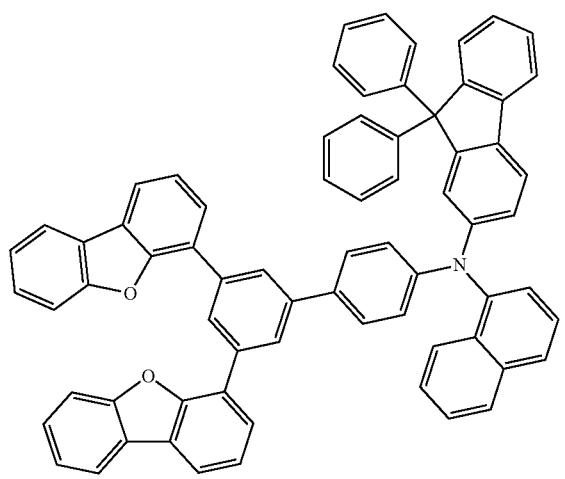
4-17
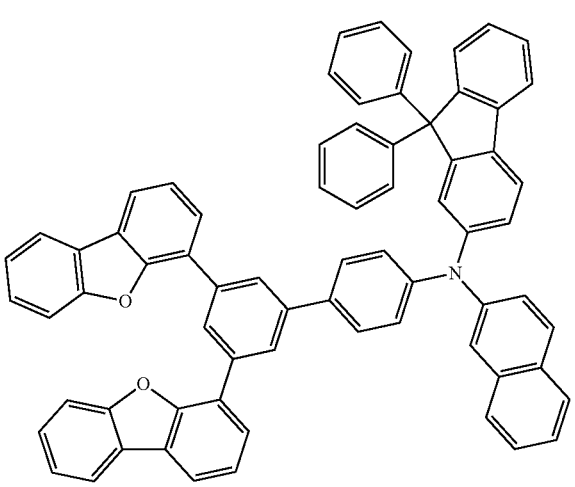
4-13
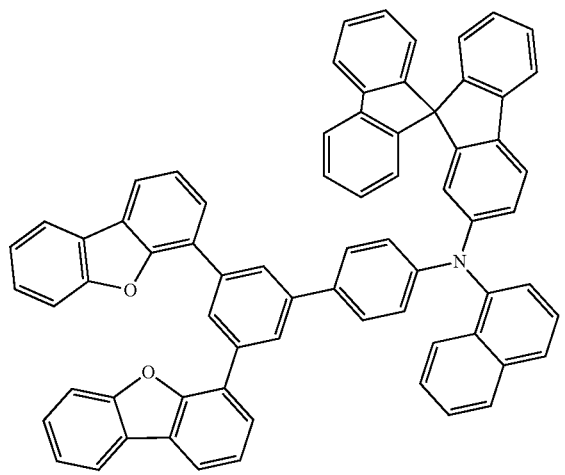
4-18
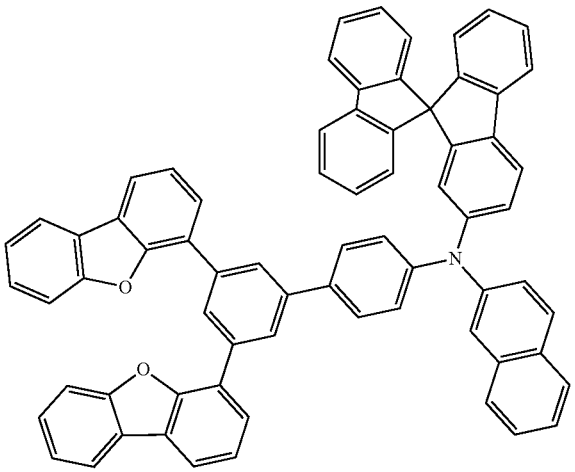
4-16
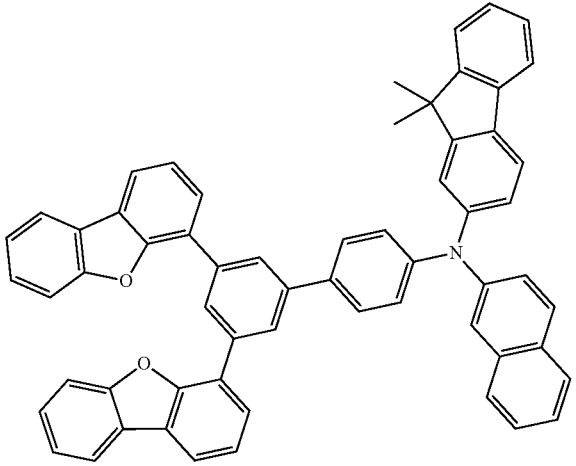
4-20
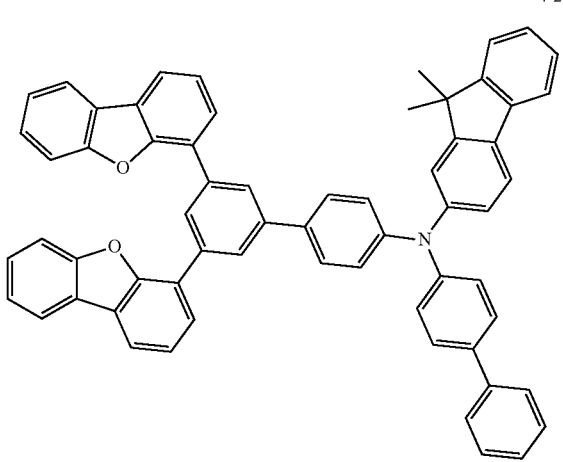

4-21
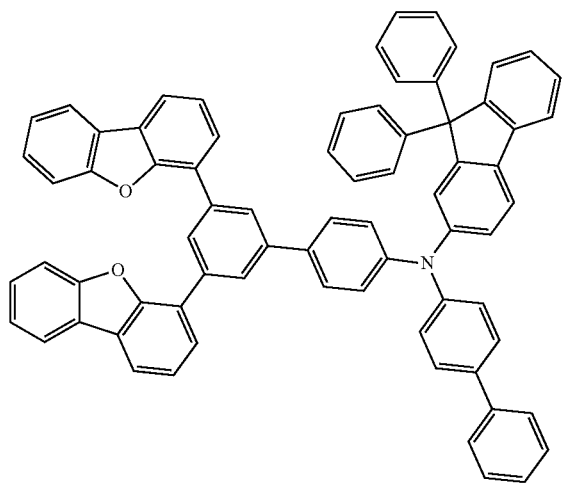
6-5
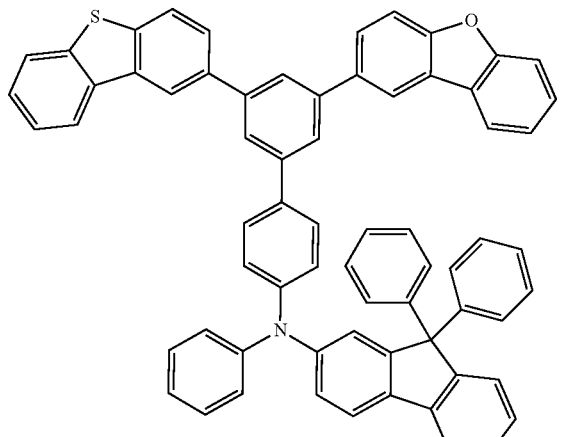
4-22
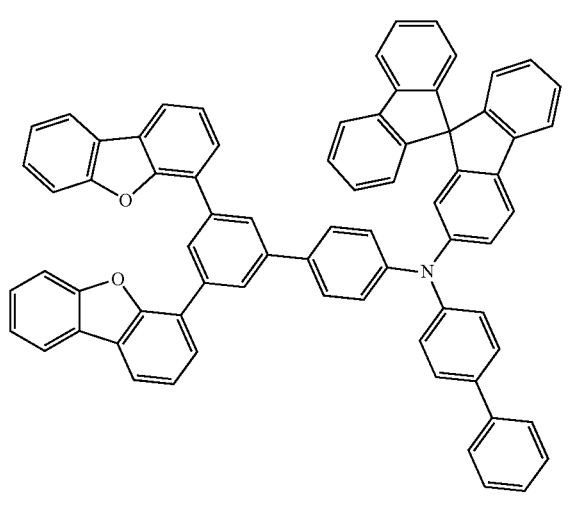
6-7
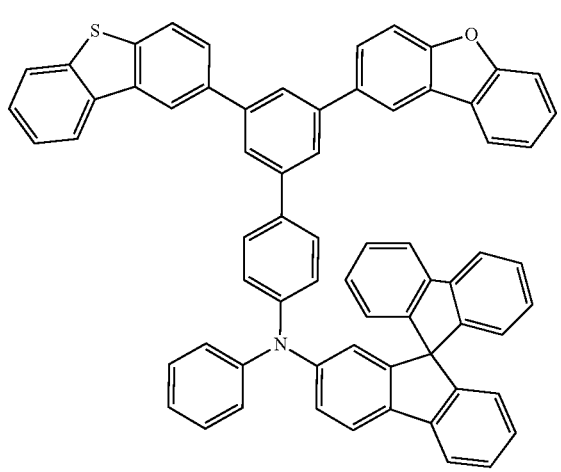
6-5
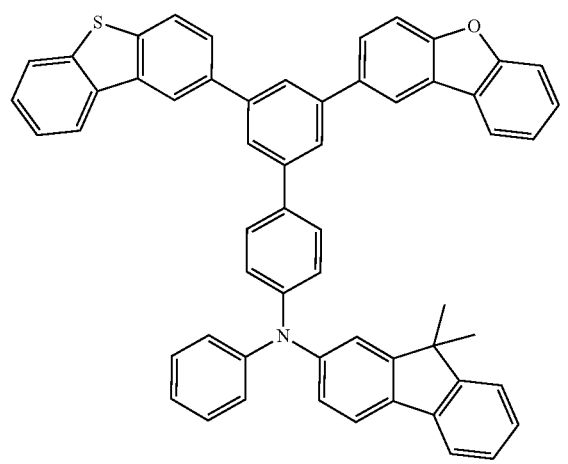
6-11
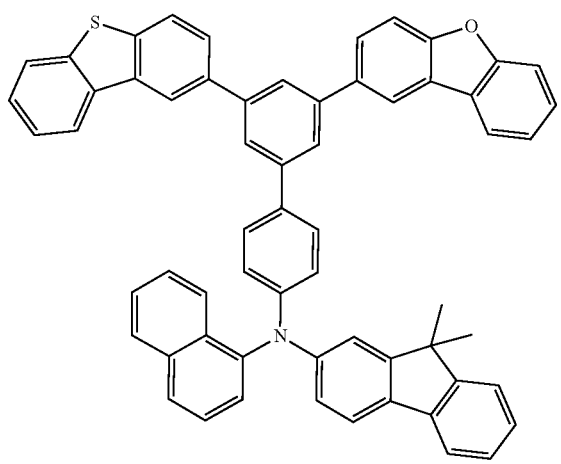

6-12
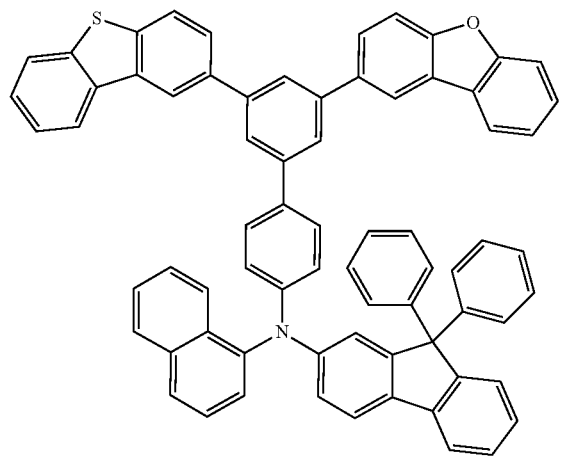
6-13
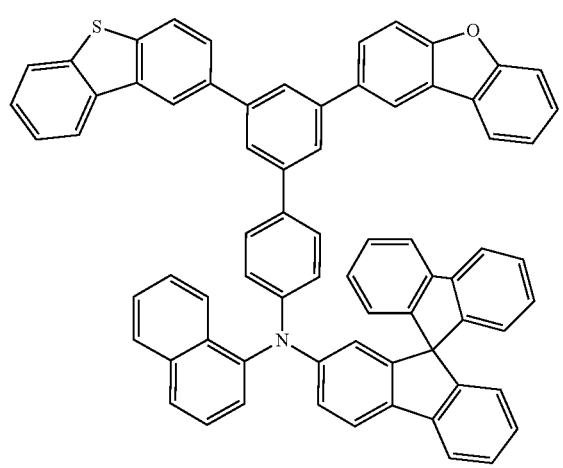
6-16
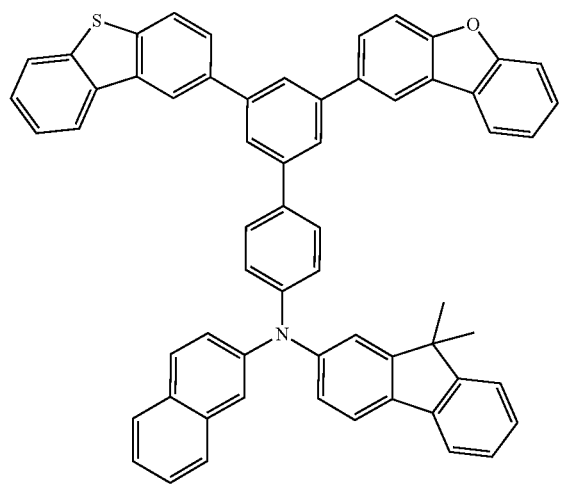
6-17
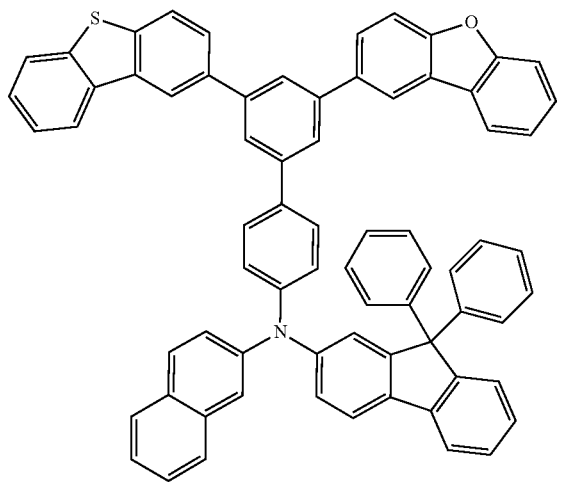
6-18
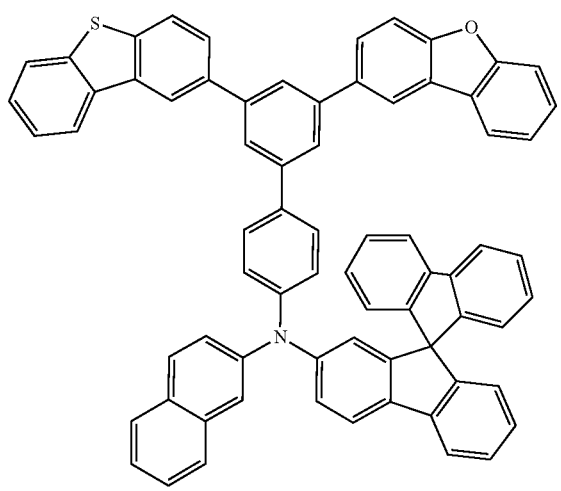
6-20
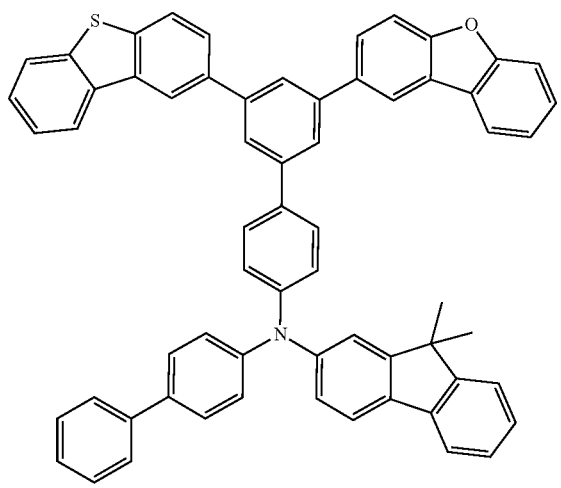

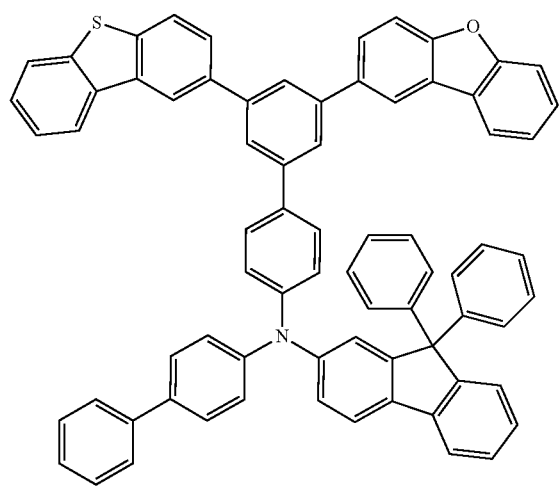

6-21

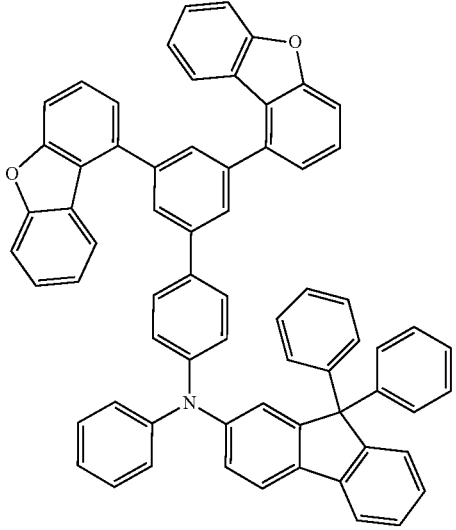

7-6

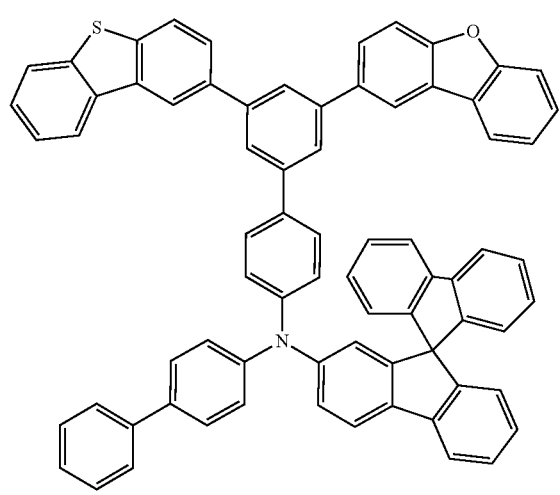

6-22

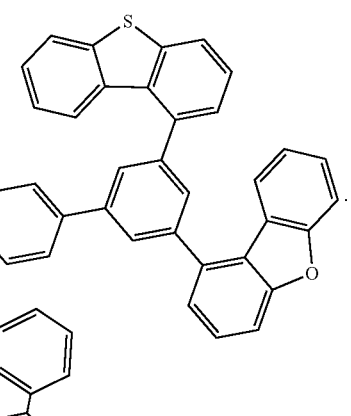

7-7

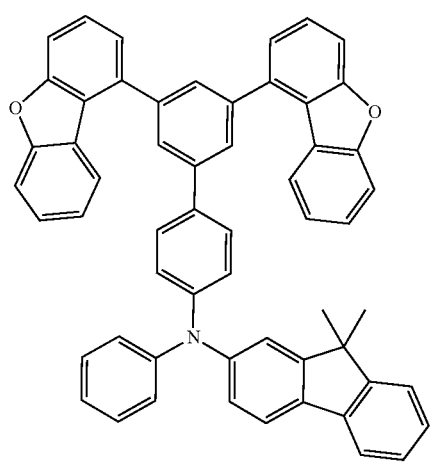

7-5

4. An organic electric element comprising a first electrode, a second electrode, and an organic material layer disposed between the first electrode and the second electrode, wherein the organic material layer comprises the compound of claim 1.

5. The organic electric element of claim 4, wherein the organic material layer comprises at least one layer of a hole injection layer, a hole transport layer, and an emission-auxiliary layer.

6. The organic electric element of claim 4, wherein the organic material layer comprises a light emitting layer and the light emitting layer comprises the compound.

7. The organic electric element of claim 4, further comprising at least one layer to improve luminous efficiency formed on at least one of two sides of the first and second electrodes, the side being opposite to the organic material layer.

8. The organic electric element of claim 4, wherein the organic material layer is formed by a process of spin coating, nozzle printing, inkjet printing, slot coating, dip coating or roll-to-roll.

9. An electronic device comprising a display device, which comprises the organic electric element of claim 4, and a control unit for driving the display device.

10. The electronic device of claim 7, wherein the organic electric element comprises at least one of an organic light emitting diode, an organic solar cell, an organic photo conductor, an organic transistor, and an element for monochromatic or white illumination.

\* \* \* \* \*